(12) United States Patent
Georges et al.

(10) Patent No.: US 7,226,748 B2
(45) Date of Patent: Jun. 5, 2007

(54) HSC70 DIRECTED DIAGNOSTICS AND THERAPEUTICS FOR MULTIDRUG RESISTANT NEOPLASTIC DISEASE

(75) Inventors: Elias Georges, Laval (CA); Lucile Serfass, Montreal (CA); Anne-Marie Bonneau, Laval (CA); Frédéric Dallaire, Montreal (CA)

(73) Assignee: Aurelium BioPharma, Inc., Montreal, Quebec (CA)

( * ) Notice: Subject to any disclaimer, the term of this patent is extended or adjusted under 35 U.S.C. 154(b) by 378 days.

(21) Appl. No.: 10/737,350

(22) Filed: Dec. 15, 2003

(65) Prior Publication Data
US 2004/0185511 A1 Sep. 23, 2004

Related U.S. Application Data

(60) Provisional application No. 60/438,012, filed on Jan. 3, 2003.

(51) Int. Cl.
*G01N 33/53* (2006.01)
(52) U.S. Cl. .................. 435/7.1; 436/501; 436/518
(58) Field of Classification Search ............... None
See application file for complete search history.

(56) References Cited

U.S. PATENT DOCUMENTS

| | | |
|---|---|---|
| 4,444,744 A | 4/1984 | Goldenberg |
| 4,720,386 A | 1/1988 | McCollester |
| 5,194,384 A | 3/1993 | Bystryn |
| 5,407,653 A | 4/1995 | Piwnica-Worms |
| 5,762,930 A | 6/1998 | Fanger et al. |
| 5,801,154 A | 9/1998 | Frank et al. |
| 6,338,853 B1 | 1/2002 | Bystryn |
| 6,352,996 B1 | 3/2002 | Cao et al. |
| 6,406,689 B1 | 6/2002 | Falkenberg et al. |
| 6,417,336 B1 | 7/2002 | Morishima et al. |
| 6,476,193 B1 | 11/2002 | Nandabalan et al. |
| 6,511,676 B1 | 1/2003 | Boulikas |
| 6,562,347 B1 | 5/2003 | Kwak et al. |
| 6,572,856 B1 | 6/2003 | Taylor et al. |
| 6,593,087 B2 | 7/2003 | Prichard et al. |
| 6,623,923 B1 | 9/2003 | Xu et al. |
| 6,630,327 B1 | 10/2003 | Mechetner et al. |
| 6,657,048 B2 | 12/2003 | Young et al. |
| 2002/0061316 A1 | 5/2002 | Srivastava |
| 2002/0110912 A1 | 8/2002 | Ralhan et al. |
| 2002/0198139 A1 | 12/2002 | Deutschman et al. |
| 2003/0012793 A1 | 1/2003 | Srivastava et al. |
| 2003/0012794 A1 | 1/2003 | Srivastava et al. |
| 2003/0031661 A1 | 2/2003 | Graner et al. |
| 2003/0087412 A1 | 5/2003 | Nandabalan et al. |
| 2003/0157081 A1 | 8/2003 | Bonini et al. |
| 2003/0165519 A1 | 9/2003 | Srivastava |
| 2003/0180721 A1 | 9/2003 | Witkin |

FOREIGN PATENT DOCUMENTS

| | | |
|---|---|---|
| DE | 41 12999 A1 | 10/1992 |
| EP | 0813872 A | 12/1997 |
| WO | WO 02/071061 A | 9/2002 |
| WO | WO 02/082076 A2 | 10/2002 |
| WO | WO 03/008542 A | 1/2003 |

OTHER PUBLICATIONS

Gehrmann et al., Cell Stress Chaperones. Jun. 2005; 10(2): 136-146.*
U.S. Appl. No. 10/737,712, filed Dec. 15, 2003, Georges et al.
U.S. Appl. No. 10/736,889, filed Dec. 15, 2003, Georges et al.
U.S. Appl. No. 10/801,988, filed Mar. 15, 2004, Georges et al.
Abou-Jawde et al., An Overview of Targeted Treatments in Cancer, Clinical Therapeutics, vol. 25, No. 8, 2003, pp. 2121-2137.
Alqawi and Georges, The multidrug resistance protein ABCC1 drug-binding domains show selective sensitivity to mild detergents, Biochemical and Biophysical Research Communications 303, 2003, pp. 1135-1141.
Barreto et al., Stress-induced release of HSC70 from human tumors, Cellular Immunology 222, 2003, pp. 97-104.
Cheng et al., Retaining of the Assembly Capability of Vimentin Phosphorylated by Mitogen-Activated Protein Kinase-Activated Protein Kinase-2, Journal of Cellular Biochemistry, 89, 2003, pp. 589-602.
Den Boer et al., Relationship Between Major Vault Protein/Lung Resistance Protein, Multidrug Resistance-Associated Proten, P-Glycoprotein Expression, and Drug Resistance in Childhood Leukemia, Blood, vol. 91, No. 6, 1998, pp. 2092-2098.
Di Pietro et al., Modulation by flavonoids of cell multidrug resistance mediated by P-glycoprotein and related ABC transporters, Cell. Mol. Life Sci. 59, 2002, pp. 307-322.
Du et al., Dual Requirement fro Rho and Protein Kinase C in Direct Activation of Phospholipase D1 Through G Protein-coupled Receptor Signaling, Molecular Biology of the Cell, vol. 11, 2000, pp. 4359-4368.
Durbin et al., An epitope on carcinoembryonic antigen defined by the clinically relevant antibody PR1A3, Proc. Natl. Acad. Sci. USA, vol. 91, 1994, pp. 4313-4317.
Faigle et al., Vimentin Filaments in Fibroblasts Are a Reservoir for SNAP23, a Component of the Membrane Fusion Machinery, Molecular Biology of the Cell, vol. 11, 2000, pp. 3485-3494.
Feig, Designer Drugs: New Directed Therapies for Cancer, International Journal of Hematology Suppl. II, 76, 2002, pp. 281-283.

(Continued)

*Primary Examiner*—Misook Yu
(74) *Attorney, Agent, or Firm*—Wilmer Cutler Pickering Hale and Dorr LLP

(57) ABSTRACT

Disclosed are methods for detecting neoplastic or damaged cells and for detecting multidrug resistance in neoplastic or damaged cells by detecting an increase in the cell surface expression of a heat shock cognate (HSC70) protein 70 on the surface of such a multidrug resistant neoplastic or damaged cells as compared to the level of expression of the HSC70 protein on the surface of a normal cell.

9 Claims, 28 Drawing Sheets

OTHER PUBLICATIONS

Fujita et al., High Molecular Weight Vimentin Complex Is Formed after Proteolytic Digestion of Vimentin by Caspase-3: Detection by Sera of Patients with Interstitial Pneumonia, Microbiol. Immunol., 47(6), 2003, pp. 447-451.

Garnett, Targeted drug conjugates: principles and progress, Advanced Drug Delivery Reviews, 53, 2001, pp. 171-216.

Goto et al., Phosphorylation and reorganization of vimentin by p21-activated kinase (PAK), Genes of Cells, 7, 2002, pp. 91-97.

Gratama et al., Flow Cytometric Quantitative of Immunofluorescence Intensity: Problems and Perspectives, Cytometry 33, 1998, pp. 166-178.

Heidenthal et al., The Binding in Vitro of Modified LDL to the Intermediate Filament Protein Vimentin, Biochemical and Biophysical Research Communications, 267, 2000, pp. 49-53.

Herrmann and Aebi, Intermediate filaments and their associates: multi-talented structural elements specifying cytoarchitecture and cytodynamics, Current Opinion in Cell Biology, 12, 2000, pp. 79-90.

Hubert et al., STEAP: A prostate-specific cell-surface antigen highly expressed in human prostate tumors, PNAS, vol. 96, No. 25, 1999, pp. 14523-14528.

Iqbal and Lenz, Targeted Therapy and Pharmacogenomic Programs, Cancer Supplement, vol. 97, No. 8, 2003, pp. 2076-2082.

Kim et al., Multidrug Resistance-Associated Protein (MRP) is expressed in osteosarcoma but is not a significant me[c]hanism of drug resistance, 47th Ann. Mtg., Orthopaedic Research Society, 2001, p. 0855.

Kim, Targeted therapies for the treatment of cancer, The American Journal of Surgery, 186, 2003, pp. 264-268.

Kown et al., In Vivo Imaging of Acute Cardiac Rejection in Human Patients Using 99m Technetium Labeled Annexin V, American Journal of Transplantation, 1, 2001, pp. 270-277.

Kreitman and Pastan, Immunotoxins for targeted cancer therapy, Advanced Drug Delivery Reviews, 31, 1998, pp. 53-88.

Ling, Multidrug resistance: molecular mechanisms and clinical relevance, Cancer Chemother, Pharmacol., 40 Suppl., 1997, pp. S3-S8.

Meschini et al., Intracellular P-glycoprotein expression is associated with the intrinsic multidrug resistance phenotype in human colon adenocarcinoma cells, Int. J. Cancer, 87, 2000, pp. 615-628.

Mor-Vaknin et al., Vimentin is secreted by activated marcophages, Nature Cell Biology, vol. 5, 2003, pp. 59-63.

Park, Tumor-directed Targeting of Liposomes, Bioscience Reports., vol. 22, No. 2, 2002, pp. 267-281.

Patterson et al., Reduced Numatrin/B23/Nucleophosmin Labeling in Apoptotic Jurkat T-lymphoblasts, The Journal of Biological Chemistry, vol. 270, No. 16, 1995, pp. 9429-9436.

Rots et al., Targeted cancer gene therapy: the flexibility of adenoviral gene therapy vectors, Journal of Controlled Release, 87, 2003, pp. 159-165.

Rowlinson-Busza and Epenetos, Targeted delivery of biologic and other antineoplastic agents, Current Opinion in Oncology, 4, 1992, 1142-1148.

Schroeijers et al., the Mr 193,000 Vault Protein Is Up-Regulated in Multidrug-resistant Cancer Cell Lines, Cancer Research, 60, 2000, pp. 1104-1110.

Wehner et al., Expression levels of hsc70 and hsp60 are developmentally regulated during B-cell maturation and not associated to childhood c-ALL at presentation or relapse, Eur. J. Haematol., 71, 2003, pp. 100-108.

Steinert et al., A High Molecular Weight Intermediate Filament-associated Protein in BHK-21 Cells Is Nestin, a Type VI Intermediate Filament Protein, The Journal of Biological Chemistry, vol. 274, No. 14, 1999, pp. 9881-9890.

Strelkov et al., Molecular architecture of intermediate filaments, BioEssays, 25, 2003, pp. 243-251.

Trail et al., Monoclonal antibody drug immunoconjugates for targeted treatment of cancer, Cancer Immunol. Immunother, 52, 2003, pp. 328-337.

Treib and Kotz, Proteins expressed in osteosarcoma and serum levels as prognostic factors, The International Journal of Biochemistry & Cell Biology, 33, 2001, pp. 11-17.

Turowski et al., Vimentin Dephosphorylation by Protein Phosphatase 2A Is Modulated by the Targeting Subunit B55, Molecular Biology of the Cell, vol. 10, 1999, pp. 1997-2015.

Wang and Liu, Targeting Strategies in Cancer Gene Therapy, Acta Bochimica et Biophysica Sinica, 35(4), 2003, pp. 311-316.

Wu et al., High-resolution microPET imaging of carcino-embryonic antigen-positive xenografts by using a copper-64-labeled engineered antibody fragment, PNAS, vol. 97, No. 15, 2000, pp. 8495-8500.

Yokota et al., Rapid tumor penetration of a single-chain Fv and comparison with other immunoglobulin forms, Cancer Research, vol. 52, Issue 12, 1992, pp. 3402-3408.

Yasuaki et al., 70 kDa heat shock cognate protein is a transformation-associated antigen and a possible target for the host's antitumor immunity, Journal of Immunology, vol. 151, No. 10, 1993, pp. 5516-5524.

Multhoff et al., A Stress-inducible 75-kDa Heat-shock Protein (HSP72) Is Expressed on the Surface of Human Tumor Cells, But Not on Normal Cells, International Journal of Cancer 1995 United States, vol. 61, No. 2, 1995, pp. 272-279.

Strik et al., Heat Shock Protein Expression in Human Gliomas, Anticancer Research 2000 Nov.-Dec. pp. 4457-4462.

Kiang, et al., Heat Shock Protein 70kDa, Molecular Biology, Biochemistry, and Physiology, Parmacology and Therapeutics, vol. 80, No. 2, Nov. 1998, pp. 183-201.

Volm, Manfred, Multidrug Resistance and Its Reversal, Anticancer Research, vol. 18, No. 4C, Jul. 1998, pp. 2905-2917.

Dermer, BioTechnology, 1994, 12:320.

Drexler et al., Leukemia and Lymphoma, 1993, 9:1-25.

Freshney, Culture of Animal Cells, A Manual of Basic Technique, Alan R. Liss, Inc. 1983, New York, p. 4.

Tockman et al., Cancer Research, 1992, 52:2711s-2718s.

Bichart et al. Cytoskeletion alteration in MCF7R, a multidrug resistant human breast cancer cell line., *Anticancer Res.*, 1997, pp. 3393-3401, vol. 17.

Essa et al., Vimentin expression in different types of breast carinom aimmunohistochemical study, *J. Egypt Soc. Parasitol.*, 1996, pp. 433-442, vol. 26.

Heidenthal et al., The Binding in Vitro of Modified LDL to the Intermediate Filament Protein Vimentin, *Biochemical and Biophysical Research Communications*, 2000, pp. 49-53, vol. 267.

Meschini et al. Intracellular P-Glycoprotein Expression is Associated with the intrinsic Multidrug Resistance Phenotype in Human Colon Adenocarcinoma Cells. *Int. J. Cancer*, (2000), pp. 615-628, vol. 87.

Thomas et al., Association between keratin and Vimentin Expression, Malignant Phenotype and Survival in Postmenopausal Breast Cancer Patients, Oct. 1999, pp. 2698-2703, vol. 5.

Bichart, F., et al., "Cytoskeleton Alteration in MCF7R Cells, a Multidrug Resistant Human Breast Cancer Cell Line," *Anticancer Research*, vol. 17, pp. 3393-3402.

Database Pubmed [Online], "Triosephosphate Isomerase," US National Library of Medicine, XP002301823, Bethesda, MD, Jan. 5, 2001.

Ludwig, A., et al., "Identification of Differential Expressed Genes in Classical and Atypical Multidrug-resistant Gastric Carcinoma Cells," *Anticancer Research*, vol. 17, pp. 3213-3222, 1997.

Moran E., et al., "Co-expression of MDR-Associated Markers, Including P-170, MRP and LRP and Cytoskeletal Proteins, in Three Resistant Variants of the Human Ovarian Carcinoma Cells Line, OAW42," *Eur. J. Cancer*, vol. 33, pp. 652-660, 1997.

Sekiguchi, M., et al., "Biological Characteristics and chemosensitivity profile of four human anaplastic thyroid carcinoma cell lines," *Biomed. Pharmacother*, vol. 55, pp. 466-474, 2001.

Sweet, P., et al., "Cyclosporin A and Verapamil Enhancement of Daunorubicin-produced Nucleolar Protein B23 Translocation in Daunorublcin-resistant and -sensitive Human and Murine Tumor Cells," *Cancer Research*,vol. 49, pp. 677-680, 1989.

Yang, W., et al., "Multi-epitope schistosome vaccine candidates tested for protective immunogenicity in mice," *Vaccine*, vol. 19, pp. 103-113, 2001.

* cited by examiner

Isoform 2 Results

ProFound - Search Result Summary
Version 4.10.8
© 1997-2000 ProteoMetrics

Protein Candidates for search 20010608200436-03942081721231510 [73182 sequences searched]

| Rank | Probability | Est'd Z | Protein Information and Sequence Analyse Tools (T) | % | pI | kDa |
|------|-------------|---------|----------------------------------------------------|----|-----|-------|
| +1   | 1.0e+000    | 2.36    | gi|5729877|ref|NP_006588.1| Heat shock 70 kD protein 8, heat shock 70kD protein 8 (HSP73), heat shock cognate protein, 71 kDa, heat shock 70kd protein 10(HSC71) [Homo sapiens] ® | 25 | 5.4 | 71.11 ® |

FIG. 2A

Search Parameters

Details for rank 1 candidate in search 20010608200436-03942081721231510 gi|5729877|ref|NP_006588.1| heat shock 70 kD protein 8, heat shock 70kD protein 8 (HSP73), heat shock cognate protein, 71 kDa, heat shock 70kd protein 10(HSC71) [Homo sapiens]
gi|13639862|ref|XP_006086.2| heat shock 70kD protein 8 [Homo sapiens]
gi|123648|sp|P11142|HS7C HUMAN HEAT SHOCK COGNATE 71 KDA PROTEIN
gi|87625|pir||A27077 dnaK-type molecular chaperone-human
gi|32467|emb|CAA68445.1|(Y00371) 71 Kd heat shock cognate protein [Homo sapiens]
gi|13273304|gb|AAK17898.1|AF352832_1(AF352832) constitutive heat shock protein 70 [Homo sapiens]

Sample ID        NO CHANGE   [Pass 0]
Measured peptides       20
Matched peptides        12
Min. sequence coverage  25%

FIG. 2B

12 Peptides Sequenced*

| | Measured Mass (M) | Avg/ Mono | Computed Mass | Error (ppm) | Residues Start | To | Missed Cut | Peptide sequence |
|---|---|---|---|---|---|---|---|---|
| -1 | 1250.623 | M | 1250.611 | 10 | 237 | 246 | 0 | MVNHFIAEFK |
| | | | | | | | | (1) +O@M; |
| -2 | 1252.592 | M | 1252.608 | -13 | 302 | 311 | 0 | FEELNADLFR |
| -3 | 1406.696 | M | 1406.712 | -12 | 237 | 247 | 1 | MVNHFIAEFKR |
| | | | | | | | | (1) +O@M; |
| -4 | 1479.743 | M | 1479.746 | -2 | 300 | 311 | 1 | ARFEELNADLFR |
| -5 | 1486.756 | M | 1486.693 | 42 | 37 | 49 | 0 | TTPSYVAFTDTER |
| -6 | 1690.705 | M | 1690.718 | -7 | 221 | 236 | 0 | STAGDTHLGGEDFDNR |
| -7 | 1786.968 | M | 1786.982 | -8 | 172 | 188 | 1 | IINEPTAAAIAYGLDKK |
| -8 | 1820.874 | M | 1820.883 | -5 | 57 | 72 | 1 | NQVAMNPTNTVFDAKR |
| | | | | | | | | (1) +O@M; |
| -9 | 1837.001 | M | 1837.005 | -2 | 326 | 342 | 1 | LDKSQIHDIVLVGGSTR |
| -10 | 1951.065 | M | 1951.052 | 7 | 452 | 469 | 1 | DNNLLGKFELTGIPPAPR |
| -11 | 1980.996 | M | 1980.990 | 3 | 138 | 155 | 0 | TVTNAVTVPAYFNDSQR |
| -12 | 2773.258 | M | 2773.318 | -21 | 424 | 447 | 0 | QTQTFTTYSDNQPGVLIQVYEGER |

*25% of the amino acids of the HSC70 protein were represented in the amino acids of the mass peptides analyzed.

FIG. 2C

```
1    MSKGPAVGIDLGTTYSCVGVFQHGKVEIIANDQGNRTTPSYVAFTDTERLIGDAAKNQVA
61   MNPTNTVFDAKRLIGRRFDDAVVQSDMKHWPFMVVNDAGRPKVQVEYKGETKSFYPEEVS
121  SMVLTKMKEIAEAYLGKTVTNAVVTVPAYFNDSQRQATKDAGTIAGLNVLRIINEPTAAA
181  IAYGLDKKVGAERNVLIFDLGGGTFDVSILTIEDGIFEVKSTAGDTHLGGEDFDNRMVNH
241  FIAEFKRKHKKDISENKRAVRRLRTACERAKRTLSSSTQASIEIDSLYEGIDFYTSITRA
301  RFEELNADLFRGTLDPVEKALRDAKLDKSQIHDIVLVGGSTRIPKIQKLLQDFFNGKELN
361  KSINPDEAVAYGAAVQAAILSGDKSENVQDLLLLDVTPLSLGIETAGGVMTVLIKRNTTI
421  PTKQTQTFTTYSDNQPGVLIQVYEGERAMTKDNNLLGKFELTGIPPAPRGVPQIEVTFDI
481  DANGILNVSAVDKSTGKENKITITNDKGRLSKEDIERMVQEAEKYKAEDEKQRDKVSSKN
541  SLESYAFNMKATVEDEKLQGKINDEDKQKILDKCNEIINWLDKNQTAEKEEFEHQQKELE
601  KVCNPIITKLYQSAGGMPGGMPGGFPGGGAPPSGGASSGPTIEEVD
```

FIG. 3

BOLD = Peptides covered by MS MALDI analysis

| ProFound -Search Result Summary | | | | | Version 4.10.5 |
|---|---|---|---|---|---|
| Protein Candidates for search BD36B5S9-CG5C-289FB336 [88967 sequences searched] | | | | | The Rockefeller University Edition |
| Rank | Probability | Est'd Z | Protein Information and Sequence Analyse Tools (T) | % | pI | kDa ® |
| +1 | 1.0e+000 | 2.43 | T gi\|5729877\|ref\|NP_006588.1\| (NM_006597) heat shock 70kd protein 8, heat shock 70kD protein 8(HSP73), heat shock cognate protein 71-kDa, heat shock 70kd protein 10 (HSC71) [Homo sapiens] | 26 | 5.4 | 71.11 ® |

Search Parameters

| Input Summary | |
|---|---|
| Date & Time | Mon Dec 17 01 01:33 2001 UTC (Search Time: 2 80 sec) |
| Sample ID | |
| Database | NCBInr (2001/12/11) |
| Taxonomy Category | Homo sapiens (human) |
| Protein Mass Range | 60 - 90 kDa |
| Protein pI range | 4.0 - 5.5 |
| Search for | Single protein only |
| Digest Chemistry | Trypsin |
| Max Missed Cut | 2 |
| Modifications | +C2H3ON@C(Complete), +O@M(Partial),  C22H37N4O4S@K(Partial); |
| Charge State | MH+ |
| Peptide Masses (Da,Average) | |
| Tolerance(AVG) | 100.00 ppm |
| Peptide Masses (Da,Monoisotopic) | 1199.667 1253.610 1401.805 1407.785 1463.128 1480.751 1487.698 1691.729 1830.802 1838.043 1966.104 1982.001 1994.000 2231.141 2275.180 2278.081 2757.251 2774.246 2998.417 3548.224 |
| Tolerance(MON) | 100.00 ppm |
| Number of Peptides | 20 |

*12 Peptides Sequenced**

| Measured peptides | : 20 |
| --- | --- |
| Matched peptides | : 12 |
| Min. sequence coverage | : 26% |

Boxed peptides are biotinylated

| # | | | | | | | Sequence |
| --- | --- | --- | --- | --- | --- | --- | --- |
| -1 | 1198.659 | M | 1198.666 | -6 | 160 | 171 | 0 | DAGTIAGLNVLR |
| -2 | 1252.602 | M | 1252.608 | -5 | 302 | 311 | 0 | FEELNADLFR |
| -3 | 1406.777 | M | 1406.712 | 46 | 237 | 247 | 1 | MVNRFIAEFKR |
| -4 | 1479.744 | M | 1479.746 | -2 | 300 | 311 | 1 | ARFEEINADLFR |
| -5 | 1486.690 | M | 1486.693 | -2 | 37 | 49 | 0 | TTPSYVAFTDTER |
| -6 | 1690.721 | M | 1690.726 | 2 | 221 | 236 | 0 | STAGDTHLGGEDFDNR |
| -7 | 1837.035 | M | 1837.005 | 16 | 326 | 342 | 1 | LDKSQTHDIVLVGGSTR |
| -8 | 1965.096 | M | 1965.083 | 7 | 312 | 325 | 2 | GTLDPVEKALRDAK |
| -9 | 1980.994 | M | 1980.990 | 2 | 138 | 155 | 0 | TVTNAVVTVPAYFNDSQR |
| -10 | 1980.994 | M | 1980.956 | 19 | 518 | 533 | 3 | MVQFAEKYKAEDEKQR |
| -11 | 2274.272 | M | 2274.136 | 16 | 57 | 72 | 1 | NQVAAMNPTNTVFDAKR |
| -12 | 2773.238 | M | 2773.318 | -29 | 424 | 447 | 0 | QTQTFTTYSDNQPGVLIQVYEGER |
| -13 | 2997.409 | M | 2997.452 | -14 | 540 | 557 | 1 | NSLESYAFNMKATVEDEK |

*26% of the amino acids of the HSC70 protein were represented in the amino acids of the mass peptides analyzed. Note that 2 and 4 represent the same peptide

FIG. 5C

1    MSKGPAVGIDLGTTYSCVGVFQHGKVEIIANDQGNRTTPSYVAFTDTERLIGDAAK*NQVA*
61   *MNPTNTVFDAKR*LIGRRFDDAVVQSDMKHWPFMVVNDAGRPKVQVEYKGETKSFYPEEVS
121  SMVLTKMKEIAEAYLGKTVTNAVVTVPAYFNDSQRQATKDAGTIAGLNVLRIINEPTAAA
181  IAYGLDKKVGAERNVLIFDLGGGTFDVSILTIEDGIFEVKSTAGDTHLGGEDFDNRMVNH
241  FIAEFKRKHKKDISENKRAVRRLRTACERAKRTLSSSTQASIEIDSLYEGIDFYTSITRA
301  RFEELNADLFR*GTLDPVEKALRDAK*LDKSQIHDIVLVGGSTRIPKIQKLLQDFFNGKELN
361  KSINPDEAVAYGAAVQAAILSGDKSENVQDLLLLDVTPLSLGIETAGGVMTVLIKRNTTI
421  PTKQTQTFTTYSDNQPGVLIQVYEGERAMTKDNNLLGKFELTGIPPAPRGVPQIEVTFDI
481  DANGILNVSAVDKSTGKENKITITNDKGRLSKEDIERMVQEAEKYKAEDEKQRDKVSSK*N*
541  *SLESYAFNMKAT VEDEK*LQGKINDEDKQKILDKCNEIINWLDKNQTAEKEEFEHQQKELE
601  KVCNPIITKLYQSAGGMPGGMPGGFPGGGAPPSGGASSGPTIEEVD

BOLD = Nonbiotinylated peptides specific for HSC70
*Underlined & Italics* = Biotinylated peptides

FIG. 6

Biotinylated total cell extracts

← Probed with Anti-HSC70

Streptavidin purified extracts

← Probed with Anti-HSC70

IP with anti-HSC70

← Probed with Anti-HSC70

IP with anti-HSC70

← Probed with Streptavidin-HRP

POLYPEPTIDE SEQUENCE OF HUMAN HSC70
(GENBANK ACCESSION NO. AAK17898 (SEQ ID NO. 1))

```
  1  MSKGPAVGID  LGTTYSCVGV  FQHGKVEIIA  NDQGNRTTPS  YVAFTDTERL  IGDAAKNQVA
 61  MNPTNTVFDA  KRLIGRRFDD  AVVQSDMKHW  PFMVVNDAGR  PKVQVEYKGE  TKSFYPEEVS
121  SMVLTKMKEI  AEAYLGKTVT  NAVVTVPAYF  NDSQRQATKD  AGTIAGLNVL  RIINEPTAAA
181  IAYGLDKKVG  AERNVLIFDL  GGGTFDVSIL  TIEDGIFEVK  STAGDTHLGG  EDFDNRMVNH
241  FIAEFKRKHK  KDISENKRAV  RRLRTACERA  KRTLSSSTQA  SIEIDSLYEG  IDFYTSITRA
301  RFEELNADLF  RGTLDPVEKA  LRDAKLDKSQ  IHDIVLVGGS  TRIPKIQKLL  QDFFNGKELN
361  KSINPDEAVA  YGAAVQAAIL  SGDKSENVQD  LLLLDVTPLS  LGIETAGGVM  TVLIKRNTTI
421  PTKQTQTFTT  YSDNQPGVLI  QVYEGERAMT  SKEDIERMVQ  EAEKYKAEDE  VPQIEVTFDI
481  DANGILNVSA  VDKSTGKENK  ITITNDKGRL  SKEDIERMVQ  EAEKYKAEDE  KQRDKVSSKN
541  SLESYAFNMK  ATVEDEKLQG  KINDEDKQKI  LDKCNEIINW  LDKNQTAEKE  EFEHQQKELE
601  KVCNPIITKL  YQSAGGMPGG  MPGGFPGGGA  PPSGGASSGP  TIEEVD
```

FIG. 14A

DNA SEQUENCE OF HUMAN HUMAN HSC70
(GENBANK ACCESSION NO. AF352832 (SEQ ID NO. 2))

```
  1  ATGTCCAAGG GACCTGCAGT TGGTATTGAT CTTGGCACCA CCTACTCTTG TGTGGGTGTT
 61  TTCCAGCACG GAAAAGTCGA GATAATTGCC AATGATCAGG GAAACCGAAC CACTCCAAGC
121  TATGTCGCCT TTACGGACAC TGAACGGTTG ATCGGTGATG CCGCAAAGAA TCAAGTTGCA
```

```
 181  ATGAACCCCA CCAACACAGT TTTTGATGCC AAACGTCTGA TTGGACGCAG ATTTGATGAT
 241  GCTGTTGTCC AGTCTGATAT GAAACATTGG CCCTTTATGG TGGTGAATGA TGCTGGCAGG
 301  CCCAAGGTCC AAGTAGAATA CAAGGGAGAG ACCAAAAGCT TCTATCCAGA GGAGGTGTCT
 361  TCTATGGTTC TGACAAAGAT GAAGGAAATT GCAGAAGCCT ACCTTGGGAA GACTGTTACC
 421  AATGCTGTGG TCACAGTGCC AGCTTACTTT AATGACTCTC AGCGTCAGGC TACCAAAGAT
 481  GCTGGAACTA TTGCTGTGCT CAATGTACTT AGAATTATTA ATGAGCCAAC TGCTCTGCT
 541  ATTGCTTACG GCTTAGACAA AAAGGTTGGA GCAGAAAGAA ACGTGCTCAT CTTTGACCTG
 601  GGAGGTGGCA CTTTTGATGT GTCAATCCTC ACTATTGAGG ATGGAATCTT TGAGGTCAAG
 661  TCTACAGCTG GAGACACCCA CTTGGGGTGA GAAGATTTTG ACAACCGAAT GGTCAACCAT
 721  TTTATTGCTG AGTTTAAGCG CAAGCATAAG AAGGACATCA GTGAGAACAA GAGAGCTGTA
 781  AGACGCCTCC GTACTGCTTG TGAACGTGCT AAGCGTACCC TCTCTTCCAG CACCCAGGCC
 841  AGTATTGAGA TCGATTCTCT CTATGAAGGA ATCGACTTCT ATACCTCCAT TACCCGTGCC
 901  CGATTTGAAG AACTGAATGC CGACCTGTTC CGTGGCACCC TGGACCCAGT AGAGAAAGCC
 961  CTTCGAGATG CCAAACTAGA CAAGTCACAG ATTCATGATA TTGTCCTGGT TGGTGGTTCT
1021  ACTCGTATCC CCAAGATTCA GAAGCTTCTC CAAGACTTCT TCAATGGAAA AGAACTGAAT
```

FIG. 14B-2

```
1081  AAGAGCATCA ACCCTGATGA AGCTGTTGCT TATGGTGCAG CTGTCCAGGC AGCCATCTTG
1141  TCTGGAGACA AGTCTGAGAA TGTTCAAGAT TGCTGCTCT  ACTGTCCTCA TCCTCTTTCC
1201  CTTGGTATTG AAACTGCTGG TGGAGTCATG TCAAGCGTAA TGGATGTCAC TACCACCATT
1261  CCTACCAAGC AGACACAGAC CTTCACTACC ACCAGCCTGG TGTGCTTATT
1321  CAGGTTTATG AAGGCGAGCG TGCCATGACA AAGGATAACA ACCTGCTTGG CAAGTTTGAA
1381  CTCACAGGCA TACCTCCTGC ACCCCGAGGT GTTCCTCAGA TTGAAGTCAC TTTTGACATT
1441  GATGCCAATG GTATACTCAA TGTCTCTGCT GTGGACAAGA GTACGGGAAA AGAGAACAAG
1501  ATTACTATCA CTAATGACAA GGGCCGTTTG AGCAAGGAAG ACATTGAACG TATGGTCCAG
1561  GAAGCTGAGA AGTACAAAGC TGAAGATGAG AAGCAGAGGG ACAAGGTGTC ATCCAAGAAT
1621  TCACTTGAGT CCTATGCCTT CAACATGAAA GCAACTGTTG AAGATGAGAA ACTTCAAGGC
1681  AAGATTAACG ATGAGGACAA ACAGAAGATT CTGGACAAGT GTAATGAAAT TATCAACTGG
1741  CTTGATAAGA ATCAGACTGC AGAAAAGGAA GAATTTGAAC ATCAACAGAA AGAGCTGGAG
1801  AAAGTTTGCA ACCCCATCAT CACCAAGCTG TACCAGAGTG CAGGAGGCAT GCCAGGAGGA
1861  ATGCCTGGGG GATTTCCTGG TGGTGGAGCT CCCTCCCTCTG GTGGTGCTTC CTCAGGGCCC
1921  ACCATTGAAG AGGTTGATTA A
```

FIG. 14B-3

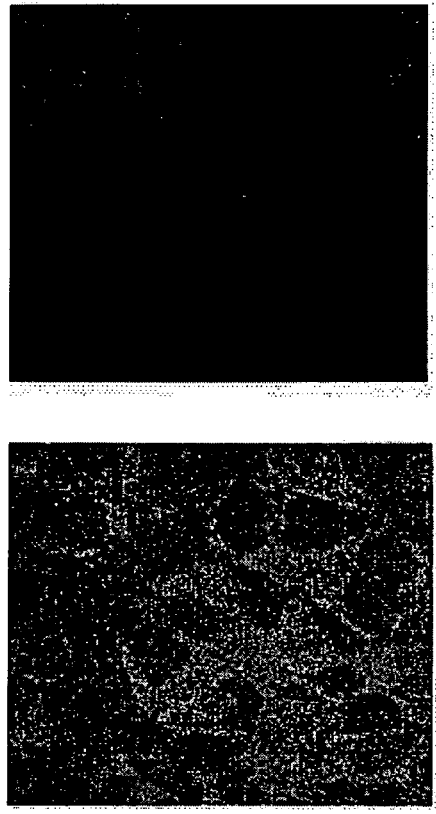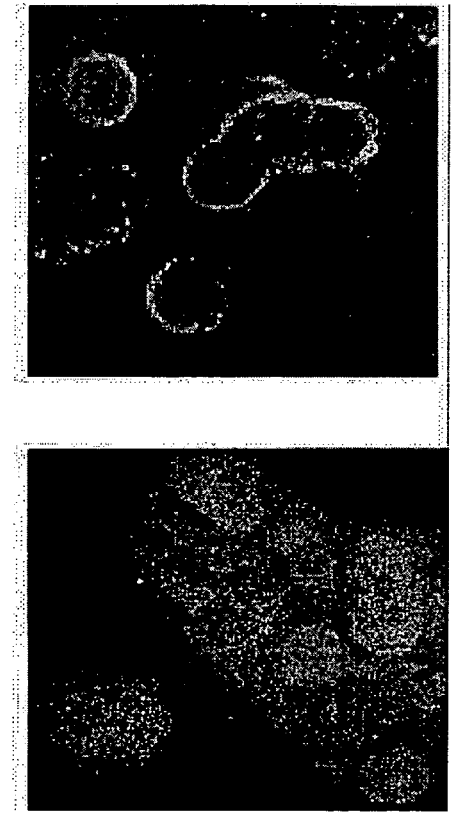
FIG. 16

SEQUENCE LISTING

<160> NUMBER OF SEQ ID NOS: 27

<210> SEQ ID NO 1
<211> LENGTH: 646
<212> TYPE: PRT
<213> ORGANISM: Homo sapiens

<400> SEQUENCE: 1

```
Met Ser Lys Gly Pro Ala Val Gly Ile Asp Leu Gly Thr Thr Tyr Ser
 1               5                  10                  15

Cys Val Gly Val Phe Gln His Gly Lys Val Glu Ile Ile Ala Asn Asp
             20                  25                  30

Gln Gly Asn Arg Thr Thr Pro Ser Tyr Val Ala Phe Thr Asp Thr Glu
         35                  40                  45

Arg Leu Ile Gly Asp Ala Ala Lys Asn Gln Val Ala Met Asn Pro Thr
     50                  55                  60

Asn Thr Val Phe Asp Ala Lys Arg Leu Ile Gly Arg Arg Phe Asp Asp
 65                  70                  75                  80

Ala Val Val Gln Ser Asp Met Lys His Trp Pro Phe Met Val Val Asn
                 85                  90                  95

Asp Ala Gly Arg Pro Lys Val Gln Val Glu Tyr Lys Gly Glu Thr Lys
            100                 105                 110
```

```
Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
        130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ile Ala Tyr Gly Leu Asp Lys Lys Val Gly Ala Glu
                180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
        210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
        260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
        290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
                340                 345                 350

Phe Phe Asn Gly Lys Glu Leu Asn Lys Ser Ile Asn Pro Asp Glu Ala
        355                 360                 365

Val Ala Tyr Gly Ala Ala Val Gln Ala Ala Ile Leu Ser Gly Asp Lys
        370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Lys Phe Glu Leu Thr Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
        500                 505                 510

Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
```

```
                530                535                540
Tyr Ala Phe Asn Met Lys Ala Thr Val Glu Asp Glu Lys Leu Gln Gly
545                550                555                560

Lys Ile Asn Asp Glu Asp Lys Gln Lys Ile Leu Asp Lys Cys Asn Glu
                565                570                575

Ile Ile Asn Trp Leu Asp Lys Asn Gln Thr Ala Glu Lys Glu Glu Phe
                580                585                590

Glu His Gln Gln Lys Glu Leu Glu Lys Val Cys Asn Pro Ile Ile Thr
        595                600                605

Lys Leu Tyr Gln Ser Ala Gly Gly Met Pro Gly Gly Met Pro Gly Gly
        610                615                620

Phe Pro Gly Gly Gly Ala Pro Pro Ser Gly Gly Ala Ser Ser Gly Pro
625                630                635                640

Thr Ile Glu Glu Val Asp
                645

<210> SEQ ID NO 2
<211> LENGTH: 1941
<212> TYPE: DNA
<213> ORGANISM: Homo sapiens

<400> SEQUENCE: 2
atgtccaagg gacctgcagt tggtattgat cttggcacca cctactcttg tgtgggtgtt       60
ttccagcacg gaaagtcgga gataattgcc aatgatcagg gaaaccgaac cactccaagc      120
tatgtcgcct ttacggacac tgaacggttg atcggtgatg ccgcaaagaa tcaagttgca      180
atgaacccca ccaacacagt ttttgatgcc aaacgtctga ttggacgcag atttgatgat      240
gctgttgtcc agtctgatat gaaacattgg ccctttatgg tggtgaatga tgctggcagg      300
cccaaggtcc aagtagaata caagggagag accaaaagct tctatccaga ggaggtgtct      360
tctatggttc tgacaaagat gaaggaaatt gcagaagcct accttgggaa gactgttacc      420
aatgctgtgg tcacagtgcc agcttacttt aatgactctc agcgtcaggc taccaaagat      480
gctggaacta ttgctggtct caatgtactt agaattatta tgagccaac tgctgctgct       540 attgcttacg gcttagacaa aaaggttgga gcagaaagaa acgtgctcat ctttgacctg      600
ggaggtggca cttttgatgt gtcaatcctc actattgagg atggaatctt tgaggtcaag      660
tctacagctg agacacccca cttgggtgga aagattttg acaaccgaat ggtcaaccat       720
tttattgctg agtttaagcg caagcataag aaggacatca gtgagaacaa gagagctgta      780
agacgcctcc gtactgcttg tgaacgtgct aagcgtaccc tctcttccag cacccaggcc      840
agtattgaga tcgattctct ctatgaagga tcgacttct ataccctccat tacccgtgcc       900 cgatttgaag aactgaatgc tgacctgttc cgtggcaccc tggacccagt agagaaagcc      960
cttcgagatg ccaaactaga caagtcacag attcatgata ttgtcctggt tggtggttct     1020
actcgtatcc ccaagattca gaagcttctc caagacttct caatggaaa agaactgaat      1080 aagagcatca accctgatga agctgttgct tatggtgcag ctgtccaggc agccatcttg     1140
tctggagaca agtctgagaa tgttcaagat tgctgctct tggatgtcac tcctctttcc      1200
cttggtattg aaactgctgg tggagtcatg actgtcctca tcaagcgtaa taccaccatt     1260
cctaccaagc agacacagac cttcactacc tattctgaca ccagcctgg tgtgcttatt      1320 caggtttatg aaggcgagcg tgccatgaca aaggataaca acctgcttgg caagtttgaa     1380
ctcacaggca tacctcctgc accccgaggt gttcctcaga ttgaagtcac ttttgacatt     1440
```

```
gatgccaatg gtatactcaa tgtctctgct gtggacaaga gtacgggaaa agagaacaag    1500
attactatca ctaatgacaa gggccgtttg agcaaggaag acattgaacg tatggtccag    1560
gaagctgaga agtacaaagc tgaagatgag aagcagaggg acaaggtgtc atccaagaat    1620
tcacttgagt cctatgcctt caacatgaaa gcaactgttg aagatgagaa acttcaaggc    1680
aagattaacg atgaggacaa acagaagatt ctggacaagt gtaatgaaat tatcaactgg    1740
cttgataaga atcagactgc tgagaaggaa gaatttgaac atcaacagaa agagctggag    1800
aaagtttgca accccatcat caccaagctg taccagagtg caggaggcat gccaggagga    1860
atgcctgggg gatttcctgg tggtggagct cctcccctctg gtggtgcttc ctcagggccc    1920
accattgaag aggttgatta a                                              1941
```

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Val Asn His Phe Ile Ala Glu Phe Lys
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Glu Glu Leu Asn Ala Asp Leu Phe Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Val Asn His Phe Ile Ala Glu Phe Lys Arg
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Arg Phe Glu Glu Leu Asn Ala Asp Leu Phe Arg
 1               5                  10

<210> SEQ ID NO 7
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 7

Thr Thr Pro Ser Tyr Val Ala Phe Thr Asp Thr Glu Arg
 1               5                  10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Thr Ala Gly Asp Thr His Leu Gly Gly Glu Asp Phe Asp Asn Arg
 1               5                  10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ile Asn Glu Pro Thr Ala Ala Ala Ile Ala Tyr Gly Leu Asp Lys
 1               5                  10                  15

Lys

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gln Val Ala Met Asn Pro Thr Asn Thr Val Phe Asp Ala Lys Arg
 1               5                  10                  15

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Asp Lys Ser Gln Ile His Asp Ile Val Leu Val Gly Gly Ser Thr
 1               5                  10                  15

Arg

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Asp Asn Asn Leu Leu Gly Lys Phe Glu Leu Thr Gly Ile Pro Pro Ala
  1               5                  10                  15

Pro Arg
```

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Thr Val Thr Asn Ala Val Val Thr Val Pro Ala Tyr Phe Asn Asp Ser
  1               5                  10                  15

Gln Arg
```

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Gln Thr Gln Thr Phe Thr Thr Tyr Ser Asp Asn Gln Pro Gly Val Leu
  1               5                  10                  15

Ile Gln Val Tyr Glu Gly Glu Arg
                 20
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Asp Ala Gly Thr Ile Ala Gly Leu Asn Val Leu Arg
  1               5                  10
```

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Phe Glu Glu Leu Asn Ala Asp Leu Phe Arg
  1               5                  10
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Met Val Asn Arg Phe Ile Ala Glu Phe Lys Arg
```

```
<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Arg Phe Glu Glu Ile Asn Ala Asp Leu Phe Arg
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Thr Pro Ser Tyr Val Ala Phe Thr Asp Thr Glu Arg
 1               5                  10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Thr Ala Gly Asp Thr His Leu Gly Gly Glu Asp Phe Asp Asn Arg
 1               5                  10                  15

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Asp Lys Ser Gln Thr His Asp Ile Val Leu Val Gly Gly Ser Thr
 1               5                  10                  15

Arg

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Thr Leu Asp Pro Val Glu Lys Ala Leu Arg Asp Ala Lys
 1               5                  10

<210> SEQ ID NO 23
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 23

Thr Val Thr Asn Ala Val Val Thr Val Pro Ala Tyr Phe Asn Asp Ser
 1               5                  10                  15

Gln Arg

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Val Gln Phe Ala Glu Lys Tyr Lys Ala Glu Asp Glu Lys Gln Arg
 1               5                  10                  15

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Gln Val Ala Ala Met Asn Pro Thr Asn Thr Val Phe Asp Ala Lys
 1               5                  10                  15

Arg

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Thr Gln Thr Phe Thr Thr Tyr Ser Asp Asn Gln Pro Gly Val Leu
 1               5                  10                  15

Ile Gln Val Tyr Glu Gly Glu Arg
            20

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ser Leu Glu Ser Tyr Ala Phe Asn Met Lys Ala Thr Val Glu Asp
 1               5                  10                  15

Glu Lys
```

HSC70 DIRECTED DIAGNOSTICS AND THERAPEUTICS FOR MULTIDRUG RESISTANT NEOPLASTIC DISEASE

This Application claims the benefit of priority to U.S. Provisional Application No. 60/438,012, filed Jan. 3, 2003, the specification of which is incorporated by reference in its entirety.

FIELD OF THE INVENTION

This invention relates to the field of diagnostics and therapeutics. In particular, this invention relates to the detection and treatment of neoplastic and/or damaged cells and, in addition, to the detection and treatment of multidrug resistant neoplastic and/or damaged cells.

1. BACKGROUND OF THE INVENTION

A commonly used treatment for diseases, such as cancer or those caused by pathogen-infection, is the administration of drugs, e.g., chemotherapeutics and antibiotics. In order to kill the diseased cells, the drug(s) must enter the cells and reach an effective dose so as to interfere with essential biochemical pathways. However, some cells evade being killed by the drug by developing resistance to it (termed "drug resistance"). Moreover, in some cases, cancer cells (also called tumor cells or neoplastic cells) and damaged cells (e.g., pathogen-infected cells), or the pathogens themselves, develop resistance to a broad spectrum of drugs, including drugs that were not originally used for treatment. This phenomenon is termed "multidrug resistance" (MDR). For example, some cancer cells in a tumor evade being killed by chemotherapeutic drugs by becoming multidrug resistant to a broad spectrum of chemotherapeutic drugs, including drugs that were not originally used for treatment.

Patient cross-resistance to different anti-microbial and anti-cancer agents, which are structurally and functionally distinct, can cause problems for both cancer patients and diseased non-cancer patients. Thus, MDR can involve cancer cells, as well as damaged, non-cancerous cells (e.g., cells infected with pathogens including virus and bacteria). The emergence of the MDR phenotype is the major cause of failure in the treatment of infectious diseases (see Davies J., *Science* 264: 375–382, 1994; Poole, K., *Cur. Opin. Microbiol.* 4: 500–5008, 2001). Similarly, the development of multidrug resistant cancer cells is the principal reason for treatment failure in cancer patients (see Gottesman, M. M., *Ann. Rev. Med.* 53: 615–627, 2000).

Multidrug resistance is multifactorial. The classic MDR mechanism involves alterations in the gene by gene amplification for the highly evolutionarily conserved plasma membrane protein (P-glycoprotein or MDR 1) that actively transports (pumps) drugs out of the cell or microorganism (Volm M. et al., *Cancer* 71: 3981–3987, 1993); Bradley and Ling, *Cancer Metastasis Rev.* 13: 223–233, 1994). Both human cancer cells and infectious bacterial pathogens may develop classic MDR via mechanisms involving overexpression of P-glycoprotein (both messenger RNA and protein) due to amplification of the gene encoding P-glycoprotein. The overexpression of P-glycoprotein mRNA or protein in MDR cancer cells or pathogen-infected cells is a biological marker for MDR. Diagnostic tests and therapeutic methods have been developed that make use of the overexpression of P-glycoprotein marker to diagnose and to treat MDR cancer and pathogen infections (Szakacs G. et al., *Pathol. Oncol. Res.* 4: 251–257, 1998). However, because various normal tissues express different amounts of P-glycoprotein, there are significant problems with side effects, as any therapy that targets P-glycoprotein on the cell surface of MDR cancer cells, would also affect those normal tissues that also have a relatively high level of P-glycoprotein expression, such as liver, kidney, stem cells, and blood-brain barrier epithelium.

"Atypical MDR" is a term used to describe MDR cancer cells or pathogens where the mechanism of multidrug resistance is unknown, novel, or different from the classic mechanism involving P-glycoprotein. For example, human lung tumors are multidrug resistant but do not have alterations in P-glycoprotein (see Cole S. P. et al., *Science* 258: 1650–1654, 1992). Rather, they express another drug transporter (the multidrug resistance associated protein or MRP1). A new mechanism of MDR was recently described that involves Lung Resistance Related Protein, which is a marker for this type of a typical MDR (Rome L. H. et al., PCT Publication No. WO9962547). Some other a typical markers for MDR include MRP5, which is a novel mammalian efflux pump for nucleoside analog drugs (see Fridland and Schuetz, PCT Publication No. WO0058471) and certain sphinogoglycolipids (see U.S. Pat. No. 6,090,565).

Heat shock proteins (HSPs), also referred to as molecular chaperones or chaperonins) are a family of highly evolutionarily conserved proteins that are normally intracellular in location (reviewed in Kusmierczyk, Martin J., *FEBS Lett* 505: 343–7, 2001). The heat shock response is thought to be an intrinsic cellular defense mechanism against external stressors from various sources, playing a crucial role in proper protein assembly, folding, and transport. Upregulation of the synthesis of heat shock proteins upon environmental stress (i.e., elevated temperature (heat shock), inflammation, heavy metals, certain drugs, amino acid analogs, environmental toxic pollutants, infections) allow cells to adapt to gradual changes in their environment and to survive otherwise lethal conditions. The events of cell stress and cell death are linked and heat shock proteins induced in response to stress appear to function at key regulatory points in the control of apoptosis (programmed cell death).

HSPs include anti-apoptotic proteins that interact with a variety of cellular proteins. Their expression level can determine the fate of the cell in response to a death stimulus, and apoptosis-inhibitory HSPs, in particular HSP27 and HSP70, may participate in carcinogenesis (reviewed in Garrido, et al., *Biochem. Biophys. Res. Commun.*, 286: 433–42, 2001). For example, HSP70 interacts with the cellular p63 tumor suppressor protein and breast cancer cells sometimes express high levels of several HSPs. Increased HSP70 is an ominous prognostic sign in node-negative breast tumors while HSP27 increases specific resistance to doxorubicin in breast cancer cell lines (Fugua, *Breast Cancer Res. Treat.*, 32: 67–71, 1994).

HSP70 is normally an intracellular protein and not found on the cell surface of non-cancerous cells (Kiang, *The Pharmacol. Ther.*, 80: 183–201, 1998). Some types of human tumors do express HSP70 on their cell surface. For example, HSP70 can be found on the cell surface of primary tumor biopsy material of carcinomas of the lung, colorectum, neurons, and pancreas, as well as liver metastases, and leukemic blasts of patients with acute myelogenous leukemia. However, SP70 is not found on the cell surface of cells from fresh biopsy material of mammary carcinomas (Hantschel, et al., *Cell Stress Chaperones*, 5: 438–42, 2000).

HSP70 genes form a large evolutionarily conserved superfamily, with multiple different similar genes encoding similar proteins (isoforms). While the classic bacterial and mammalian HSP70-type protein is inducible by stress (e.g., elevated temperature, chemicals, pathogen infection), one isoform, heat shock cognate, HSC70, is constitutively expressed (Huang, et al., *J. Biol. Chem.* 266: 7537–41, 1991). The bacterial homolog of HSC70 is DnaK. Like HSP70, HSC70 and DnaK function as molecular chaperones and are involved in mediating correct protein folding, preventing premature protein folding or aggregation, and facilitating protein translocation through the cell membrane and secretion (reviewed in Feldman, D E, Frydman J. *Curr. Opin. Struct. Biol.* 10: 13–5, 2000).

Thus, there remains a need in both humans and animals for treating, detecting, preventing, and/or reversing the development of both classical and a typical MDR phenotypes in cancer cells and damaged non-cancerous cells, regardless of how the MDR arises (e.g., naturally occurring or drug-induced). In addition, the ability to identify and to make use of reagents that identify MDR has clinical potential for improvements in the treatment, monitoring, diagnosis, and medical imaging of multidrug resistant cancer and multidrug resistant damaged cells.

2. SUMMARY OF THE INVENTION

The invention is based, in part, upon the discovery that full-length HSC70, a normally intracellular protein, is expressed in full length on the cell surface of neoplastic cells and damaged cells, and is expressed more abundantly on the cell surfaces of multidrug resistant (MDR) neoplastic cells and MDR damaged cells. Although lower levels of HSC70 are expressed on the cell surface of drug-sensitive neoplastic cells, in contrast to other cell surface MDR markers (such as P-glycoprotein), HSC70 is expressed in only negligible amounts on the cell surface of normal cells of the body. By "negligible amounts" is meant fewer than 100 molecules of HSC70 on the cell surface. Thus, the invention allows the use of binding agents, to which are bound toxins or other therapeutic or diagnostic agents, that specifically bind to HSC70 without detrimental side effects, since the only non-HSC70 cells that are being killed are drug-sensitive neoplastic cells or damaged cells; normal cells remain unharmed.

In one aspect, the invention provides a method for detecting multidrug resistance or multidrug resistance potential in a test neoplastic cell by measuring a level of cell surface-expressed HSC70 protein in the test neoplastic cell of a given origin or cell type, and comparing it to the level of cell surface-expressed HSC70 in a nonresistant neoplastic cell of the same origin or cell type. If the level of cell surface-expressed HSC70 in the test neoplastic cell is greater than the level of cell surface-expressed HSC70 in the nonresistant neoplastic cell of the same given origin or cell type, then the test neoplastic cell is multidrug resistant or has multidrug resistance potential. In certain embodiments, the level of cell surface-expressed HSC70 in the test neoplastic cell is measured by isolating a cytoplasmic membrane fraction from the cell and measuring the level of HSC70 in the cytoplasmic membrane fraction. In other embodiments, the level of cell surface-expressed HSC70 in the test neoplastic cell is measured by contacting the cell with an anti-HSC70 antibody and measuring the level of antibody bound to cell surface HSC70. For example, the level of antibody bound to cell surface HSC70 may be measured by immunofluorescence emission or radiolabel.

In certain embodiments of this aspect of the invention, the test neoplastic cell is a promyleocytic leukemia cell, a T lymphoblastoid cell, a breast epithelial cell, or an ovarian cell. In other embodiments the test neoplastic cell is a lymphoma cell, a melanoma cell, a sarcoma cell, a leukemia cell, a retinoblastoma cell, a hepatoma cell, a myeloma cell, a glioma cell, a mesothelioma cell, or a carcinoma cell. In still other embodiments of the invention, the test neoplastic cell is from a tissue such as blood, bone marrow, spleen, lymph node, liver, thymus, kidney, brain, skin, gastrointestinal tract, eye, breast, prostate, or ovary. In further embodiments, the nonresistant neoplastic (control) cell is a drug-sensistive neoplastic cell line such as HL60, NB4, CEM, HSB2 Molt4, MCF-7, MDA, SKOV-3, or 2008.

In another aspect, the invention provides a method for detecting a multidrug resistant cell or cells in a patient by administering to the patient, a HSC70 binding agent operably linked to a detectable label. The label is operably linked to the HSC70 binding agent, which specifically binds to cell surface-expressed HSC70 present on the multidrug resistant cell(s) in the patient, and is then detected, thereby locating the presence of the multidrug resistant cell(s) (if any) in the patient. In certain embodiments, the HSC70 binding agent used is an antibody or fragment thereof. In other embodiments, the HSC70 binding agent is a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In particular embodiments, the HSC70 binding agent is a natural ligand, a synthetic small molecule, a chemical, a nucleic acid, a peptide, a protein or an antibody. In other embodiments, the detectable label is a fluorophore, a chemical dye, a radioactive compound, a chemoluminescent compound, a magnetic compound, a paramagnetic compound, a promagnetic compound, an enzyme that yields a colored product, an enzyme that yields a chemoluminescent product, or an enzymes that yields a magnetic product.

In certain embodiments of this aspect, the multidrug resistant cell is a neoplastic cell. In particular embodiments, the neoplastic cell is a breast cancer cell, an ovarian cancer cell, a myeloma cancer cell, a lymphoma cancer cell, a melanoma cancer cell, a sarcoma cancer cell, a leukemia cancer cell, a retinoblastoma cancer cell, a hepatoma cancer cell, a glioma cancer cell, a mesothelioma cancer cell, or a carcinoma cancer cell. In some embodiments, the neoplastic cell is a promyleocytic leukemia cell, a T lymphoblastoid cell, a breast epithelial cell, or an ovarian cell. In particular embodiments, the patient is a human, such as a human patient that is suffering from a disease or disorder caused by the presence of the multidrug resistant cell.

In another aspect, the invention provides kits for diagnosing or detecting multidrug resistance in a test neoplastic cell. The kits include one probe for the detection of HSC70 and a second probe for the detection of another multidrug resistance marker such as nucleophosmin or vimentin. In certain embodiment, these kits of the invention include a first probe for the detection of HSC70 and a second probe for the detection of another multidrug resistance marker such as MDR1, MDR3, MRP1, MRP5, or LRP. In particular embodiments, the kits include anti-HSC70 antibody as the probe for detecting HSC70. In other embodiments, the kits include a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In further embodiments, the kits include a nucleophosmin antibody or a vimentin antibody as probes for detecting the second, non-HSC70 multidrug resistance marker. In other embodiments, the second probe may be a nucleophosmin ligand (such as protein kinase R (PKR), RNA, retinoblastoma protein, IRF-1, or a nuclear localization signals (NLS) such as the N-terminal nuclear localization signal of Rex protein) or a vimentin ligand (such as modified LDL, NLK1 protein, vimentin, desmin, glial fibrillary acidic protein, or peripherin, fimbrin, RhoA-binding kinase alpha, or protein phosphatase 2A).

In another embodiment of this aspect of the invention, the kit includes a probe that detects HSC70 present on the surface of the test neoplastic cell. In other embodiments, the kit includes a second probe that detects another (non-HSC70) marker present of the surface of the test MDR neoplastic cell. In certain embodiment, the kit includes a second probe that is an MDR1 antibody, an MDR3 antibody, an MRP1 antibody, an MRP3 antibody, or an LRP antibody.

In another aspect, the invention provides a cell surface HSC70 in situ detection probe for the detection of cell surface HSC70 in a patient. This cell surface HSC70 probe has a HSC70 binding component and a detectable label for detection in situ (e.g., a Technetium label). In some embodiments, the HSC70 binding component is an antibody.

In yet another aspect, the invention provides a cell surface HSC70-targeted agent for treating or preventing a multi-drug resistant neoplasm. This HSC70-targeted agent includes both a HSC70 binding component and a therapeutic component which act together such that the HSC70 binding component targets the therapeutic component to the multi-drug resistant neoplasm and thereby treats the multi-drug resistant neoplasm. In certain embodiments, the HSC70 binding component is an anti-HSC70 antibody. In other embodiments, the HSC70 binding component is a HSC70 ligand such as HSC70 ligand, such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In particular embodiments, the HSC70 binding component is a natural ligand, synthetic small molecule, chemical, nucleic acid, peptide or protein.

In certain useful embodiments of this aspect of the invention, the therapeutic component is a chemotherapeutic agent such as Actinomycin, Adriamycin, Altretamine, Asparaginase, Bleomycin, Busulfan, Capecitabine, Carboplatin, Carmustine, Chlorambucil, Cisplatin, Cladribine, Cyclophosphamide, Cytarabine, Dacarbazine, Dactinomycin, Daunorubicin, Docetaxel, Doxorubicin, Epoetin, Etoposide, Fludarabine, Fluorouracil, Gemcitabine, Hydroxyurea, Idarubicin, Ifosfamide, Imatinib, Irinotecan, Lomustine, Mechlorethamine, Melphalan, Mercaptopurine, Methotrexate, Mitomycin, Mitotane, Mitoxantrone, Paclitaxel, Pentostatin, Procarbazine, Taxol, Teniposide, Topotecan, Vinblastine, Vincristine, or Vinorelbine. In particular embodiments, the therapeutic component is in a liposome formulation.

In other embodiments, the therapeutic component is a radioisotope such as $^{90}$Y, $^{125}$I, $^{131}$I, $^{211}$At or $^{213}$Bi.

In still other embodiments, the therapeutic component is a toxin capable of killing or inducing the killing of the targeted multi-drug resistant neoplastic cell. Such toxins for use in the invention include Pseudomonas exotoxin, diphtheria toxin, plant ricin toxin, plant abrin toxin, plant saporin toxin, plant gelonin toxin and pokeweed antiviral protein.

In particularly useful embodiments, the HSC70 binding component of the cell surface HSC70-targeted therapeutic agent binds to the surface of the target cell, and the therapeutic element is internalized and arrests growth of the cell, compromises viability of the cell or kills the cell.

In another aspect, the invention provides a method of treating or preventing a multidrug resistant neoplasm in a subject by administering any of the cell surface HSC70-targeted therapeutic agents described above. In certain embodiments of this aspect, the neoplasm is a breast cancer, an ovarian cancer, a myeloma, a lymphoma, a melanoma, a sarcoma, a leukemia, a retinoblastoma, a hepatoma, a glioma, a mesothelioma, or a carcinoma. In further embodiments, the neoplasm is from a tissue such as blood, bone marrow, spleen, lymph node, liver, thymus, kidney, brain, skin, gastrointestinal tract, eye, breast, prostate, or ovary. In particular embodiments, the subject is a human patient, such as a human patient suffering from a disease or disorder caused by the presence of the multi-drug resistant cell.

In yet another aspect, the invention provides vaccines for treating or preventing multi-drug resistant neoplasms, comprising a HSC70 polypeptide, or HSC70 polypeptide subsequence thereof, and at least one pharmaceutically acceptable vaccine component. In certain embodiments, the HSC70 polypeptide or polypeptide subsequence is a human HSC70 polypeptide sequence having an amino acid sequence of SEQ ID NO: 1. In particular embodiments, the HSC70 polypeptide subsequence is at least eight amino acids long, and, in certain embodiments, functions as a hapten.

In certain embodiments, the vaccine formulation includes an adjuvant or other pharmaceutically acceptable vaccine component. In particular embodiments, the adjuvant is aluminum hydroxide, aluminum phosphate, calcium phosphate, oil emulsion, a bacterial product, whole inactivated bacteria, an endotoxins, cholesterol, a fatty acid, an aliphatic amine, a paraffinic compound, a vegetable oil, monophosphoryl lipid A, a saponin, or squalene.

In another aspect, the invention provides a method of treating or preventing a multidrug resistant neoplasm in a subject by administering any of the HSC70 vaccines described above. In certain embodiments of this aspect, the neoplasm to be treated is a breast cancer, an ovarian cancer, a myeloma, a lymphoma, a melanoma, a sarcoma, a leukemia, a retinoblastoma, a hepatoma, a glioma, a mesothelioma, or a carcinoma. In further embodiments, the neoplasm is from a tissue such as blood, bone marrow, spleen, lymph node, liver, thymus, kidney, brain, skin, gastrointestinal tract, eye, breast, prostate, or ovary. In particular embodiments, the subject is a human patient, such as a human patient is suffering from a disease or disorder caused by the presence of the multi-drug resistant cell.

In yet another aspect, the invention provides a method for detecting whether a test cell is neoplastic by measuring the level of cell surface-expressed HSC70 protein in the test cell of a given origin or cell type, and comparing it to the level of cell surface-expressed HSC70 in a nonneoplastic cell of the same origin or cell type. If the level of cell surface-expressed HSC70 in the test cell is greater than the level of cell surface-expressed HSC70 in the nonneoplastic cell of the same given origin or cell type, then the test cell is neoplastic.

In certain embodiments, the level of cell surface-expressed HSC70 in the test cell is measured by isolating a cytoplasmic membrane fraction from the cell and measuring the level of HSC70 in the cytoplasmic membrane fraction. In other embodiments, the level of cell surface-expressed HSC70 in the test cell is measured by contacting the cell with an anti-HSC70 antibody and measuring the level of antibody bound to cell surface HSC70. For example, the level of antibody bound to cell surface HSC70 may be measured by immunofluorescence emission or radiolabel.

In certain embodiments of this aspect of the invention, the test cell is a promyleocytic leukemia cell, a T lymphoblastoid cell, a breast epithelial cell, or an ovarian cell. In other embodiments the test cell is a lymphoma cell, a melanoma cell, a sarcoma cell, a leukemia cell, a retinoblastoma cell, a hepatoma cell, a myeloma cell, a glioma cell, a mesothelioma cell, or a carcinoma cell. In still other embodiments of the invention, the test cell is from a tissue such as blood, bone marrow, spleen, lymph node, liver, thymus, kidney, brain, skin, gastrointestinal tract, eye, breast, prostate, or ovary.

In another aspect, the invention provides a method for detecting a neoplastic cell or cells in a patient by administering to the patient, a HSC70 binding agent operably linked to a detectable label. The label is operably linked to the HSC70 binding agent, which specifically binds to cell surface-expressed HSC70 present on the neoplastic cell(s) in the patient, and is then detected, thereby locating the presence of the neoplastic cell(s) (if any) in the patient. In certain embodiments, the HSC70 binding agent used is an antibody or fragment thereof. In other embodiments, the HSC70 binding agent is a HSC70 ligand HSC70 ligand, such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In particular embodiments, the HSC70 binding agent is a natural ligand, a synthetic small molecule, a chemical, a nucleic acid, a peptide, a protein or an antibody. In other embodiments, the detectable label is a fluorophore, a chemical dye, a radioactive compound, a chemoluminescent compound, a magnetic compound, a paramagnetic compound, a promagnetic compound, an enzyme that yields a colored product, an enzyme that yields a chemoluminescent product, or an enzymes that yields a magnetic product.

In certain embodiments of this aspect, the neoplastic cell is a breast cancer cell, an ovarian cancer cell, a myeloma cancer cell, a lymphoma cancer cell, a melanoma cancer cell, a sarcoma cancer cell, a leukemia cancer cell, a retinoblastoma cancer cell, a hepatoma cancer cell, a glioma cancer cell, a mesothelioma cancer cell, or a carcinoma cancer cell. In certain embodiments, the neoplastic cell is a promyleocytic leukemia cell, a T lymphoblastoid cell, a breast epithelial cell, or an ovarian cell. In particular embodiments, the patient is a human, such as a human patient that is suffering from a disease or disorder caused by the presence of the neoplastic cell(s).

In another aspect, the invention provides kits for diagnosing or detecting a neoplasm, which include at least one probe for detecting HSC70, and at least one other probe for detecting another neoplastic marker such as nucleophosmin or vimentin. In one embodiment, the probe for detecting HSC70 is an anti-HSC70 antibody or a binding fragment thereof. In other embodiments, the probe for detecting HSC70 is an HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG).

In certain embodiments, the second probe for detecting a non-HSC70 neoplastic marker is a nucleophosmin antibody or an HSC70 antibody. In other embodiments, the second probe for detecting a non-HSC70 neoplastic marker is a nucleophosmin ligand, such as protein kinase R (PKR), RNA, retinoblastoma protein, IRF-1, or a nuclear localization signals (NLS) such as the N-terminal nuclear localization signal of Rex protein as and an HSC70 ligand. In still other embodiments, the second probe for detecting a non-HSC70 neoplastic marker is a vimentin ligand, such as modified LDL, NLK1 protein, vimentin, desmin, glial fibrillary acidic protein, or peripherin, fimbrin, RhoA-binding kinase alpha, or protein phosphatase 2A.

In particularly useful embodiments, the kit includes a first probe which detects HSC70 present on the surface of the test cell if it is neoplastic, and a second probe which detects another (non-HSC70) marker present of the surface of the test cell if it is neoplastic.

In yet another aspect, the invention provides a cell surface HSC70-targeted agent for treating a cancerous neoplastic cell growth. The cell surface HSC70-targeted agent generally includes a HSC70 binding component and a therapeutic component. The HSC70 binding component targets the therapeutic component to the neoplastic cell growth and thereby treats the cancer. The HSC70 binding component and the therapeutic component, therefore, act together such that the HSC70 binding component targets the therapeutic component to the neoplasm to treat the neoplasm.

In certain embodiments, the HSC70 binding component is an anti-HSC70 antibody. In other embodiments, the HSC70 binding component is a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In particular embodiments, the HSC70 binding component is a natural ligands, synthetic small molecules, chemicals, nucleic acids, peptides or protein.

In certain useful embodiments of this aspect of the invention, the therapeutic component is a chemotherapeutic agent such as Actinomycin, Adriamycin, Altretamine, Asparaginase, Bleomycin, Busulfan, Capecitabine, Carboplatin, Carmustine, Chlorambucil, Cisplatin, Cladribine, Cyclophosphamide, Cytarabine, Dacarbazine, Dactinomycin, Daunorubicin, Docetaxel, Doxorubicin, Epoetin, Etoposide, Fludarabine, Fluorouracil, Gemcitabine, Hydroxyurea, Idarubicin, Ifosfamide, Imatinib, Irinotecan, Lomustine, Mechlorethamine, Melphalan, Mercaptopurine, Methotrexate, Mitomycin, Mitotane, Mitoxantrone, Paclitaxel, Pentostatin, Procarbazine, Taxol, Teniposide, Topotecan, Vinblastine, Vincristine, or Vinorelbine. In particular embodiments, the therapeutic component is in a liposome formulation.

In other embodiments, the therapeutic component is a radioisotope such as $^{90}$Y, $^{125}$I, $^{131}$I, $^{211}$At or $^{213}$Bi.

In still other embodiments, the therapeutic component is a toxin capable of killing or inducing the killing of the targeted multi-drug resistant neoplastic cell. Such toxins for use in the invention include Pseudomonas exotoxin, diphtheria toxin, plant ricin toxin, plant abrin toxin, plant saporin toxin, plant gelonin toxin and pokeweed antiviral protein.

In particularly useful embodiments, the HSC70 binding component of the cell surface HSC70-targeted therapeutic agent binds to the surface of the target cell, and the therapeutic element is internalized and arrests growth of the cell, compromises viability of the cell or kills the cell.

In another aspect, the invention provides a method of treating a neoplasm in a subject by administering any of the cell surface HSC70-targeted therapeutic agents described above. In certain embodiments of this aspect, the neoplasm is a breast cancer, an ovarian cancer, a myeloma, a lymphoma, a melanoma, a sarcoma, a leukemia, a retinoblastoma, a hepatoma, a glioma, a mesothelioma, or a carcinoma. In further embodiments, the neoplasm is from a tissue such as blood, bone marrow, spleen, lymph node, liver, thymus, kidney, brain, skin, gastrointestinal tract, eye, breast, prostate, or ovary. In particular embodiments, the subject is a human patient, such as a human patient suffering from a disease or disorder caused by the presence of the neoplasm.

In yet another aspect, the invention provides vaccines for treating or preventing a neoplasm. These vaccines of the invention include a HSC70 polypeptide, or HSC70 polypeptide subsequence thereof, and at least one pharmaceutically acceptable vaccine component. In certain embodiments, the HSC70 polypeptide or polypeptide subsequence is a human HSC70 polypeptide sequence having an amino acid sequence of SEQ ID NO: 1. In particular embodiments, the HSC70 polypeptide subsequence is at least eight amino acids long, and, in certain embodiments, functions as a hapten.

In certain embodiments, the vaccine formulation includes an adjuvant or other pharmaceutically acceptable vaccine component. In particular embodiments, the adjuvant is aluminum hydroxide, aluminum phosphate, calcium phosphate, oil emulsion, a bacterial product, whole inactivated bacteria, an endotoxins, cholesterol, a fatty acid, an aliphatic amine, a paraffinic compound, a vegetable oil, monophosphoryl lipid A, a saponin, or squalene.

In another aspect, the invention provides a method of treating or preventing a neoplasm in a subject by administering any of the HSC70 vaccines described above. In certain embodiments of this aspect, the neoplasm to be treated is a breast cancer, an ovarian cancer, a myeloma, a lymphoma, a melanoma, a sarcoma, a leukemia, a retinoblastoma, a hepatoma, a glioma, a mesothelioma, or a carcinoma. In further embodiments, the neoplasm is from a tissue such as blood, bone marrow, spleen, lymph node, liver, thymus, kidney, brain, skin, gastrointestinal tract, eye, breast, prostate, or ovary. In particular embodiments, the subject is a human patient, such as a human patient is suffering from a disease or disorder caused by the presence of the multi-drug resistant cell.

In still another aspect, the invention provides a method for detecting damage (e.g., pathogen infection) in a test cell by measuring a level of cell surface-expressed HSC70 protein in the test cell of a given origin or cell type, and comparing it to the level of cell surface-expressed HSC70 in a non-damaged cell of the same origin or cell type. If the level of cell surface-expressed HSC70 in the test cell is greater than the level of cell surface-expressed HSC70 in the nondamaged cell of the same given origin or cell type, then the test cell is damaged (e.g., infected).

In certain embodiments, the damaged cell is infected with a pathogen. In particular embodiments, the level of cell surface-expressed HSC70 in the test cell is measured by isolating a cytoplasmic membrane fraction from the cell and measuring the level of HSC70 in the cytoplasmic membrane fraction. In certain embodiments, the level of cell surface-expressed HSC70 in the test cell is measured with an anti-HSC70 antibody. In particular embodiments, the anti-HSC70 antiobody measures the level of cell surface HSC70 present on the intact test cell. For example, the level of antibody bound to cell surface HSC70 may be measured by immunofluorescence emission or radiolabel.

In particular embodiments, damaged cell is infected with a pathogen that is a virus, a bacterium or a parasite. In certain embodiments, the pathogen is a virus such as HIV, West Nile virus or Dengue virus. In other embodiments, the pathogen is a bacterium such as a Mycobacteria, Rickettsia, or Chlamydia. In still other embodiments, the pathogen is a parasite such as a Plasmodium, Leishmania, or Taxoplasma.

In certain other embodiments, the test cell is from a tissue such as blood, bone marrow, spleen, lymph node, liver, thymus, kidney, brain, skin, gastrointestinal tract, eye, breast, prostate, or ovary. In particular embodiments, the test cell is from a human. In particular embodiments, the human patient is suffering from a disease or disorder caused by the presence of the pathogen infected cell.

In another aspect, the invention provides a method for detecting a damaged (e.g., pathogen-infected) cell or cells in a patient by administering to the patient, a HSC70 binding agent operably linked to a detectable label. The label is operably linked to the HSC70 binding agent, which specifically binds to cell surface-expressed HSC70 present on the damaged (e.g., pathogen-infected) cell(s) in the patient, and is then detected, thereby locating the presence of the damaged (e.g., pathogen-infected) (if any) in the patient. In certain embodiments, the HSC70 binding agent used is an antibody or fragment thereof. In other embodiments, the HSC70 binding agent is a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In particular embodiments, the HSC70 binding agent is a natural ligand, a synthetic small molecule, a chemical, a nucleic acid, a peptide, a protein or an antibody. In other embodiments, the detectable label is a fluorophore, a chemical dye, a radioactive compound, a chemoluminescent compound, a magnetic compound, a paramagnetic compound, a promagnetic compound, an enzyme that yields a colored product, an enzyme that yields a chemoluminescent product, or an enzyme that yields a magnetic product.

In another aspect, the invention provides kits for diagnosing or detecting pathogen infection in a test cell. The kits include one probe for the detection of HSC70 and a second probe for the detection of another marker of damage (e.g., pathogen infection) such as nucleophosmin or vimentin. In particular embodiments, the kits include anti-HSC70 antibody as the probe for detecting HSC70. In other embodiments, the kits include a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In further embodiments, the kits include a nucleophosmin antibody or an HSC70 antibody as probes for detecting the second, non-HSC70 damage (e.g., pathogen infection) marker. In other embodiments, the second probe may be a nucleophosmin ligand (such as protein kinase R (PKR), RNA, retinoblastoma protein, IRF-1, or a nuclear localization signals (NLS) such as the N-terminal nuclear localization signal of Rex protein), or a vimentin ligand (such as modified LDL, NLK1 protein, vimentin, desmin, glial fibrillary acidic protein, or peripherin, fimbrin, RhoA-binding kinase alpha, or protein phosphatase 2A). In certain embodiments, the HSC70 binding component is a natural ligand, a synthetic small molecule, a chemical, a nucleic acid, a peptide, a protein, or an antibody or fragments thereof.

In yet another aspect, the invention provides cell surface HSC70-targeted agents for treating infection by a pathogen. The HSC70-targeted agent includes a HSC70 binding component and a therapeutic component. The HSC70 binding component targets the therapeutic component to the pathogen infected cell and thereby treats the infection. In certain embodiments, the HSC70 binding agent is an anti-HSC70 antibody. In other embodiments the HSC70 binding component is a HSC70 ligand such as Alzheimer's tau protein, BAG-1, small glutamine-rich tetratricopeptide repeat-containing protein (SGT), (aa 642–658) of rotavirus VP5 protein, auxilin, or the immunosuppressant 5-deoxyspergualin (DSG). In certain embodiments, the HSC70 binding component is a natural ligand, a synthetic small molecule, a chemical, a nucleic acid, a peptide, a protein, or an antibody or fragments thereof.

In particular embodiments, the therapeutic component is an antibacterial, antiviral or antiparasitic agent. In certain embodiments, the HSC70 binding component binds to the surface of the target cell and the therapeutic element is internalized and arrests growth of the pathogen, compromises viability of the pathogen or kills the pathogen-infected cell.

In yet another aspect, the invention provides vaccines for treating or preventing infection by a pathogen. These vaccines include a HSC70 polypeptide or polypeptide subsequence at least one pharmaceutically acceptable vaccine component. In certain embodiments, the HSC70 polypeptide is a human HSC70 polypeptide sequence having an amino acid sequence of SEQ ID NO: 1. In particular embodiments, the HSC70 polypeptide subsequence is at least eight amino acids long, and, in certain embodiments, functions as a hapten.

In certain embodiments, the vaccine formulation includes an adjuvant or other pharmaceutically acceptable vaccine component. In particular embodiments, the adjuvant is aluminum hydroxide, aluminum phosphate, calcium phosphate, oil emulsion, a bacterial product, whole inactivated bacteria, an endotoxins, cholesterol, a fatty acid, an aliphatic amine, a paraffinic compound, a vegetable oil, monophosphoryl lipid A, a saponin, or squalene.

In another aspect, the invention provides a method of treating or preventing an infection in a subject by administering any of the HSC70 vaccines described above. In certain embodiments of this aspect, the subject is a human patient. In particular embodiments the human patient is suffering from a disease or disorder caused by the presence of infection. In certain embodiments, the infection is in a tissue such as blood, bone marrow, spleen, lymph node, liver, thymus, kidney, brain, skin, gastrointestinal tract, eye, breast, prostate or ovary.

3. BRIEF DESCRIPTION OF THE DRAWINGS

Figure 1A:
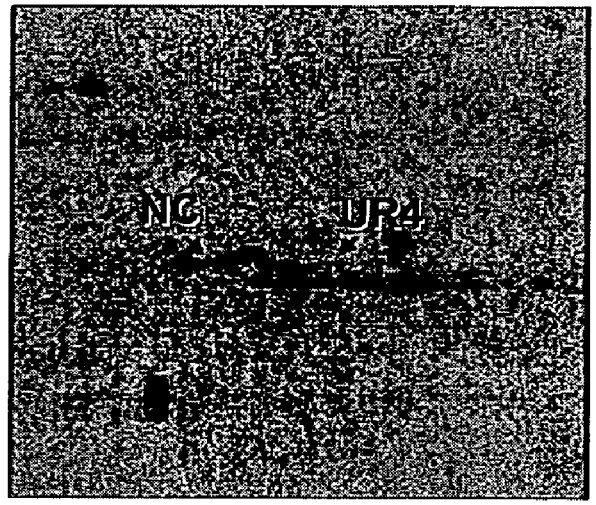
FIG. 1A is a photographic representation of a 2-D gel analysis from CEM cells from plasma membrane cell extracts.
Figure 1B:
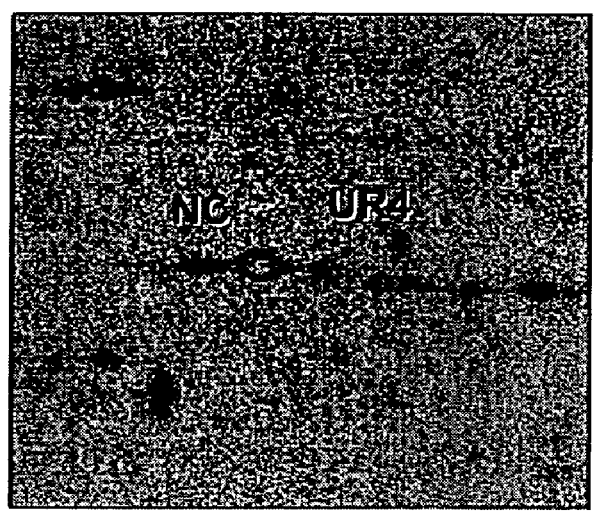
FIG. 1B is a photographic representation of a 2-D gel analysis from multidrug resistant CEM/VLB cells from plasma membrane cell extracts.

FIGS. 2A and B are representations of printed reports from MALDI mass spectrum analysis of the spots corresponding to isoform 2 (NC) from the 2-D gel shown in FIG. 1B.

FIG. 2C is a schematic representation of sequence data obtained for 12 tryptic peptides (SEQ ID NOS 3–14, respectively in order of appearance).

FIG. 3 is a schematic representation of the amino acid sequence of HSC70 protein (SEQ ID NO: 1) showing tryptic peptide sequences from MALDI analysis from CEM/VLB cells.

Figure 4A:
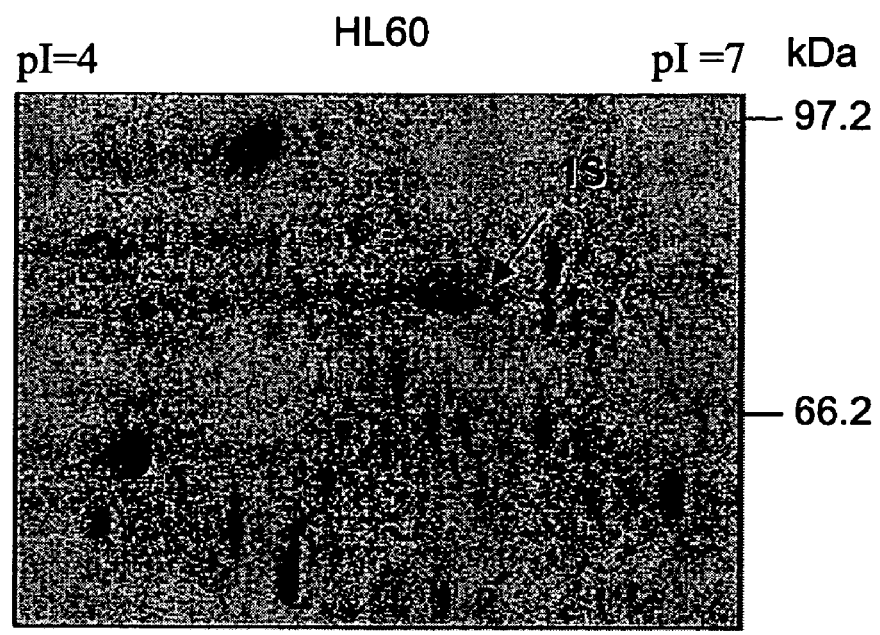

FIG. 4A is a photographic representation of a 2-D gel of Gelcode Blue stained biotinylated HL60 total cell extract.

Figure 4B:
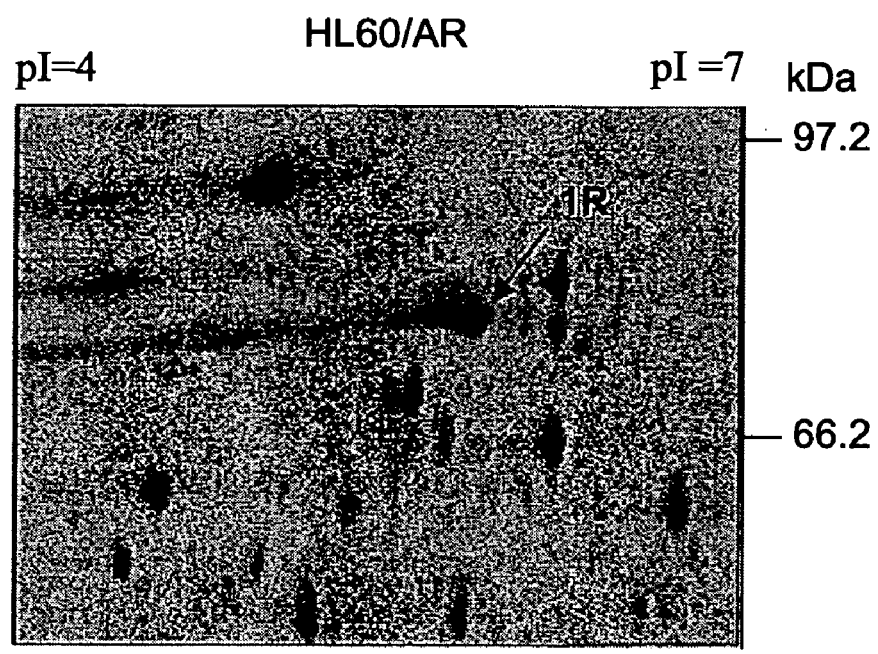

FIG. 4B is a photographic representation of a 2-D gel of GelCode Blue stained biotinylated HL60/AR total cell extract.

FIGS. 5A and B are representations of printed reports from MALDI mass spectrum analysis of the spots corresponding to HSC70 from the 2-D gel spots isolated from HL60/AR cells.

FIG. 5C is a schematic representation of sequence data obtained for 13 tryptic peptides (SEQ ID NOS 15–27, respectively in order of appearance).

FIG. 6 is a schematic representation of the amino acid sequence of HSC70 protein (SEQ ID NO: 1) showing tryptic peptide sequences from MALDI analysis from HL60/AR cells.

Figure 7:
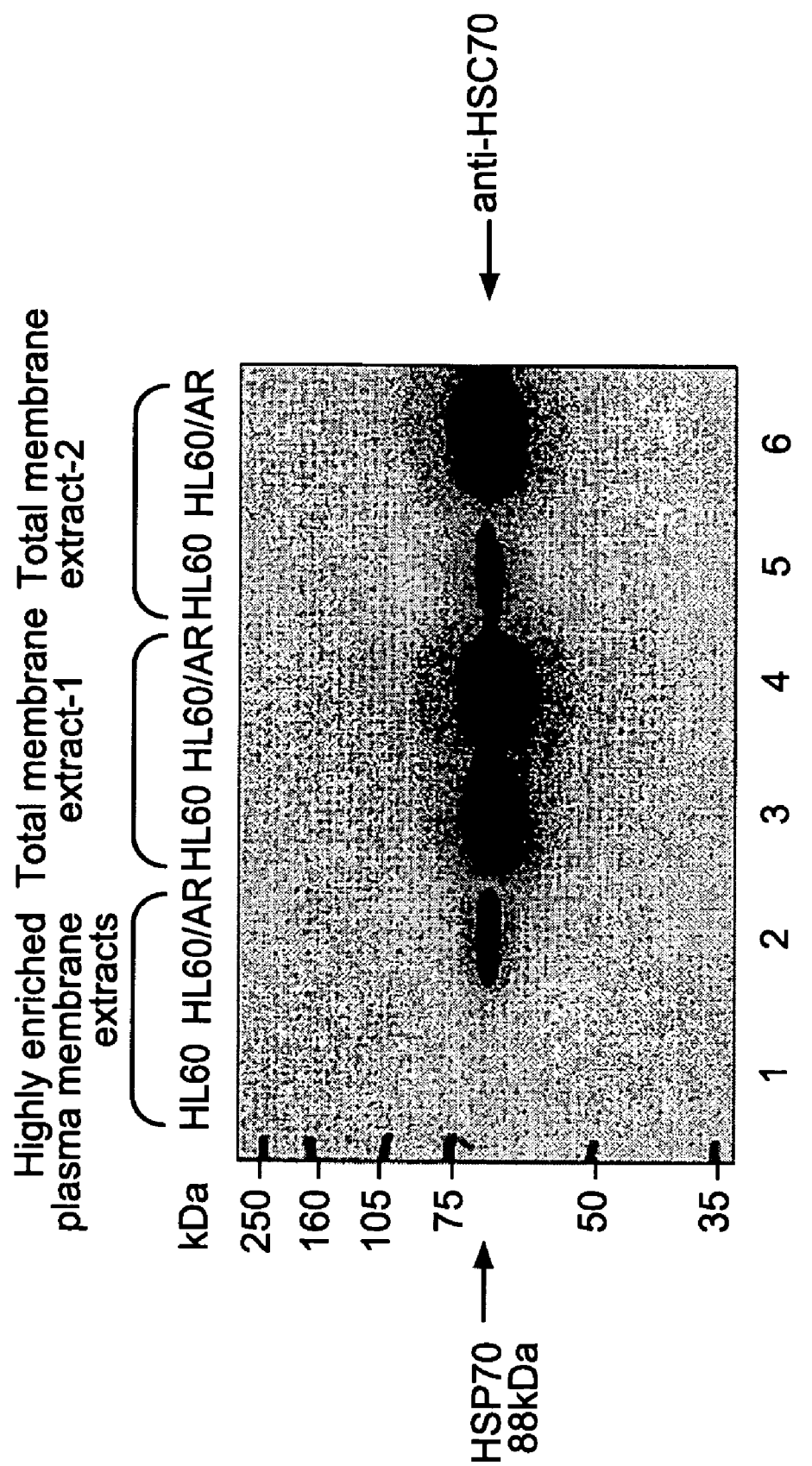

FIG. 7 is a photographic representation of SDS-PAGE resolved membrane fractions from HL60 and HL60/AR cells immunoblotted with a specific anti-HSC70 rat monoclonal antibody.

Figure 8A:
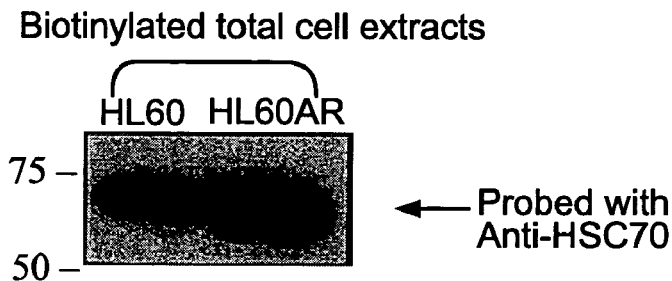

FIG. 8A is a photographic representation of Western blotting analysis of 10% SDS-polyacrylamide gel resolved biotinylated total cell extracts prepared from HL60 and HL60/AR cells and probed with anti-HSC70 antibody.

Figure 8B:
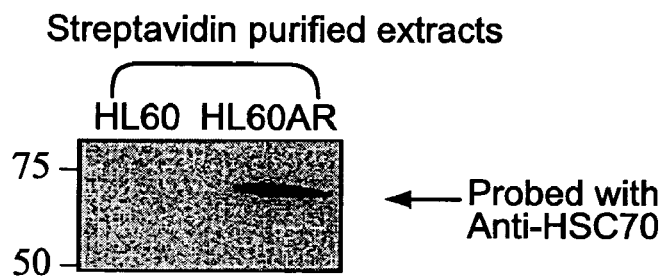

FIG. 8B is a photographic representation of Western blotting analysis of 10% SDS polyacrylamide gel resolved streptavidin purified extracts prepared from streptavidin purified total cell extracts from HL60 and HL60/AR cells and probed with anti-HSC70 antibody.

Figure 8C:
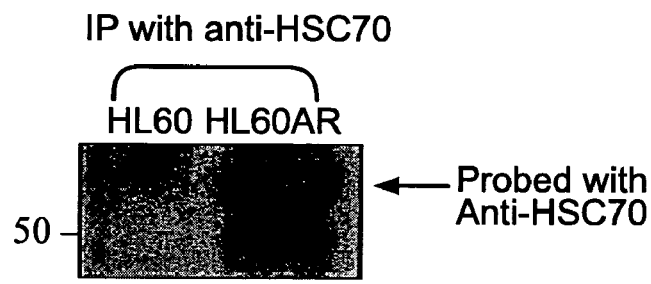

FIG. 8C is a photographic representation of Western blotting analysis of 10% SDS polyacrylamide gel resolved immunoprecipitates of surface biotinylated total cell extracts from HL60 and HL60/AR cells containing HSC70 and probed with anti-HSC70 antibody.

Figure 8D:
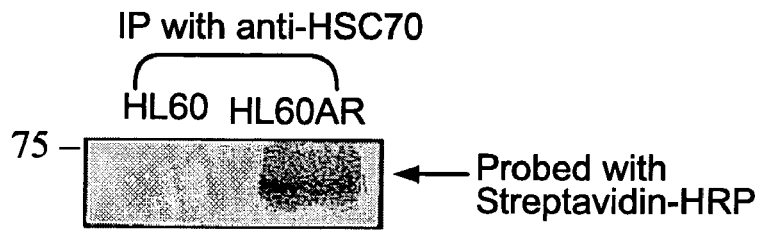

FIG. 8D is a photographic representation of Western blotting analysis of 10% SDS polyacrylamide gel resolved immunoprecipitates of surface biotinylated total cell extracts from HL60 and HL60/AR cells containing HSC70 and probed with streptavidin-HRP.

Figure 9A:
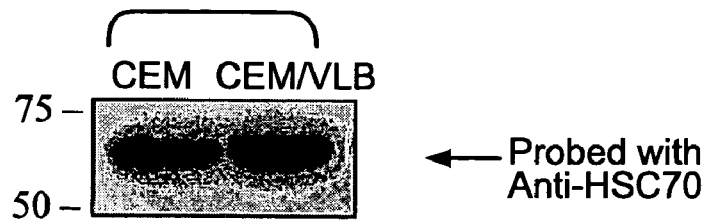

FIG. 9A is a photographic representation of Western blotting analysis of 10% SDS-polyacrylamide gel resolved biotinylated total cell extracts prepared from CEM and CEM/VLB cells and probed with anti-HSC70 antibody.

Figure 9B:
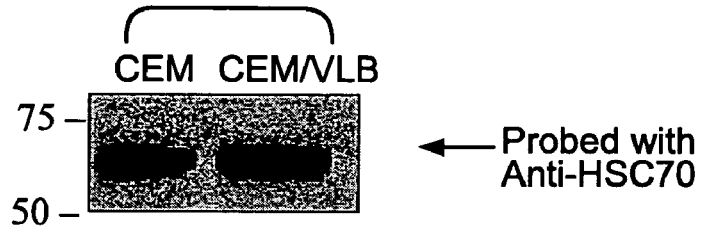

FIG. 9B is a photographic representation of Western blotting analysis of 10% SDS polyacrylamide gel resolved streptavidin purified extracts prepared from surface biotinylated total cell extracts from CEM and CEM/VLB cells and probed with anti-HSC70 antibody.

Figure 9C:
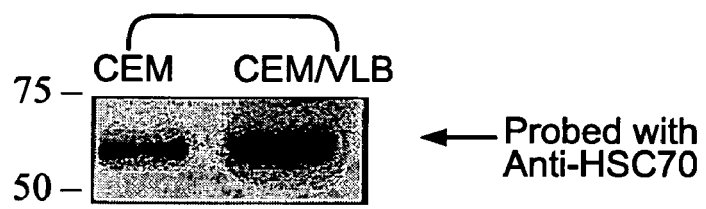

FIG. 9C is a photographic representation of Western blotting analysis of 10% SDS polyacrylamide gel resolved immunoprecipitates of surface biotinylated total cell extracts from CEM and CEM/VLB cells containing HSC70 and probed with anti-HSC70 antibody.

Figure 9D:
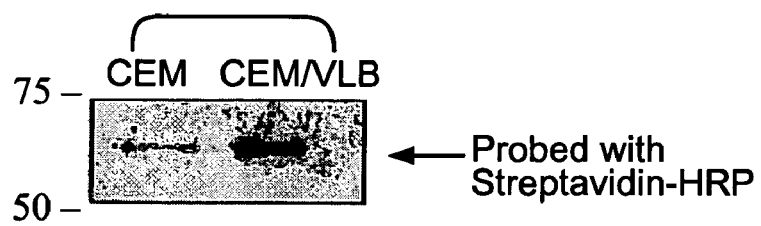

FIG. 9D is a photographic representation of Western blotting analysis of 10% SDS polyacrylamide gel resolved immunoprecipitates of surface biotinylated total cell extracts from CEM and CEM/VLB cells containing HSC70 and probed with streptavidin-HRP.

Figure 10A:
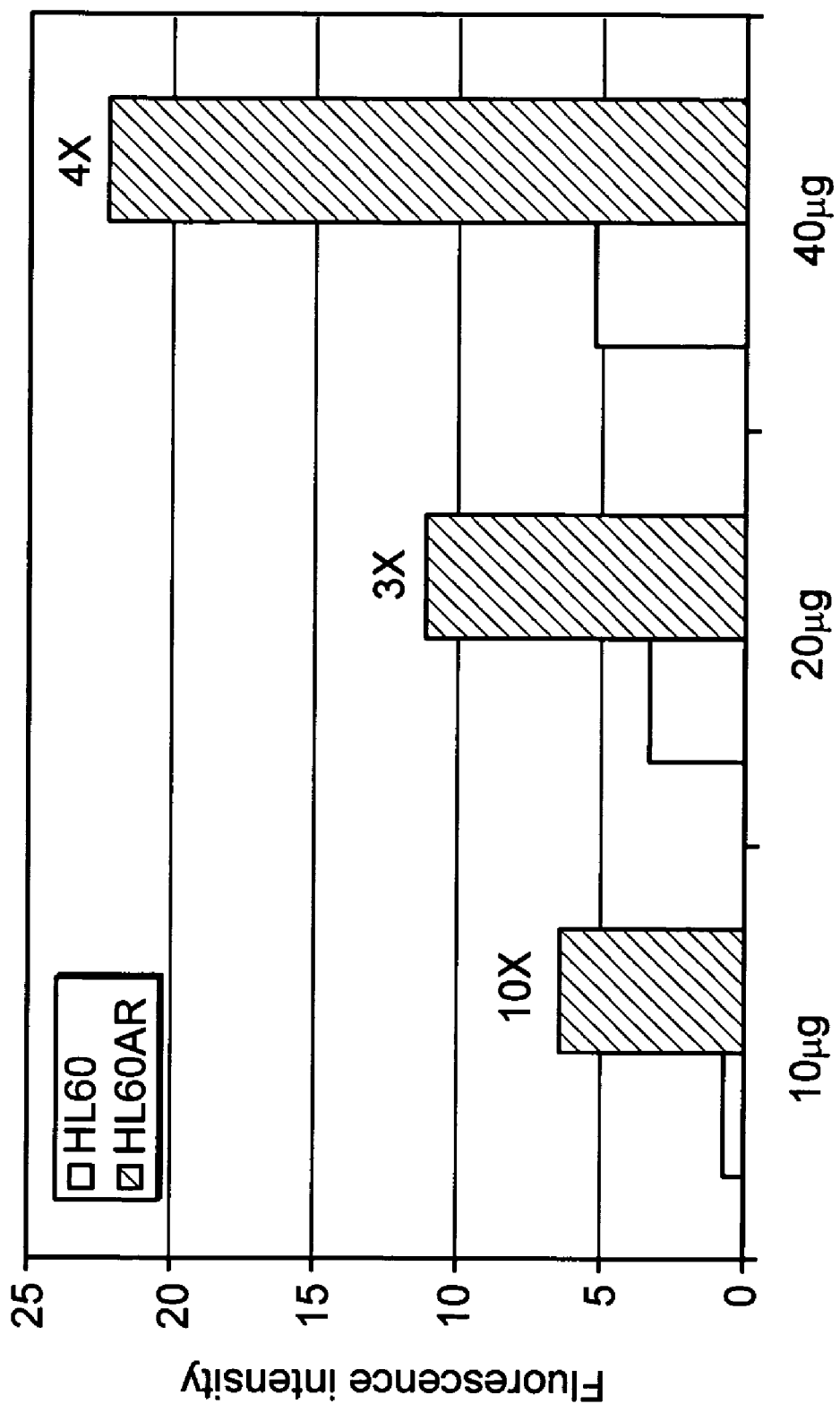

FIG. 10A is a graphic representation showing the results of FACS analysis for the surface expression of HSC70 using 10 μg, 20 μg and 40 μg monoclonal anti-HSC70 antibody as primary antibody on HL60 and HL60/AR cell lines.

Figure 10B:
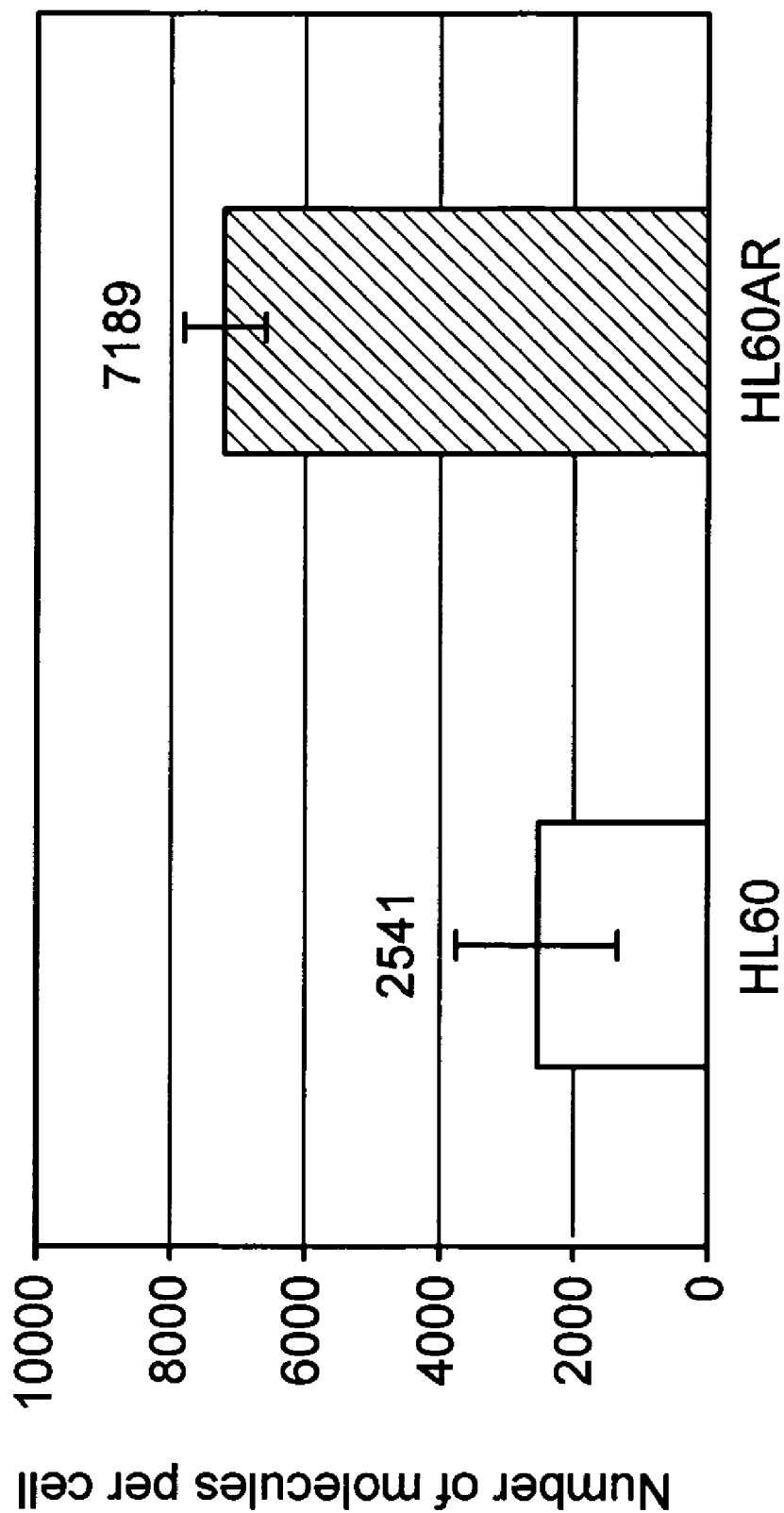

FIG. 10B is a graphic representation showing the results of FACS analysis for the surface expression of HSC70 at saturating amounts of mouse monoclonal anti-HSC70 antibody on HL60 and HL60/AR cell lines.

Figure 11A:
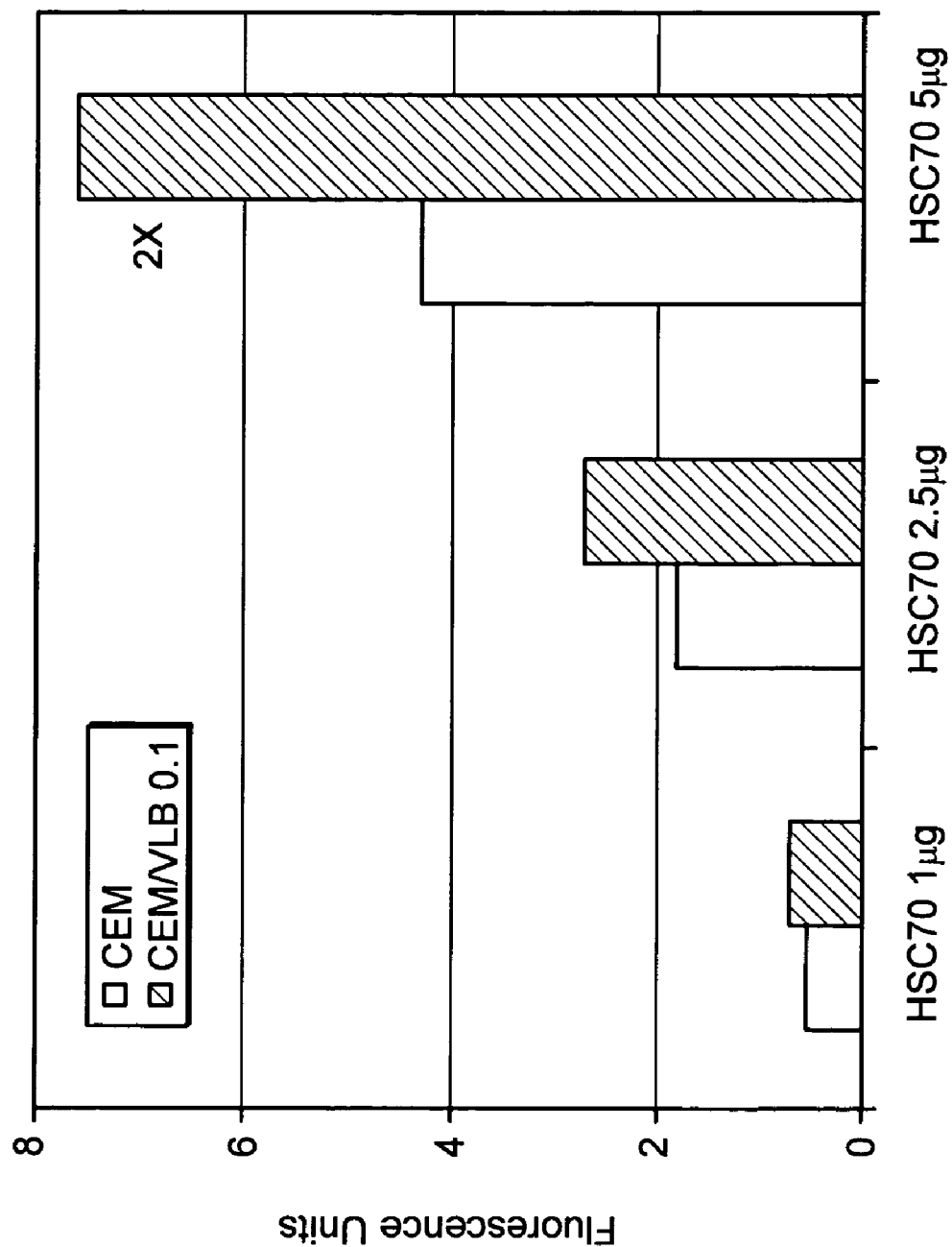

FIG. 11A is a graphic representation showing the results of FACS analysis for the surface expression of HSC70 on CEM and multidrug resistant CEM/VLB cell lines using 1 μg, 2.5 μg and 5 μg of anti-HSC70 as primary antibody.

Figure 11B:
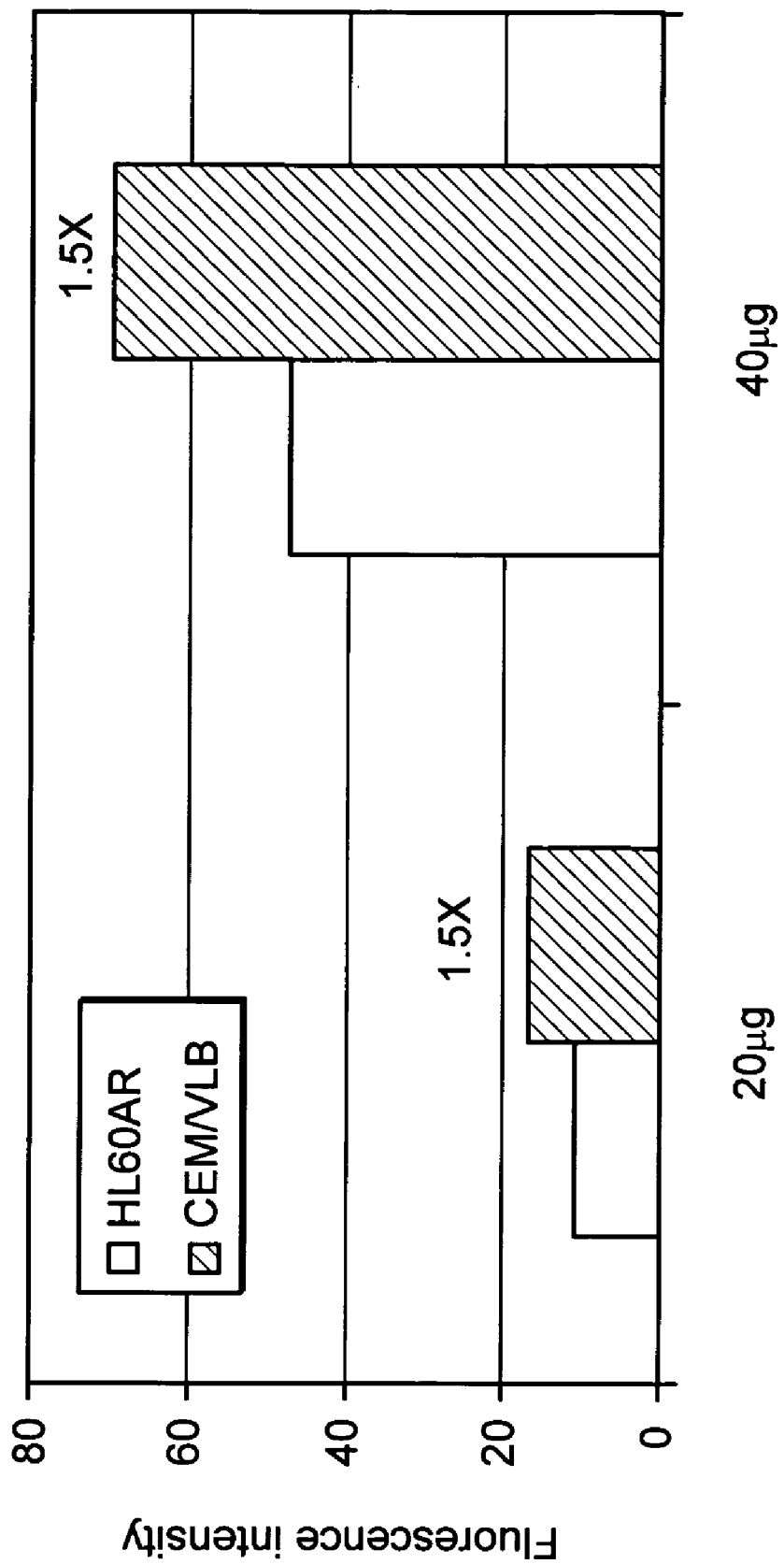

FIG. 11B is a graphical representation showing the results of FACS analysis for the surface expression of HSC70 on HL60/AR and CEM/VLB cell lines.

Figure 11C:
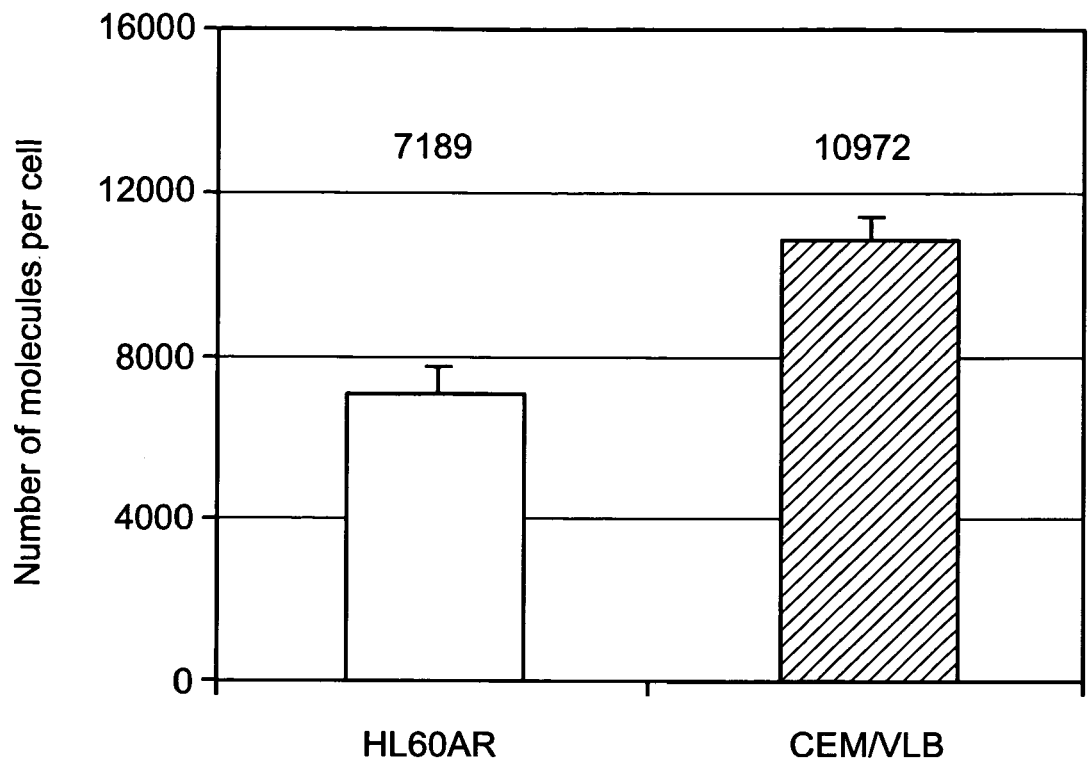

FIG. 11C is a graphic representation showing the number of molecules of HSC70 on HL60/AR and CEM/VLB cell lines.

Figure 12A:
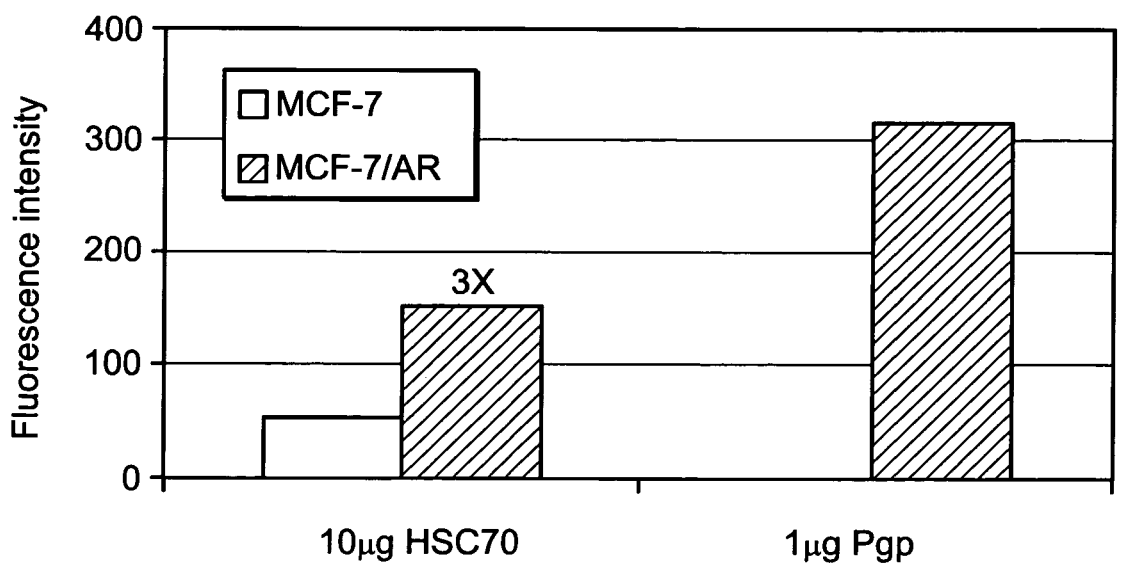

FIG. 12A is a graphic representation showing the results of FACS analysis for the surface expression of HSC70 using 10 μg monoclonal anti-HSC70 antibody and 1 μg P-glycoprotein (Pgp) on MCF-7 and MCF-7/AR cell lines.

Figure 12B:
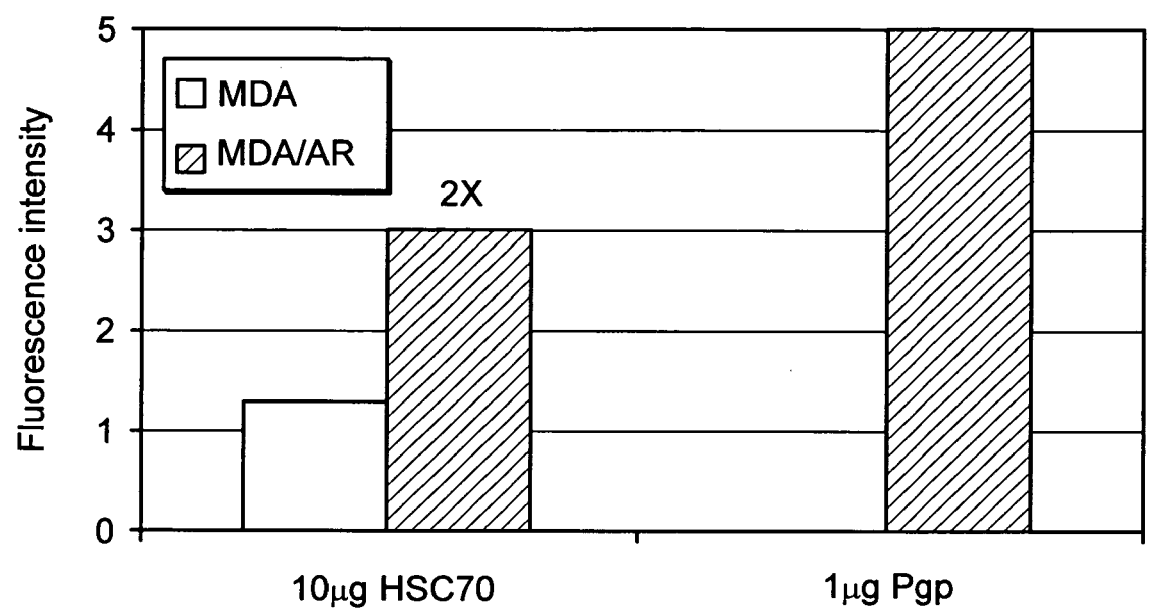

FIG. 12B is a graphic representation showing the results of FACS analysis for the surface expression of HSC70 using 10 μg monoclonal anti-HSC70 antibody and 1 μg Pgp on MDA and MDA/AR cell lines.

Figure 13A:
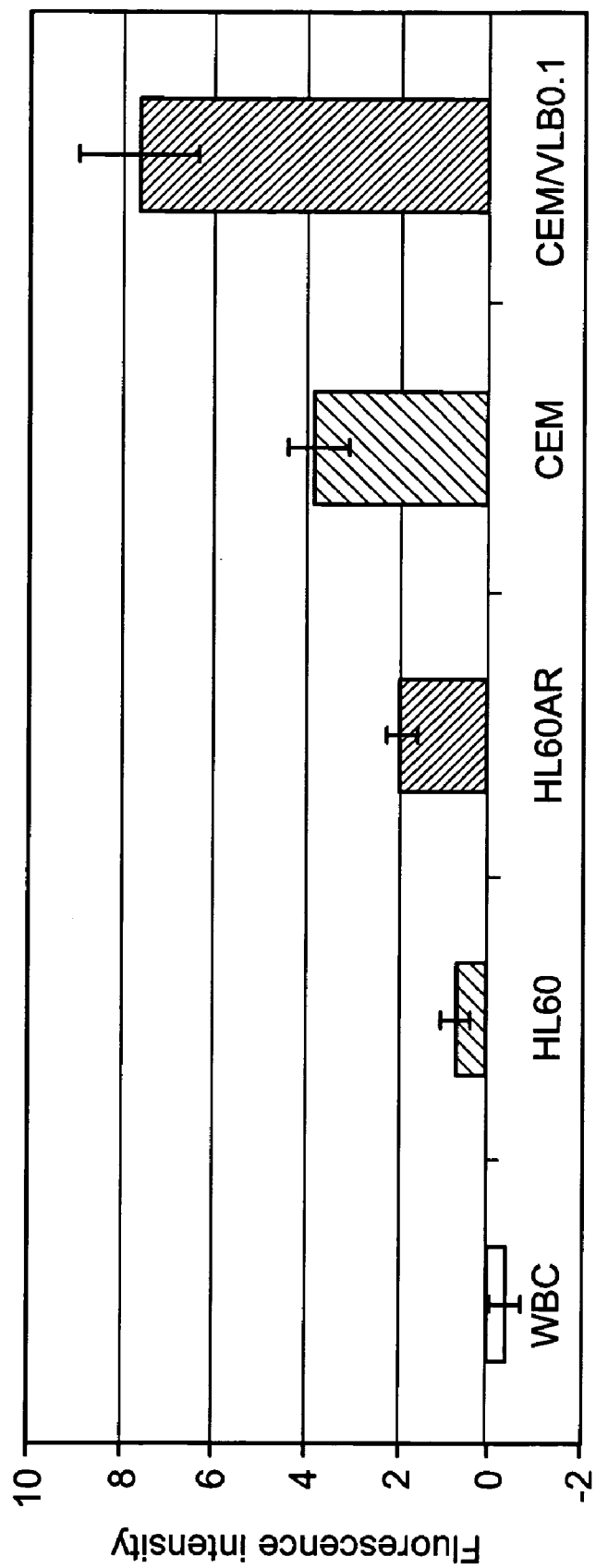

FIG. 13 is a graphic representation showing the results of FACS analysis for the surface expression of HSC70 using monoclonal anti-HSC70 antibody on normal white blood cells, HL60, HL60/AR, CEM and CEM/VLB0.1 cell lines.

FIG. 14A is a schematic representation of the polypeptide sequence of a human HSC70 corresponding to GenBank Accession No. AAK17898 (SEQ ID NO. 1).

Figures 1, 14B:
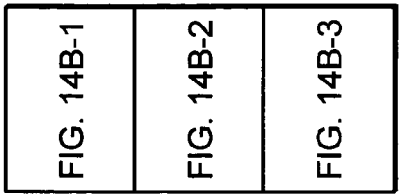

FIG. 14B is a schematic representation of the nucleotide sequence of a human HSC70-encoding nucleic acid sequence corresponding to GenBank Accession No. AF352832 (SEQ ID NO. 2). The initiation and termination codons of the vimentin protein open reading frame are underlined.

Figure 15A:
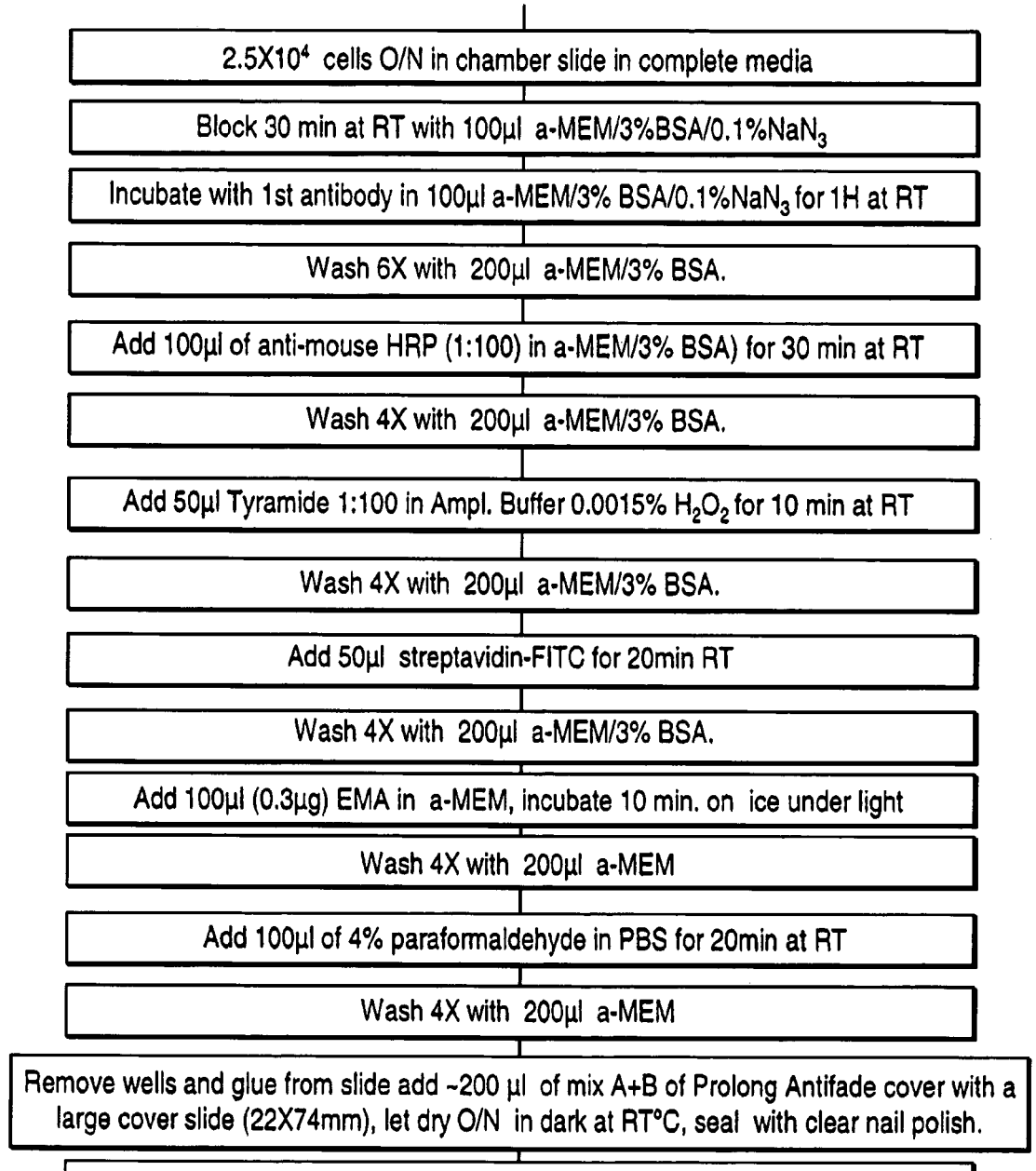
Figure 15B:
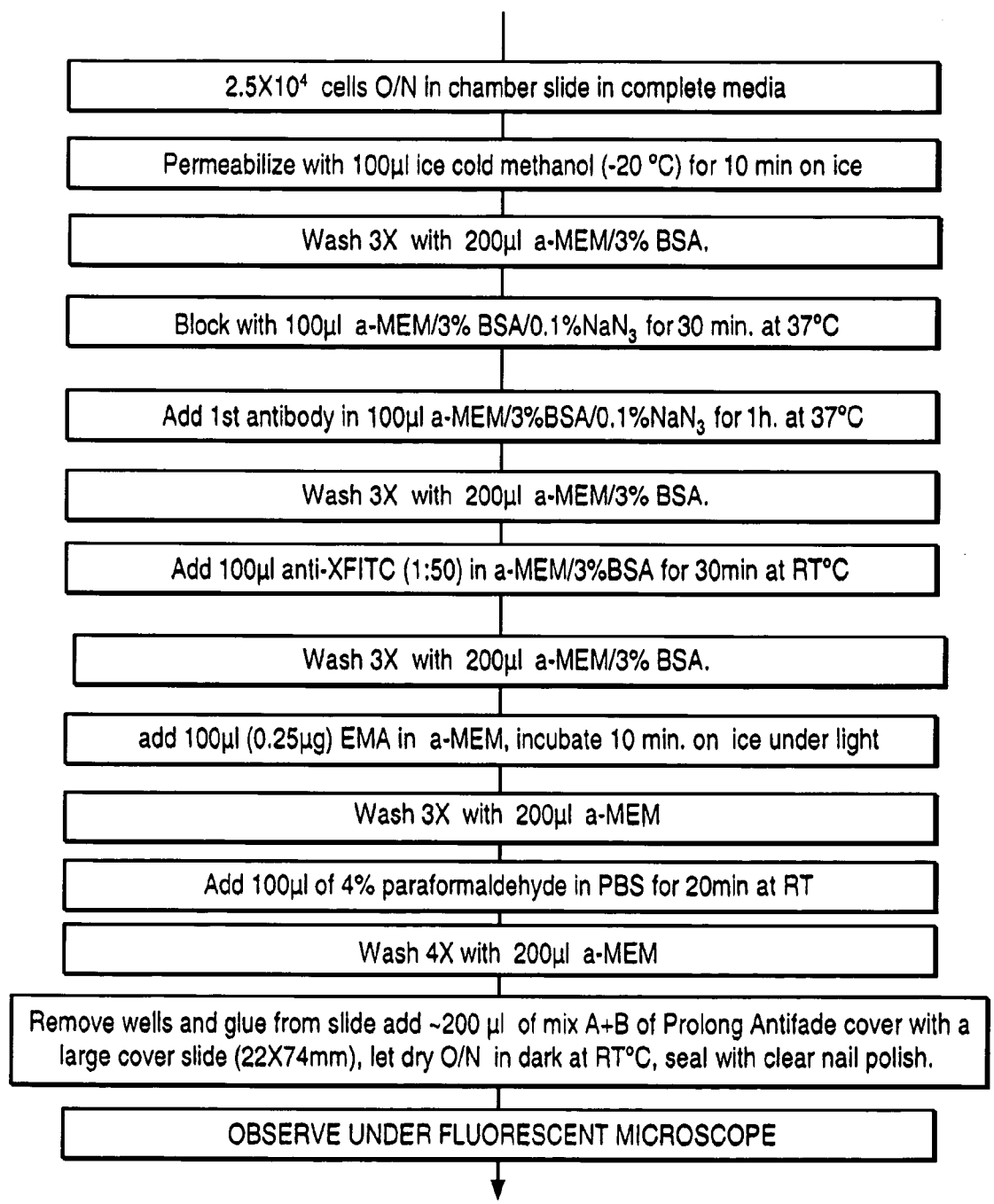

FIGS. 15A and 15B are flow charts describing in a stepwise fashion the protocol used for immunostaining of permeabilized and non-permeabilized adherent cells.

FIG. 16 shows photographic representations of permeabilized and non-permeabilized MCF-7 and MCF-7/AR cells immunostained with anti-HSC70 antibody (rat IgG2a, Stressgen SPA-815) using the procedure described in FIGS. 15A&15B. Rat IgG2a was used as negative control and didn't show any staining (not shown). Only MCF-7/AR shows surface exposed HSC70.

Figure 17:
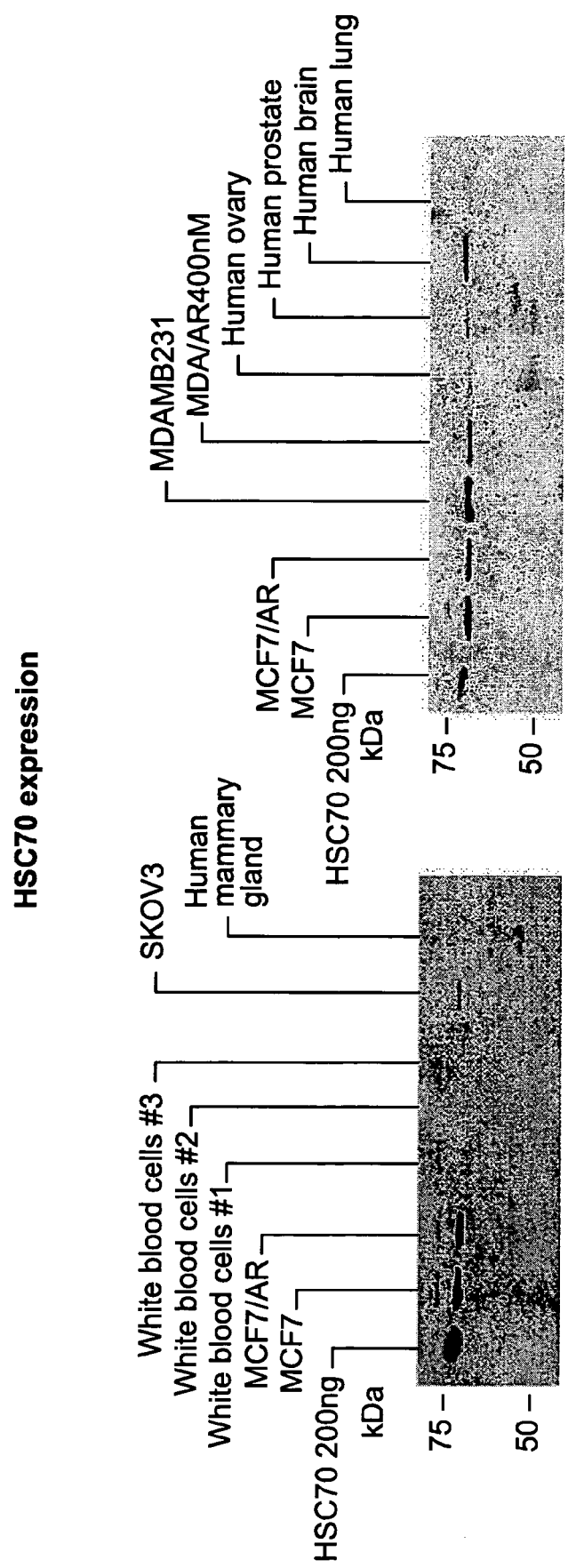

FIG. 17 is a photographic representation of a western blot analysis of various normal, sensitive and resistant cancer cell extracts resolved by SDS-PAGE.

Figure 18:
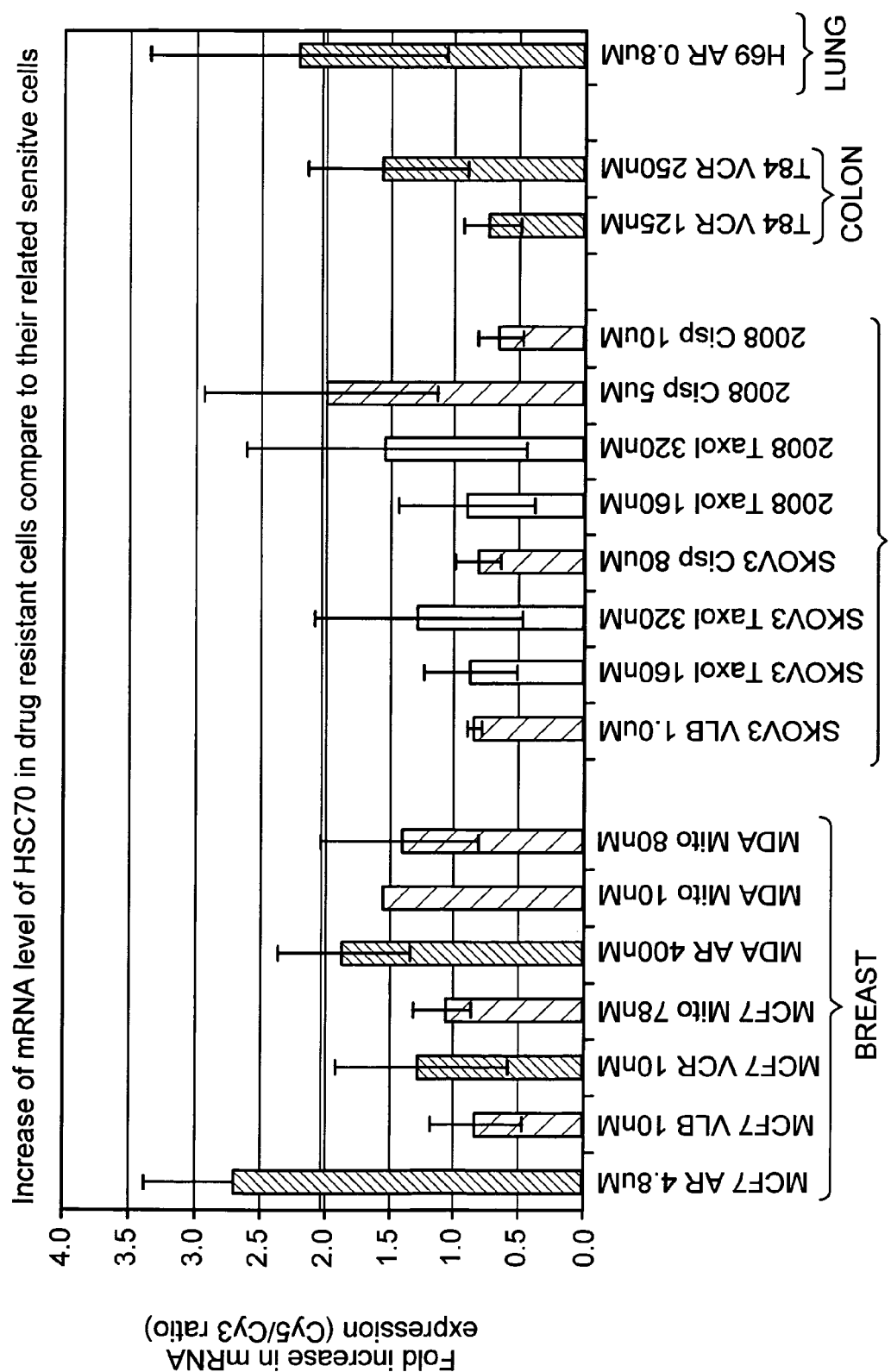

FIG. 18 is a graphic representation showing that levels of HSC70 mRNA levels are increased in drug resistant cells compared to their related sensitive cells (the fold increase in resistant versus nonresistant cells is shown in each case).

4. DETAILED DESCRIPTION

The patent and scientific literature referred to herein establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference.

In particular, this application incorporates the following patent applications by reference in their entirety: U.S. Ser. No. 60/433,480, filed Dec. 13, 2002 and entitled "Vimentin Detection-Based Methods for Diagnosing and Treating Damaged Cells, Neoplastic Cells and Multidrug Resistance;" U.S. Ser. No. 60/433,351, filed Dec. 13, 2002 and entitled "Nueleophosmin Detection-Based Methods for Diagnosing and Treating Damaged Cells, Neoplastic Cells and Multidrug Resistance," as well as U.S. Ser. No. 10/736, 889, filed Dec. 15, 2003 and entitled "Vimentin Directed Diagnostics and Therapeutics for Multidrug Resistant Neoplastic Disease;" and U.S. Ser. No. 60/438,012, filed Jan. 1, 2003 and entitled "HSC70 Detection-Based Methods for Diagnosing and Treating Damaged Cells, Neoplastic Cells and Multidrug Resistance," as well as U.S. Ser. No. 10/737, 712, filed Dec. 15, 2003 and entitled "Nucleophosmin Directed Diagnostics and Therapeutics for Multidrug Resistant Neoplastic Disease."

4.1 General

The invention provides methods and reagents for diagnosing, detecting, preventing and/or treating cancer, and for diagnosing, detecting, preventing and/or treating the development of both naturally occurring and drug-induced MDR phenotypes of damaged, non-cancerous, and cancerous cells. The invention allows for improvement of the clinical management of multidrug resistant tumors and pathogen infections. Moreover, the invention provides a reagent that allows the identification of patients having neoplastic or damaged cells, including MDR cells, thus allowing improvements in the treatment, monitoring, diagnosis, and medical imaging of multidrug resistant cancer, and pathogen and viral infections.

Accordingly, an aspect of the invention provides a method for detecting multidrug resistance in a test damaged cell. The method includes measuring the level of cell surface expression of a full-length heat shock cognate protein 70 (HSC70) on a test damaged cell of a specific type; measuring the level of cell surface expression of HSC70 protein on a drug-susceptible damaged cell of the same cell type; and determining if the test damaged cell is multidrug resistant if an increased level of cell surface-expressed HSC70 is present compared to the level of cell surface-expressed HSC70 present on the drug-susceptible damaged cell. In particular embodiments, the level of cell surface-expressed HSC70 is measured by separating the cellular components of the test damaged cell and the drug-susceptible damaged cell into fractions, and measuring the level of HSC70 present in the fraction of the cells containing the cytoplasmic or plasma membrane.

In certain embodiments, the test damaged cell is infected with a pathogen. In particular embodiments, the pathogen is a virus, a bacterium, or a parasite. Exemplary viruses include, but are not limited to, HIV, West Nile virus and Dengue virus. Exemplary bacteria include, but are not limited to, Mycobacteria, Rickettsia, and Chlamydia. Exemplary parasites include, but are not limited to, Plasmodium, Leishmania, and Taxoplasma. In some embodiments, the test damaged cell is from a tissue selected from the group consisting of blood, bone marrow, spleen, lymph node, liver, thymus, kidney, brain, skin, gastrointestinal tract, eye, breast, prostate and ovary. In certain embodiments, the test damaged cell is from a human. In particular embodiments, the human is suffering from a disease caused by the presence of the test damaged cell.

The invention also provides a method for detecting multidrug resistance in a test neoplastic cell. The method includes measuring the level of cell surface-expressed HSC70 on a test neoplastic cell of a specific cell type; measuring the level of cell surface-expressed HSC70 protein of a drug-susceptible neoplastic cell of the same cell type; and determining that the test neoplastic cell is multidrug resistant if an increased level of cell surface-expressed HSC70 is present compared to the level of cell surface-expressed HSC70 on the drug-susceptible neoplastic cell. In particular embodiments, the level of cell surface-expressed HSC70 is measured by separating the cellular components of the test neoplastic cell and the drug-susceptible neoplastic cell into fractions and measuring the level of HSC70 present in the fraction of the cells containing the cytoplasmic or plasma membrane of the cells.

Exemplary neoplastic cells include, but are not limited to, a lymphoma cell, a melanoma cell, a sarcoma cell, a leukemia cell, a retinoblastoma cell, a hepatoma cell, a myeloma cell, a glioma cell, a mesothelioma cell, and a carcinoma cell. In certain embodiments, the test neoplastic cell is from a tissue selected from the group consisting of blood, bone marrow, spleen, lymph node, liver, thymus, kidney, brain, skin, gastro-intestinal tract, eye, breast, prostate, or ovary.

In certain embodiments, the test neoplastic cell is from a human. In particular embodiments, the human is suffering from a cancer caused by the presence of the test neoplastic cell.

The invention further provides a method for detecting a multidrug resistant cell in a patient. The method includes administering a binding agent that specifically binds to HSC70 protein operably linked to a detectable label, and detecting increased binding of the binding agent specifically bound to HSC70 protein on the surface of a multidrug resistant cell in the patient compared to the binding agent bound to HSCS70 protein on the surface of a drug-susceptible cell. In this embodiment of the invention, a medical imaging device or system detects the binding agent specifically bound to the cell surface of a multidrug resistant cell in the patient. Exemplary binding agents include, but are not limited to, natural ligands, synthetic small molecules, chemicals, nucleic acids, peptides, proteins, antibodies and fragments thereof. In certain embodiments, the binding agent is an antibody.

Exemplary detectable labels include, but are not limited to, fluorophores, chemical dyes, radioactive compounds, chemiluminescent compounds, magnetic compounds, paramagnetic compounds, enzymes that yield a colored product, enzymes that yield a chemiluminescent product and enzymes that yield a magnetic product. In certain embodiments, the patient is human. In some embodiments, the multidrug resistant cell is a damaged cell or a neoplastic cell. In particular embodiments, the damaged cell is infected with a pathogen. Exemplary pathogens include, but are not limited to, viruses, bacteria and parasites. Exemplary viruses include, but are not limited to, HIV, West Nile virus and Dengue virus. Exemplary bacteria include, but are not limited to Mycobacteria, Rickettsia, and Chlamydia. Exemplary parasites include, but are not limited to Plasmodium, Leishmania, and Taxoplasma.

In particular embodiments, the neoplastic cell is selected from the group consisting of breast cancer cells, ovarian cancer cells, lymphoma cancer cells, melanoma cancer cells, sarcoma cancer cells, leukemia cancer cells, retinoblastoma cells, hepatoma cancer cells, glioma cancer cells, mesothelioma cancer cells and carcinoma cancer cells. In particular embodiments, the patient is a human. In some embodiments, the patient is suffering from a disease or disorder caused by the presence of the multidrug resistant cell.

The invention also provides a method for detecting a neoplastic cell. The method includes measuring the level of cell surface-expressed HSC70 protein on a test cell of a specific cell type suspected of being neoplastic, and determining that the test cell is neoplastic if an increased level of cell surface-expressed HSC70 protein is present compared to the level of cell surface-expressed HSC70 protein present on a normal cell of the same type. In some embodiments, the test cell is a blood cell (e.g., white blood cell, red blood cell, dendritic cell, or natural killer cell), a liver cell, a kidney cell, a brain cell, a skin cell, a cell from the gastrointestinal tract, an eye cell, a breast cell, an ovarian cell, or a prostate cell.

In some embodiments, the cell surface-expressed HSC70 is measured by separating the cellular components of the test cell and the normal cell into fractions, and measuring the level of HSC70 present in the cytoplasmic or plasma membrane fraction of the cells.

In certain embodiments, the test cell is from a tissue selected from the group consisting of blood, bone marrow, spleen, lymph node, liver, thymus, kidney, brain, skin, gastrointestinal tract, eye, breast, prostate, and ovary. In one embodiment, the test cell is from a human.

In some embodiments, the cellular components of the test cell are contacted with a detectable binding agent, followed by detection of the binding agent to determine if an increased level of cell surface-expressed HSC70 is present on the test cell compared to the level of cell surface-expressed HSC70 present on a normal cell of the same type. In particular embodiments, the intact suspected neoplastic cell is contacted with the detectable binding agent.

The invention also allows the early identification of patients having such MDR neoplastic or damaged cells. For example, where the patient identified as having such cells is an asymptomatic patient who is being treated for an infectious disease, or had received treatment for an infectious disease (e.g., hepatitis B), the invention allows identification of these patients prior to resurgence of symptoms, as well as the monitoring of these patients during treatment with a drug, such that the treatment regimen can be altered if such MDR cells are detected. Similarly, where the patient identified as having such cells is a patient in remission of cancer or is being treated for cancer (e.g., a patient suffering from breast cancer or leukemia), the invention allows identification of these patients prior to resurgence and/or progression of their cancer, as well as allows the monitoring of these patients during treatment with a drug, such that the treatment regimen can be altered.

The present invention stems from the realization that cell surface expressed HSC70 is useful as a marker for multidrug resistance of a cell. An important advantage of the HSC70 protein cell surface marker is that it is found intracellularly in normal cells of the body and is not expressed on their cell surface. This expression profile is in contrast to the situation with other known MDR markers such as P-glycoprotein and MRP, which are present at variable levels on the surface of cells of different normal tissues, including high levels on the surface of liver, kidney, stem cells, and blood-brain barrier epithelial cells (Cordon-Cardo C. et al., *J. Histochem. Cytochem.* 38: 1277–1287, 1990; Nakamara T. et al., *Drug Metabolism & Disposition,* 30: 4–6, 2002). As a consequence, cytotoxic agents directed against MDR cancer cell markers such as P-glycoprotein and MRP have been limited by the adverse effects of killing normal cells that also express high levels of cell surface P-glycoprotein and MRP (see, e.g., FitzGerald, D. J. et al., *Proc. Natl. Acad. Sci.* 84: 4288–4292, 1987). The present invention overcomes this problem because the HSC70 MDR marker is expressed at high levels on the surface of MDR cancer cells and MDR non-cancerous damaged cells (e.g., cells infected with a virus), at moderate levels on the cell surface of drug-sensitive cancer cells compared to the very low or negligible levels on drug-sensitive non-cancerous normal cells. Thus, the invention provides cytotoxic agents directed toward cell surface expressed HSC70 which kills MDR neoplastic or damaged and drug-sensitive neoplastic and damaged cells, and leaves normal cells unscathed.

It should be noted that the same MDR neoplastic or damaged cell may express more than one MDR marker (e.g., may express both HSC70 and P-glycoprotein) simultaneously, or may express an MDR marker independently. Joint expression of different markers on the same MDR cell offers the possibility of combining binding agents directed against more than one cell surface MDR marker. For example, a sub-lethal dosage of a binding agent that specifically binds to HSC70 can be combined with a sub-lethal dosage of a binding agent that specifically binds to P-glycoprotein. Since normal cells do not express HSC70 on their cell surface, these cells will not be harmed by the binding agent that specifically binds to HSC70. Rather, only MDR cells that express both P-glycoprotein and HSC70 on their cell surface will be killed by this combination therapy.

As used herein, the terms, "multidrug resistant" and "multidrug resistance," are used to refer to the development, in a neoplastic cell or damaged cell, of resistance to a number of different drugs, including drugs to which the neoplastic cell or damaged cell was never exposed. For example, if a patient suffering from leukemia being treated with vincristine develops leukemia cells resistant to vincristine as well as other chemotherapeutics that the patient had never received (e.g., methotrexate or mercaptopurine), that patient's leukemic cells are multidrug resistant. Similarly, if a patient suffering from tuberculosis being treated with penicillin develops tuberculosis-infected cells resistant to penicillin as well as other chemotherapeutics that the patient had never received (e.g., erythromycin), that patient's tuberculosis-infected cells are multidrug resistant. Notably, multidrug resistance (MDR) may include acquired simultaneous resistance to a wide spectrum of drugs, including drugs with little structural or even functional similarity to the original drug(s), and results in reduced efficacy of all the drugs concerned.

Note that the terms, "multidrug resistant" and "multidrug resistance," are used to describe a neoplastic cell or a damaged cell that is multidrug resistant due to either the classical mechanism (i.e., involving P-glycoprotein or another MDR protein) or an a typical mechanism (non-classical mechanism) that does not involve P-glycoprotein (e.g., an a typical mechanism that involves the MRP1 multidrug resistance marker). Moreover, in accordance with the invention, a cell (e.g., a neoplastic or damaged cell) that develops multidrug resistance can develop such MDR status either by being exposed to a drug (e.g., a chemotherapeutic drug or an antibiotic drug), or by naturally developing such MDR (i.e., without having been exposed to a drug).

As used herein, the term "MDR protein" includes any of several integral transmembrane glycoproteins of the ABC type that are involved in (multiple) drug resistance. These include MDR 1 (P-glycoprotein or P-glycoprotein 1), an energy-dependent efflux pump responsible for decreased drug accumulation in multidrug resistant cells. Examples of MDR 1 include human MDR 1 (see, e.g., database code MDR1_HUMAN, GenBank Accession No. P08183, 1280 amino acids (141.34 kDa)). Other MDR proteins include MDR 3 (or P-glycoprotein 3), which is an energy-dependent efflux pump that causes decreased drug accumulation but is not capable of conferring drug resistance by itself. Examples of MDR 3 include human MDR 3 (see, e.g., database code MDR3_HUMAN, GenBank Accession No. P21439, 1279 amino acids (140.52 kDa). Other MDR-associated proteins participate in the active transport of drugs into subcellular organelles. Examples from human include MRP 1, Multi-drug Resistance-associated Protein 1, database code MRP_HUMAN, GenBank Accession No. P33527, 1531 amino acids (171.47 kDa).

In accordance with the invention, a cell (e.g., a neoplastic or damaged cell) that develops multidrug resistance can develop such MDR status either by being exposed to a drug (e.g., a chemotherapeutic drug or an antibiotic drug), or by naturally developing such MDR (i.e., without having been exposed to the drug to which the cell has developed resistance). In this respect, the invention allows the detection of the potentially multidrug resistant character of a neoplasm even before the neoplasm has been treated. Similarly, the invention allows for the effective treatment of, for example, potentially multidrug resistant neoplasms even before the neoplasm has been treated and shown to be drug resistant.

Cell surface expressed HSC70 is a superior marker for use in therapies that kill MDR neoplastic cells and MDR damaged cells bearing the HSC70 marker on their cell surface (such as immunotoxin therapy), since normal cells are spared from cell killing, thus reducing or eliminating harmful side effects of treatment. Similarly, diagnosis and imaging of MDR neoplastic or damaged cells using the cell surface HSC70 marker are more sensitive and accurate, and provide fewer false positives compared to diagnosis and imaging of MDR neoplastic and damaged cells using the MDR markers such as P-glycoprotein or MRP that are also expressed on normal tissues. Moreover, cell surface HSC70 is useful as an anti-MDR cancer vaccine antigen or an anti-MDR damaged cell vaccine antigen for vaccination of patients against their cancers or damaged cell tissue expressing HSC70 on their cell surface.

The present invention also allows the identification of those patients whose neoplastic or damaged cells have acquired multidrug resistance. In some situations, the patient is identified when he/she no longer responds to the drug being used in his/her treatment. For example, a breast cancer patient or leukemia patient in remission being treated with a chemotherapeutic agent (e.g., vincristine) may suddenly come out of remission, despite being constantly treated with the chemotherapeutic agent. Unfortunately, such a patient is often found also to be unresponsive to other chemotherapeutic agents, including some with which the patient had never originally been treated. Of course, after these patients become multidrug resistant, treating these patients to control their now-resurgent cancer or disease caused by a damaged cell is difficult and may require more drastic therapies, such as radiotherapy or surgery (e.g., bone marrow transplantation or amputation of necrotic tissue).

The invention allows for early diagnosis of multidrug resistance by detecting the cell surface expression of HSC70 on the patient's neoplastic or damaged cells. Such an early diagnosis allows patients who are initially drug responders and sensitive to drug treatment to be distinguished from those who are initially drug non-responders. Thus, the drug non-responders can be treated with a more effective treatment. Further, the HSC70 marker can occur together with, or independently of, other MDR markers on the same cancerous or damaged cells, allowing for the possibility of combination therapy directed simultaneously against HSC70 and other MDR cancer and damage markers (e.g. P-glycoprotein and MRP).

In addition, diagnostic procedures using HSC70 cell surface expression may also be used to follow the development and emergence of MDR neoplastic or damaged cells that are resistant to the treatment drug and that arise during the course of drug treatment. For example, such procedures are useful for treating AIDS patients that have been treated with AZT and that have been reported to subsequently develop multidrug resistance to a wide spectrum of antiviral, antibacterial, and anticancer drugs (see Gollapudi et al., *Biochem. Biophys. Res. Commun.* 171: 1002–1007, 1990; Antonelli et al., *AIDS Res. Human Retroviruses* 8: 1839–1844, 1992).

In another example, diagnostic assays for HSC70 cell surface expression are useful for selecting patients in clinical studies involving therapy for treatment of neoplastic or damaged cells. Hence, the presence of HSC70 on the cell surface of a patient's cells either qualifies or disqualifies that patient from being included in a given clinical study.

Accordingly, in one aspect, the invention provides a method for detecting multidrug resistance in a test damaged cell suspected of being multidrug resistant. The method includes measuring the level of cell surface-expressed HSC70 protein on the surface of the test damaged cell of a specific cell type; measuring the level of cell surface-expressed HSC70 protein on a drug-susceptible damaged cell and determining that the test damaged cell is multidrug resistant if an increased level of cell surface-expressed HSC70 is present compared to the level of cell surface-expressed HSC70 on the drug-susceptible damaged cell.

In another aspect, the invention provides a method for detecting multidrug resistance in a test neoplastic cell suspected of being multidrug resistant. The method includes measuring the level of cell surface-expressed HSC70 protein on the test neoplastic cell if a specific cell type; measuring the level of cell surface-expressed HSC70 protein on a drug-susceptible neoplastic cell of the same type; and that determining that the test neoplastic cell is multidrug resistant if an increased level of cell surface-expressed HSC70 is present compared to the level of cell surface-expressed HSC70 present on the drug-susceptible neoplastic cell.

In another aspect, the invention provides a method for detecting cancer in a test cell suspected of being cancerous (i.e. neoplastic). The method includes measuring the cell surface-expressed HSC70 protein on the test cell and on a normal cell (known not to be cancerous), and determining that the test cell is cancerous if a level of cell surface-expressed HSC70 is increased compared to the level of cell surface-expressed HSC70 present on a normal, nucleated cell of the same cell type.

In some embodiments, the test damaged cell or test neoplastic cell expresses an amount of HSC70 on its cell surface that is at least two-fold higher than the level of cell surface expression of the heat shock cognate protein 70 on a normal cell or on a non-MDR damaged cell or non-MDR neoplastic cell, respectively. Such a determination of level of cell surface expression can be made by any number of known methods including, without limitation, those methods described below.

As used in accordance with the invention, a "damaged cell" is used to mean a cell that is non-neoplastic, but that has been otherwise injured. For example, the non-neoplastic damaged cell may be a cell infected with a pathogen, such as a virus, a bacterium, or a parasite. In one non-limiting example, the cells may be damaged by infection with a multi-cellular parasite, or damaged by the effects of infection by a parasite. Such non-limiting parasites include Plasmodium, Leishmania, and Taxoplasma. Such non-limiting viruses include HIV, West Nile virus and Dengue virus; such non-limiting bacteria include Mycobacteria, Rickettsia, and Chlamydia.

In certain embodiments, the test damaged cell is from a tissue, for example, from a biopsy of damaged tissue (e.g., necrotic tissue), or from a type of cell that is infected by the pathogen. For example, the hepatitis B virus typically infects only liver cells; thus, a damaged cell (i.e., a liver cell infected by hepatitis B virus) is from a tissue (i.e., liver). Similarly, the Human Immunodeficiency Virus (HIV) typically infects only $CD4^+$ T cells and macrophages; thus a damaged cell (e.g., a CD4+ T cell infected with HIV) is from a tissue (i.e., blood or bone marrow).

Note that in some limited situations, infection by a virus may cause a cell to become neoplastic. For example, some B cells, when infected with the Epstein Barr Virus (EBV), become neoplastic. Such a neoplastic B cell, although damaged by virtue of its infection with a virus, is included herein as a "neoplastic cell."

As used herein, a "neoplastic cell" is a cell that shows aberrant cell growth, such as increased cell growth. A neoplastic cell may be a hyperplastic cell, a cell that shows a lack of contact inhibition of growth in vitro, a tumor cell that is incapable of metastasis in vivo, or a cancer cell that is capable of metastasis in vivo. Non-limiting examples of neoplastic cells include melanoma, breast cancer, ovarian cancer, prostate cancer, sarcoma, leukemic, retinoblastoma, hepatoma, myeloma, glioma, mesothelioma, carcinoma, leukemia, lymphoma, Hodgkin lymphoma, Non-Hodgkin lymphoma, myeloma, promyelocytic leukemia, T lymphoblastoic, myelodysplastic syndrome, lymphoblastoma, and thymoma cells.

In certain embodiments, the test neoplastic cell is from a tissue, for example, from a biopsy of a hyperplastic tissue (e.g., a lump in the breast). Non-limiting examples of tissues from which a test neoplastic cell can be from include, but are not limited to, blood, bone marrow, spleen, lymph node, liver, thymus, spleen, kidney, brain, skin, gastro-intestinal tract, eye, breast, prostate, and ovary.

In accordance with the invention, a damaged cell is from a patient, such as a human. In certain embodiments, the patient is suffering from a disease or disorder where the disease or disorder is caused by the presence of the damaged cell. For example, where the damaged cell is infected with a pathogen, the disease is an infection caused by the presence of those damaged cells infected by the pathogen or lack thereof (e.g., AIDS caused by the lack of CD4+ T cells which were infected by the HIV virus).

In accordance with the invention, the test neoplastic cell is from a patient, such as a human. In certain embodiments, the patient is suffering from a disease or disorder where the disease or disorder is caused by the presence of the neoplastic cell. For example, where the neoplastic cell is a neoplastic melanoma cell, the disease is a cancer of the melanoma cell (i.e., the cancer is melanoma which is caused by aberrant cell growth and metastasis of the neoplastic cell).

As used herein, a "patient suffering from a disease or disorder" is meant a patient who has the clinical manifestations and/or symptoms of a disease or disorder. In certain situations, a patient with a disease or disorder may be asymptomatic, and yet still have clinical manifestations of the disease or disorder. For example, a patient suffering from leukemia, may not be symptomatic (e.g., may not be sick or weak), but shows the clinical manifestation in that the patient has a larger number of white blood cells as compared to a healthy individual of the same age and weight. In another non-limiting example, a patient suffering from infection with a virus (e.g., HIV), may not be symptomatic (e.g., may not show a diminished CD4+ T cell count), but shows the clinical manifestation in that the patient has anti-HIV antibodies.

According to the invention, those neoplastic cells that have become cancerous are distinguishable from normal, nucleated cells by the increased expression of full-length HSC70 protein on the cell surface.

According to the invention, those damaged cells or neoplastic cells that have become multidrug resistant are distinguishable from those cells that are not multidrug resistant by the increased expression of the full length HSC70 protein on the cell surface of multidrug resistant cells. Representative nucleotide and amino acid sequences of HSC70 are set forth in FIG. 14 (also see GI 5729877 and GI 1398297). Thus, when the cellular components are separated, those cells that are multidrug resistant contain HSC70 on their cytoplasmic or plasma membrane fraction. Cell surface expression of HSC70 protein may also be routinely detected by non-limiting methods such as FACS analysis, cell surface biotinylation followed by 2-D gels, immunoprecipitation (see Examples), or immunofluorescent analysis of fixed clinical specimens, and other types of routine methods performed by those skilled in the art.

In some embodiments, measuring the level of expression of a HSC70 protein on the surface of the test damaged cell or test neoplastic cell comprises separating the cellular components of the test cell into fractions, and then measuring the level of HSC70 in the fraction of the cell containing the plasma or cytoplasmic membrane.

Alternatively, measuring the level of expression of HSC70 on the surface of the test damaged cell or test neoplastic cell comprise separating the products of enzymatic digestion of cell surface-expressed HSC70 protein from the test cell. In one non-limiting example, intact cells from a patient are digested with enzymes. The peptides from the digested, surface-exposed proteins are isolated by quickly spinning down the cells and leaving the digested peptides in the supernatant. These digested peptides can be analyzed by various methods (e.g., immunological methods or mass spectroscopy) to determine if HSC70 is expressed on the cell surface.

Separation of cellular components may be performed by any standard separation procedure including, without limitation, thin layer chromatography, gas chromatography, high performance liquid chromatography, paper chromatography, affinity chromatography, supercritical flow chromatography, gel electrophoresis, and the procedures described below in the Examples section. Separation procedures are generally known (see, e.g., Scopes and Scopes, *Protein Purification: Principles and Practice*, Springer Verlag 1994).

In some embodiments, measuring the level of expression of a HSC70 protein on the surface of the test damaged cell includes contacting the intact test damaged cell or test neoplastic cell with a detectable binding agent that specifically binds to a HSC70 protein. Thus, the detectable binding agent specifically binds to cells which express HSC70 on their cell surface.

According to the invention, while normal cells express no or negligible amounts of HSC70 on their cell surface, a neoplastic cell or a damaged cell expresses more HSC70 on their cell surface. Additionally, when such neoplastic or damaged cells become multidrug resistant, they express even higher levels of the entire, full length HSC70 protein on their cell surface. An HSC70-specific binding agent specifically binds to any portion of the HSC70 protein since the entire protein is expressed on the cell surface of multidrug resistant neoplastic or damaged cells.

Of course, since HSC70 is also expressed inside of normal cells, drug-sensitive neoplastic cells, and drug-sensitive damaged cells, if such normal cells and drug-sensitive neoplastic or damaged cells are first lysed or if their membranes are permeabilized prior to addition of the binding agent, the binding agent will also bind to intracellular HSC70 in normal and drug-sensitive neoplastic or damaged cells.

In some embodiments, MDR neoplastic cells or MDR damaged cells that express HSC70 on their cell surface are distinguishable from other types of cells, in that the MDR neoplastic or damaged cells express the full length HSC70 protein on their cell surface at levels that are at least two-fold higher than the normal cells from the tissue of origin of the neoplastic or damaged cells, or at levels that are at least two-fold higher than drug-sensitive neoplastic or damaged cells from the tissue of origin. For example, a leukemic T cell expresses more HSC70 on its cell surface than does a normal T cell. Moreover, as described below, a MDR leukemic T cell expresses at least twice as much HSC70 on its cell surface as a leukemic T cell that is not multidrug resistant. Similarly, as described in the examples below, an MDR breast cancer cell expresses at least twice as much HSC70 on its cell surface as its drug-sensitive counterpart (i.e., the drug-sensitive counterpart is not multidrug resistant). If the cellular components of such cells are separated (e.g., into membrane fraction and cytosolic fraction), those MDR neoplastic or damaged cells that express HSC70 at their cell surface contain HSC70 in their membrane fractions at two fold or higher levels than do other cells from the same tissue that are not multidrug resistant, regardless whether the non-multidrug resistant cell is normal, neoplastic, or damaged.

In another aspect, the invention provides a binding agent that specifically binds to a HSC70 protein. As used herein, "specifically binds" means that a binding agent (e.g., an antibody) recognizes and binds to a HSC70 protein, but does not substantially recognize and bind to other molecules in a sample. Thus, such a binding agent of the invention binds to the surface of a MDR cell that expresses HSC70 on its cell surface. A useful binding agent that specifically binds to an HSC70 protein forms an association with the HSC70 protein with an affinity of at least $10^6$ $M^{-1}$, or at least $10^7$ $M^{-1}$, or at least $10^8$ $M^{-1}$, or at least $10^9$ $M^{-1}$ either in water, under physiological conditions, or under conditions which approximate physiological conditions with respect to ionic strength, e.g., 140 mM NaCl, 5 mM $MgCl_2$.

A "binding agent" need not be any particular size or have any particular structure so long as it specifically binds to the HSC70 protein. Thus, a "binding agent" is a molecule that attaches to any region (e.g., three dimensional structure, amino acid sequence, or particular small chemical groups) so long as it preferentially binds to the HSC70 protein. Non-limiting examples of binding agents include natural ligands (such as hormones or GTP), as well as synthetic small molecules, chemicals, nucleic acids, peptides, and proteins such as hormones, antibodies, and portions thereof. Typically, the binding agent's ability to specifically bind an epitope is based on highly complementary structures. That is, the shape of the binding agent contains structures that are the complement of the portion on the antigen to which the binding agent specifically binds. The portion of the antigen to which an antibody binds is called an "epitope."

In certain embodiments, the binding agent is an antibody. Where the binding agent that specifically binds an HSC70 protein is an antibody, the antibody may be, without limitation, a polyclonal antibody, a monoclonal antibody, a chimeric antibody, a humanized antibody, a genetically engineered antibody, a bispecific antibody (where one of the specificities of the bispecific antibody specifically binds to the HSC70 protein), antibody fragments (including but not limited to "Fv," "F(ab')$_2$," "F(ab)," and "Dab"); and single chains representing the reactive portion of an antibody ("SC-MAb"). Methods for making antibodies and other binding agents are well known (see, e.g., Coligan et al., *Current Protocols in Immunology*, John Wiley and Sons, New York City, N.Y., 1991; Jones et al., *Nature* 321: 522–525,1986; Marx, *Science* 229: 455–456, 1985; Rodwell, *Nature* 342: 99–100, 1989; Clackson, *Br. J. Rheumatol.* 3052: 36–39, 1991; Reichman et al., *Nature* 332: 323–327, 1988; Verhoeyen, et al., *Science* 239: 1534–1536, 1988).

As used herein, by "detectably labeled" is meant that a binding agent of the invention is operably linked to a moiety that is detectable. By "operably linked" is meant that the moiety is attached to the binding agent by either a covalent or non-covalent (e.g., ionic) bond. Methods for creating covalent bonds are known (see general protocols in, e.g., Wong, S. S., *Chemistry of Protein Conjugation and Cross-Linking*, CRC Press 1991; Burkhart et al., *The Chemistry and Application of Amino Crosslinking Agents or Aminoplasts*, John Wiley & Sons Inc., New York City, N.Y. 1999).

In accordance with the invention, a detectably labeled binding agent includes a binding agent that is conjugated to a detectable moiety. Another detectably labeled binding agent of the invention is a fusion protein, where one partner is the binding agent and the other partner is a detectable label. Yet a further non-limiting example of a detectably labeled binding agent is a first fusion protein comprising a binding agent and a first moiety with high affinity a second moiety, and a second fusion protein comprising a second moiety and a detectable label. For example, a binding agent that specifically binds to an HSC70 protein may be operably linked to a streptavidin moiety. A second fusion protein comprising a biotin moiety operably linked to a fluorescein moiety may be added to the binding agent-streptavidin fusion protein, where the combination of the second fusion protein to the binding agent-streptavidin fusion protein results in a detectably labeled binding agent (i.e., a binding agent operably linked to a detectable label).

According to the invention, a detectable label is a moiety that can be detected and includes, without limitation, fluorophores (e.g., fluorescein (FITC), phycoerythrin, rhodamine), chemical dyes, or compounds that are radioactive, chemoluminescent, magnetic, paramagnetic, promagnetic, or enzymes that yield a product that may be colored, chemoluminescent, or magnetic. In particular embodiments, the detectable label is detectable by a medical imaging device or system. For example, where the medical imaging system is an X-ray machine, the detectable label that can be detected by the X-ray machine is a radioactive label (e.g., $^{32}$P). Note that a binding agent need not be directly conjugated to the detectable moiety. For example, a binding agent (e.g., a mouse anti-human HSC70 antibody) that is itself specifically bound to by a secondary detectable binding agent (e.g., a FITC labeled goat anti-mouse secondary antibody) is operably linked to a detectable moiety (i.e., the FITC moiety).

In some embodiments, measuring the level of expression of a HSC70 protein on the surface of the test damaged cell includes contacting the intact, test damaged cell with a detectable binding agent that specifically binds to a HSC70 protein. For example, where the detectable binding agent is detectably labeled by being operably linked to a fluorophore, cells staining with the fluorophore (i.e., those that are specifically bound by the binding agent) can be identified by fluorescent activated cell sorter analysis (see Examples), or by routine fluorescent microscopy of clinical specimens prepared on slides.

In addition to detectable moieties, other non-limiting moieties that may be operably linked to a binding agent of the invention include, without limitation, a toxin (e.g., a radioactive isotope), an enzyme, an antibody (or a portion thereof), a cytotoxic drug, or a conjugate of these. Where a toxin is operably linked to a binding agent of the invention, non-limiting examples of a toxin which can be operably linked to a binding agent of the invention include a radioactive isotope, Diptheria toxin, a nuclease (e.g., DNAse or RNAse), a protease, a degradative enzyme, *Pseudomonas* exotoxin (PE), ricin A or B chains, *Pseudomonas* exotoxin (PE), and ribonuclease A (Fizgerald D., *Semin. Cancer Biol.* 7: 87–95, 1996).

In some embodiments, the binding agent is an immunotoxin (e.g., an antibody-toxin conjugate or antibody-drug conjugate). Non-limiting examples of immunotoxins include antibody-anthracycline conjugates (Braslawsky G. R. et al., European Patent No. EP0398305), antibody-cytokine conjugates (Gilles S. D., PCT Publication No. WO9953958), and monoclonal antibody-PE conjugates (Roffler S. R. et al., *Cancer Res.* 51: 4001–4007, 1991).

In a further aspect, the invention provides a therapeutic composition comprising a cytotoxic drug, a binding agent that specifically binds to a HSC70 protein, and a pharmaceutically-acceptable carrier. Non-limiting examples of such pharmaceutically-acceptable carriers are described in more detail in *Remington: The Science and Practice of Pharmacy*, Gennaro et al. (eds), 20$^{th}$ Edition, Lippincott Williams & Wilkins, Philadelphia, Pa., 2001 (ISBN 0-683-306472), a standard reference text. In certain embodiments, binding of the binding agent is toxic to damaged cells, regardless of whether such cells are drug-sensitive or multidrug resistant. In some embodiments, binding of the binding agent is toxic to neoplastic cells, regardless of whether such cells are drug-sensitive or multidrug resistant. In certain embodiments, the binding agent of the composition is operably linked to a toxin.

Actual methods for preparing therapeutic compositions are known or apparent to those skilled in the art, and are described in detail in *Remington: The Science and Practice of Pharmacy*, 2001 (supra); and in *Pharmaceutical Dosage Forms and Drug Delivery Systems*, 6th ed., Williams & Wilkins (1995). The therapeutic compositions of the invention may be in any form suitable for administration including, without limitation, in the form of a tablet, a capsule, a powder, a solution, or an elixir.

Note that a cytotoxic drug of the therapeutic composition of the invention need not be cytotoxic to all cells. In some embodiments, where the therapeutic composition is being administered to a patient suffering from a disease caused by the presence of a damaged cell, the cytotoxic drug of the therapeutic composition is an antipathogenic or antimicrobial drug. In some embodiments, where the damaged cells are infected with a pathogen (e.g., a virus, a bacterium, or a multi-cellular parasite) and the disease is caused by the infection. Where the damaged cells are infected by a pathogen, non-limiting examples of the drug differs with the infecting pathogen but may include Acyclovir, amphotericin, ampicillin, anthracyclin, b-lactam antibiotics, cephalothin, chloramphenicol, chloroquine (CQ), cidofovir (CDV), ciprofloxacin, erythromycin, fluconazole, 5 flucytosine, fluoroquinolone, foscarnet, gancyclovir, halofantrine, Itraconazole, lamivudine, macrolides, mefloquine, methicillin, metronidazole, miconazole, nelfinavir, ofloxacin, penicillin, primaquine, quinoline, Streptomycin, Sulfonamides, teicoplanin, terbinafine, tetracycline, vancomycin, voriconazole. Therapeutically effective amounts of such drugs are known to routinely skilled physicians and pharmacists. In addition, such information can be obtained from the manufacturer of the drug, or from the *Physician's Desk Reference*, Medical Economics Co. (published yearly).

In some embodiments, where the therapeutic composition is being administered to a patient suffering from a cancer caused by the presence of a neoplastic cell, the cytotoxic drug of the therapeutic composition is an anti-cancer drug. Such anti-cancer drugs include, without limitation, chemotherapeutic drugs and radiotherapeutic drugs. Non-limiting examples of such anti-cancer drugs include Actinomycin, Adriamycin (AR), Altretamine, Asparaginase, Bleomycin, Busulfan, Capecitabine, Carboplatin, Carmustine, Chlorambucil, Cisplatin, Cladribine, Cyclophosphamide, Cytarabine, Dacarbazine, Dactinomycin, Daunorubicin, Docetaxel, Doxorubicin (DOX), Epoetin, Etoposide, Fludarabine, Fluorouracil, Gemcitabine, Hydroxyurea, Idarubicin, Ifosfamide, Imatinib, Irinotecan, Lomustine, Mechlorethamine, Melphalan, Mercaptopurine, Methotrexate, Mitomycin (MITO), Mitotane, Mitoxantrone, Paclitaxel, Pentostatin, Procarbazine, Taxol, Teniposide, Topotecan, Vinblastine (VLB), Vincristine, and Vinorelbine. Therapeutically effective amounts of such drugs are known to routinely skilled physicians and pharmacists. In addition, such information can be obtained from the manufacturer of the drug, or from the *Physician's Desk Reference*, Medical Economics Co. (published yearly).

In another aspect, the invention provides a method for treating a patient suffering from a disease caused by the presence of damaged cells. This method includes administering to the patient a therapeutically effective amount of a drug and a therapeutically effective amount of a binding agent that specifically binds to an HSC70 protein. In some embodiments, the binding agent kills damaged cells that are multidrug resistant while the drug kills damaged cells that are drug-sensitive. Of course, since the HSC70 protein is expressed at moderate levels on drug-sensitive damaged cells, the binding agent, which, in some embodiments is different than the drug, will also kill drug-sensitive damaged cells. According to this method, the patient shows an improved prognosis for the disease as compared to an untreated patient. The drug and the binding agent can be separately administered at different times in any order or can administered together. In some embodiments, the patient is a human.

In certain embodiments, the damaged cells of the patient are infected with a pathogen. Such as a virus, a bacterium, or a parasite.

In yet another aspect, the invention provides a method for treating a patient suffering from a disease (e.g., cancer) caused by the presence of neoplastic cells. This method includes administering to the patient a therapeutically effective amount of a drug and a therapeutically effective amount of a binding agent that specifically binds to an HSC70 protein. In some embodiments, the binding agent kills neoplastic cells that are multidrug resistant while the drug kills neoplastic cells that are drug-sensitive. Since the HSC70 protein is expressed on drug-sensitive neoplastic cells, in some embodiments, the binding agent, which, in some embodiments is different than the drug, will also kill drug-sensitive neoplastic cells. According to this method, the patient shows an improved prognosis for the disease as compared to an untreated patient. The drug and the binding agent (e.g., an antibody) can be separately administered in any order at different times or can be administered together. In some embodiments, the patient is a human.

In certain embodiments, the neoplastic cells of the patient are breast cancer cells, ovarian cancer cells, myeloma cancer cells, lymphoma cancer cells, melanoma cancer cells, sarcoma cancer cells, leukemia cancer cells, retinoblastoma cancer cells, hepatoma cancer cells, glioma cancer cells, mesothelioma cancer cells, or carcinoma cancer cells.

In certain embodiments, the binding agent administered to the patient according to the methods of the invention is an antibody. In some embodiments, the binding agent is operably linked to a toxin. Non-limiting examples of such toxins are described above.

As used herein, the term "therapeutically effective amount" is used to denote known treatments of a drug at dosages and for periods of time effective to kill a damaged cell. Administration may be by any route including, without limitation, intravenous, parenteral, oral, sublingual, transdermal, topical, intranasal, intraocular, intravaginal, intrarectal, intraarterial, intramuscular, subcutaneous, and intraperitoneal.

As a physician will determine, the dose and dosage regimen of a binding agent, drug, and/or therapeutic composition in accordance with the invention, will depend mainly on the degree of symptoms of the disease or cancer, the type of drug used (e.g., chemotherapeutic agent, radiotherapeutic agent, or antibiotic), the patient (e.g., the patient's gender, age, and/or weight), the patient's history, and the patient's response to treatment. The doses of binding agent, drug, and/or therapeutic composition may be single doses or multiple doses. If multiple doses are employed, the frequency of administration (schedule) will depend, for example, on the patient, type of response, and type of drug used. Administration once a week may be effective for some patients; whereas for others, daily administration or administration every other day or every third day may be effective. The practitioner will be able to ascertain upon routine experimentation, which route of administration and frequency of administration are most effective in any particular case.

In yet another aspect, the invention features a method for detecting a multidrug resistant cell in a patient. The method includes administering a binding agent that specifically binds to an HSC70 protein to a patient suspected of comprising a multidrug resistant cell, wherein the binding agent is operably linked to a label that is detectable by a medical imaging device or system and examining the patient with the medical imaging device or system. According to this method, the medical imaging device or system detects the binding agent (e.g., an antibody) specifically bound to the cell surface of a multidrug resistant cell in the patient.

Medical imaging devices and systems are known, as are labels that are detectable by such systems. As discussed above, one non-limiting example of such a system and label is an X-ray machine which can detect radiolabeled binding agents. Other non-limiting examples of medical imaging systems include (a) X-ray based Computer Tomography (CT), positron emission tomography (PET), and new combinations and improvements on these technologies (PET+CT, spiral CT, single photon emission CT (SPECT), high resolution PET (microPET), and immunoscintigraphy (using radiolabeled antibodies (Czernin et al., *Ann. Rev. Med.* 53:89–112, 2002; Goldenberg, D. M., *Cancer* 80(12): 2431–2435, 1997; Langer, S. G. et al. *World J. Surg.* 25: 1428–1437, 2001; Middleton et al., *Postgrad Med.* 111(5): 89–90, 93–6, 2002); (b) magnetic resonance imaging (MRI) (Helbich, T. H., *J. Radiol.* 34: 208–219, 2000; Langer, S. G.

et al., *World J. Surg.* 25: 1428–1437, 2001; Nabi et al., *Oncol. J. Nuclear Med. Technol.* 30(1): 3–9, 2002); ultrasonic imaging (US) (Harvey, C. J. et al., *Adv. Ultrasound Clin. Radiol.* 57: 157–177, 2002; Langer, S. G. et al., *World J. Surg.* 25: 1428–1437, 2001); (c) fiber optic endoscope (Shelhase D. E., *Curr. Opin. Pediatr.* 14: 327–33, 2002); (d) gamma scintillation detectors (detect gamma emitters, e.g. 192-Ir), and beta scintillation detectors (detect beta emitters, eg., 90-Sr/Y) (Hanefeld, C. et al., *Circulation* 105: 2493–6, 2002).

In certain embodiments, the patient is a human. The patient may be, for example, a patient suffering from a disease caused by the presence of the multidrug resistant cell. For example, the patient may be suffering from cancer caused by a multidrug resistant neoplastic cells. Such a multidrug resistant neoplastic cell includes, without limitation, an ovarian cancer cell, and myeloma cancer cell, a lymphoma cancer cell, a melanoma cancer cell, a sarcoma cancer cell, a leukemia cancer cell, a retinoblastoma cancer cell a hepatoma cancer cell, a glioma cancer cell, a mesothelioma cancer cell, or a carcinoma cancer cell.

In some embodiments, the multidrug resistant cell is a damaged cell, and the patient is suffering from a disease caused by the presence of such a multidrug resistant damaged cell. Non-limiting ways in which a cell may be damaged include infection by a pathogen, or damaged by necrosis. In particular embodiments, the damaged cell is infected with a pathogen (e.g., a virus, parasite, or bacterium). For example, the patient may be suffering from tuberculosis caused by a multidrug resistant strain of *Mycobacterium tuberculosis*.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); Handbook Of Experimental Immunology, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

4.2 HSC70 Antibodies

The invention provides antibodies directed against HSC70 for use in detection, imaging and treatment of cancers and damaged (e.g., pathogen-infected) cells. Anti-HSC70 antibodies for use in the invention are available from several commercial vendors. For example, CHEMICON (Temecula, Calif.) and ABR-Affinity BioReagents (Golden, Colo.) both produce such anti-human HSC70 mouse monoclonal and/or rabbit polyclonal antibodies.

The term "antibody" is used in the broadest sense and specifically covers single anti-HSC70 monoclonal and polyclonal antibodies, as well as anti-HSC70 antibody fragments (e.g., Fab, F(ab)2, and Fv) and anti-HSC70 antibody compositions with polyepitopic specificity (including binding and non-binding antibodies). The term "monoclonal antibody" as used herein refers to an antibody obtained from a population of substantially homogeneous antibodies, i.e., the individual antibodies comprising the population are identical except for possible naturally occurring mutations that may be present in minor-amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. Novel monoclonal antibodies or fragments thereof mean in principle all immunoglobulin classes such as IgM, IgG, IgD, IgE, IgA or their subclasses such as the IgG subclasses or mixtures thereof. IgG and its subclasses are included, such as IgG1, IgG2, IgG2a, IgG2b, IgG3 or IgGM. The IgG subtypes IgG1/kappa and IgG 2b/kapp are also included as embodiments.

The monoclonal antibodies herein include hybrid and recombinant antibodies produced by splicing a variable (including hypervariable) domain of an anti-HSC70 antibody with a constant domain (e.g., "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab)2, and Fv), so long as they exhibit the desired biological activity. (See, e.g., U.S. Pat. No. 4,816,567 and Mage & Lamoyi, in *Monoclonal Antibody Production Techniques and Applications*, pp.79–97 (Marcel Dekker, Inc.), New York (1987)). Thus, the modified "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554 (1990), for example.

"Humanized" forms of non-human (e.g., murine) antibodies are specific chimeric immunoglobulins, immunoglobulin chains or fragments thereof (such as Fv, Fab, Fab', F(ab)2 or other antigen-binding subsequences of antibodies) which contain minimal sequence derived from non-human immunoglobulin. For the most part, humanized antibodies are human immunoglobulins (recipient antibody) in which residues from the complementary determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues that are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

HSC70 or anti-HSC70 monoclonal antibodies or fragments thereof mean in principle all immunoglobulin classes such as IgM, IgG, IgD, IgE, IgA or their subclasses such as the IgG subclasses or mixtures thereof. IgG and its subclasses are, such as IgG1, IgG2, IgG2a, IgG2b, IgG3 or IgGM. The IgG subtypes IgG1/kappa and IgG 2b/kapp are included as embodiments. Fragments which may be mentioned are all truncated or modified antibody fragments with one or two antigen-complementary binding sites which show high binding and binding activity toward mammalian HSC70, such as parts of antibodies having a binding site which corresponds to the antibody and is formed by light and heavy chains, such as Fv, Fab or F(ab')2 fragments, or single-stranded fragments. Truncated double-stranded fragments such as Fv, Fab or F(ab')2 are. These fragments can be obtained, for example, by enzymatic means by eliminating the Fc part of the antibody with enzymes such as papain or pepsin, by chemical oxidation or by genetic manipulation of the antibody genes. It is also possible and advantageous to use genetically manipulated, non-truncated fragments. The anti-HSC70 antibodies or fragments thereof can be used alone or in mixtures.

The novel antibodies, antibody fragments, mixtures or derivatives thereof advantageously have a binding affinity for HSC70 with a dissociation constant value within a log-range of from about $1\times10^{-11}$ M (0.01 nM) to about $1\times10^{-8}$ M (10 nM), or about $1\times10^{-10}$ M (0.1 nM) to about $3\times10^{99}$ M (3 nM).

The antibody genes for the genetic manipulations can be isolated, for example from hybridoma cells, in a manner known to the skilled worker. For this purpose, antibody-producing cells are cultured and, when the optical density of the cells is sufficient, the mRNA is isolated from the cells in a known manner by lysing the cells with guanidinium thiocyanate, acidifying with sodium acetate, extracting with phenol, chloroform/isoamyl alcohol, precipitating with isopropanol and washing with ethanol. cDNA is then synthesized from the mRNA using reverse transcriptase. The synthesized cDNA can be inserted, directly or after genetic manipulation, for example by site-directed mutagenesis, introduction of insertions, inversions, deletions or base exchanges, into suitable animal, fungal, bacterial or viral vectors and be expressed in appropriate host organisms. Preference is given to bacterial or yeast vectors such as pBR322, pUC18/19, pACYC184, lambda or yeast mu vectors for the cloning of the genes and expression in bacteria such as *E. coli* or in yeasts such as *Saccharomyces cerevisiae*.

The invention furthermore relates to cells that synthesize HSC70 antibodies. These include animal, fungal, bacterial cells or yeast cells after transformation as mentioned above. They are advantageously hybridoma cells or trioma cells, preferably hybridoma cells. These hybridoma cells can be produced, for example, in a known manner from animals immunized with HSC70 and isolation of their antibody-producing B cells, selecting these cells for HSC70-binding antibodies and subsequently fusing these cells to, for example, human or animal, for example, mouse mylemoa cells, human lymphoblastoid cells or heterohybridoma cells (see, e.g., Koeler et al., (1975) *Nature* 256: 496) or by infecting these cells with appropriate viruses to produce immortalized cell lines. Hybridoma cell lines produced by fusion are particularly useful, mouse hybridoma cell lines are very useful. The hybridoma cell lines of the invention secrete antibodies of the IgG type. The binding of the mAb antibodies of the invention, bind with high affinity to HSC70.

The invention further includes derivates of these anti-HSC70, which preferably retain their HSC70-binding activity while altering one or more other properties related to their use as a pharmaceutical agent, e.g., serum stability or efficiency of production. Examples of such antiHSC70 antibody derivatives include peptides, peptidomimetics derived from the antigen-binding regions of the antibodies, and antibodies, fragments or peptides bound to solid or liquid carriers such as polyethylene glycol, glass, synthetic polymers such as polyacrylamide, polystyrene, polypropylene, polyethylene or natural polymers such as cellulose, Sepharose or agarose, or conjugates with enzymes, toxins or radioactive or nonradioactive markers such as $^3$H, $^{123}$I, $^{125}$I, $^{131}$I, $^{32}$P, $^{35}$S, $^{14}$C, $^{51}$Cr, $^{57}$Co, $^{55}$Fe, $^{59}$Fe, $^{90}$Y, $^{99}$mTc (metastable isomer of Technetium 99), $^{75}$Se, or antibodies, fragments or peptides covalently bonded to fluorescent/chemiluminescent labels such as rhodamine, fluorescein, isothiocyanate, phycoerythrin, phycocyanin, fluorescamine, metal chelates, avidin, streptavidin or biotin.

The novel antibodies, antibody fragments, mixtures and derivatives thereof can be used directly, after drying, for example freeze drying, after attachment to the abovementioned carriers or after formulation with other pharmaceutical active and ancillary substances for producing pharmaceutical preparations. Examples of active and ancillary substances which may be mentioned are other antibodies, antimicrobial active substances with a microbiocidal or microbiostatic action such as antibiotics in general or sulfonamides, antitumor agents, water, buffers, salines, alcohols, fats, waxes, inert vehicles or other substances customary for parenteral products, such as amino acids, thickeners or sugars. These pharmaceutical preparations are used to control diseases, preferably to control arthritic disturbances, advantageously disturbances of joint cartilage.

The anti-HSC70 antibodies of the invention can be administered orally or parenterally subcutaneously, intramuscularly, intravenously or interperitoneally.

The antibodies, antibody fragments, mixtures or derivatives thereof can be used in therapy or diagnosis directly or after coupling to solid or liquid carriers, enzymes, toxins, radioactive or nonradioactive labels or to fluorescent/chemiluminescent labels as described above. HSC70 can be detected on a wide variety of cell types—particularly neoplastic cells.

The human HSC70 monoclonal antibody of the present invention may be obtained as follows. Those of skill in the art will recognize that other equivalent procedures for obtaining HSC70 antibodies are also available and are included in the invention.

First, a mammal is immunized with human HSC70. Purified human HSC70 is commercially available from Sigma (St. Louis, Mo., catalog A6152), as well as other commercial vendors. Human HSC70 may be readily purified from human placental tissue. Furthermore, methods of immunoaffinity purification for obtaining highly purified HSC70 immunogen are known (see, e.g., Vladutiu et al., (1975) 5: 147–59 *Prep. Biochem.*). The mammal used for raising anti-human HSC70 antibody is not restricted and may be a primate, a rodent such as mouse, rat or rabbit, bovine, sheep, goat or dog.

Next, antibody-producing cells such as spleen cells are removed from the immunized animal and are fused with myeloma cells. The myeloma cells are well-known in the art (e.g., p3×63-Ag8-653, NS-0, NS-1 or P3U1 cells may be used). The cell fusion operation may be carried out by a well-known conventional method.

The cells, after being subjected to the cell fusion operation, are then cultured in HAT selection medium so as to select hybridomas. Hybridomas, which produce antihuman monoclonal antibodies, are then screened. This screening may be carried out by, for example, sandwich ELISA (enzyme-linked immunosorbent assay) or the like in which the produced monoclonal antibodies are bound to the wells to which human HSC70 is immobilized. In this case, as the secondary antibody, an antibody specific to the immunoglobulin of the immunized animal, which is labeled with an enzyme such as peroxidase, alkaline phosphatase, glucose oxidase, beta-D-galactosidase or the like, may be employed. The label may be detected by reacting the labeling enzyme with its substrate and measuring the generated color. As the substrate, 3,3-diaminobenzidine, 2,2-diaminobis-o-dianisidine, 4-chloronaphthol, 4-aminoantipyrine, o-phenylenediamine or the like may be produced.

By the above-described operation, hybridomas, which produce anti-human HSC70 antibodies, can be selected. The selected hybridomas are then cloned by the conventional limiting dilution method or soft agar method. If desired, the cloned hybridomas may be cultured on a large scale using a serum-containing or a serum free medium, or may be inoculated into the abdominal cavity of mice and recovered from ascites, thereby a large number of the cloned hybridomas may be obtained.

From among the selected anti-human HSC70 monoclonal antibodies, those that have an ability to bind cell surface HSC70 are then chosen for further analysis and manipulation.

The monoclonal antibodies herein further include hybrid and recombinant antibodies produced by splicing a variable (including hypervariable) domain of an anti-HSC70 antibody with a constant domain (e.g., "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab)2, and Fv), so long as they exhibit the desired biological activity. (See, e.g., U.S. Pat. No. 4,816,567 and Mage & Lamoyi, in *Monoclonal Antibody Production Techniques and Applications*, pp.79–97 (Marcel Dekker, Inc.), New York (1987)).

Thus, the term "monoclonal" indicates that the character of the antibody obtained is from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554 (1990), for example.

"Humanized" forms of non-human (e.g., murine) antibodies are specific chimeric immunoglobulins, immunoglobulin chains or fragments thereof (such as Fv, Fab, Fab', F(ab)2 or other antigen-binding subsequences of antibodies) which contain minimal sequence derived from non-human immunoglobulin. For the most part, humanized antibodies are human immunoglobulins (recipient antibody) in which residues from the complementary determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues that are found neither in the recipient antibody nor in the imported CDR or FR sequences. These modifications are made to further refine and optimize antibody performance. In general, the humanized antibody comprises substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also comprises at least a portion of an immunoglobulin constant region (Fc), typically that of a human immunoglobulin.

Methods for humanizing non-human antibodies are well known in the art. Generally, a humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers (Jones et al., (1986) *Nature* 321: 522–525; Riechmann et al., (1988) *Nature*, 332: 323–327; and Verhoeyen et al., (1988) *Science* 239: 1534–1536), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., (1993) *J. Immunol.*, 151:2296; and Chothia and Lesk (1987) *J. Mol. Biol.*, 196:901). Another method uses a particular framework derived from the consensus sequence of all human antibodies of a particular subgroup of light or heavy chains. The same framework may be used for several different humanized antibodies (Carter et al., (1992) *Proc. Natl. Acad. Sci.* (*USA*), 89: 4285; and Presta et al., (1993) *J. Immunol.*, 151:2623).

It is further important that antibodies be humanized with retention of high affinity for the antigen and other favorable biological properties. To achieve this goal, according to a method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human antibodies directed against HSC70 are also included in the invention. Such antibodies can be made, for example, by the hybridoma method. Human myeloma and mouse-human heteromyeloma cell lines for the production of human monoclonal antibodies have been described, for example, by Kozbor (1984) *J. Immunol.*, 133, 3001; Brodeur, et al., *Monoclonal Antibody Production Techniques and Applications*, pp.51–63 (Marcel Dekker, Inc., New York, 1987); and Boerner et al., (1991) *J. Immunol.*, 147: 86–95. Specific methods for the generation of such human antibodies using, for example, phage display, transgenic mouse technologies and/or in vitro display technologies, such as ribosome display or covalent display, have been described (see Osbourn et al. (2003) *Drug Discov. Today* 8: 845–51; Maynard and Georgiou (2000) *Ann. Rev. Biomed. Eng.* 2: 339–76; and U.S. Pat. Nos. 4,833,077; 5,811,524; 5,958,765; 6,413,771; and 6,537,809.

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such gem-line mutant mice will result in the production of human antibodies upon antigen challenge (see, e.g., Jakobovits et al., (1993) *Proc. Natl. Acad. Sci*. (*USA*), 90: 2551; Jakobovits et al., (1993) *Nature,* 362:255–258; and Bruggermann et al., (1993) *Year in Immuno.,* 7:33).

Alternatively, phage display technology (McCafferty et al., (1990) *Nature,* 348: 552–553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats (for review see, e.g., Johnson et al., (1993) *Curr. Opin. in Struct. Bio.*, 3:564–571). Several sources of V-gene segments can be used for phage display. For example, Clackson et al., ((1991) *Nature,* 352: 624–628) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., ((1991) *J. Mol. Biol.*, 222:581–597, or Griffith et al., (1993) *EMBO J.,* 12:725–734).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (see Marks et al., (1992) *Bio/Technol.*, 10:779–783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., ((1993) *Nucl. Acids Res.,* 21:2265–2266).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e., the epitope governs (imprints) the choice of partner. When the process is repeated in order to replace the remaining rodent V domain, a human antibody is obtained (see PCT WO93/06213, published 1 Apr. 1993). Unlike traditional humanization of rodent antibodies by CDR grafting, this technique provides completely human antibodies, which have no framework or CDR residues of rodent origin.

By using the above-described monoclonal antibody of the present invention, human HSC70 in a sample can be detected or quantified. The detection or quantification of the human HSC70 in a sample can be carried out by an immunoassay utilizing the specific binding reaction between the monoclonal antibody of the present invention and human HSC70. Various immunoassays are well-known in the art and any of them can be employed. Examples of the immunoassays include sandwich method employing the monoclonal antibody and another monoclonal antibody as primary and secondary antibodies, respectively, sandwich methods employing the monoclonal antibody and a polyclonal antibody as primary and secondary antibodies, staining methods employing gold colloid, agglutination method, latex method and chemical luminescence. Among these, especially is sandwich ELISA. As is well-known, in this method, a primary antibody is immobilized on, for example, the inner wall of a well and then a sample is reacted with the immobilized primary antibody. After washing, a secondary antibody is reacted with the antigen-antibody complex immobilized in the well. After washing, the immobilized secondary antibody is quantified. As the primary antibody, an antibody specifically reacts with human HSC70 is preferably employed.

The quantification of the secondary antibody may be carried out by reacting a labeled antibody (e.g., enzyme-labeled antibody) specific to the immunoglobulin of the animal from which the secondary antibody was obtained with the secondary antibody, and then measuring the label. Alternatively, a labeled (e.g., enzyme-labeled) antibody is used as the secondary antibody and the quantification of the secondary antibody may be carried out by measuring the label on the secondary antibody.

4.3 HSC70 Binding Agents

In another aspect, the invention provides a binding agent that specifically binds to a HSC70 protein or fragment thereof. As used herein, "specifically binds" means that a binding agent recognizes and binds to a HSC70 protein or fragment thereof, but does not substantially recognize and bind to other molecules in a sample. Thus, a binding agent of the invention specifically binds to the surface of a MDR cell that expresses HSC70 on its cell surface. A useful binding agent forms an association with the HSC70 protein with an affinity of at least at least about $10^6$ M−1, or at least about $10^7$ M−1, or at least about $10^8$ M−1, or at least about $10^9$ M−1 either in water, under physiological conditions, or under conditions which approximate physiological conditions with respect to ionic strength, e.g., 140 mM NaCl, 5 mM $MgCl_2$. As used herein, a "binding agent" is a molecule that specifically binds or attaches to a HSC70 protein or fragment thereof.

A binding agent need not be any particular size or have any particular structure so long as it specifically binds to the HSC70 protein or fragment thereof. Thus, a "binding agent" is a molecule that specifically binds to or attaches to any region (e.g., three dimensional structure, amino acid sequence, or particular small chemical groups) so long as it specifically binds to the HSC70 protein or fragment thereof. Non-limiting examples of binding agents include natural ligands (such as hormones or GTP), as well as synthetic small molecules, chemicals, nucleic acids, peptides, and proteins such as hormones, antibodies, and portions thereof.

There are a number of examples of non-antibody HSC70 binding agents known in the art. There are a number of examples of non-antibody HSC70 binding agents known in the art. For example, Alzheimer's tau protein (Shimura et al. (2003) *J. Biol. Chem.* (Nov. 10, 2003 e-publication); BAG-1 (Takamura et al. (2003) *Int. J. Oncol.* 23: 1301–8); small glutamine-rich tetratricopeptide repeat-containing protein (SGT) (Tobaben et al. *J. Biol. Chem.* 77: 7254–60); (aa 642–658) of rotavirus VP5 protein (Zarate et al. (2003) *J. Virol.* 77: 7254–60); auxilin (Jiang et al. (1997) *J. Biol. Chem.* 272: 6141–5); and the immunosuppressant 5-deoxyspergualin (DSG) (Nadler et al. (1998) *Biochem. Biophys. Res. Comm.* 253: 176–80).

4.4 HSC70-Targeted Diagnostics

The invention further allows the early identification of patients having such MDR neoplastic or damaged cells. For example, where the patient identified as having such cells is a patient in remission of cancer or is being treated for cancer (e.g., a patient suffering from breast cancer, ovarian cancer, prostate cancer, leukemia, etc.), the invention allows identification of these patients prior to resurgence and/or progression of their cancer, as well as allows the monitoring of these patients during treatment with a drug, such that the treatment regimen can be altered. Similarly, where the patient identified as having such cells is an asymptomatic patient who is being treated for an infectious disease, or had received treatment for an infectious disease (e.g., hepatitis B), the invention allows identification of these patients prior to resurgence of symptoms, as well as allows the monitoring of these patients during treatment with a drug, such that the treatment regimen can be altered if such MDR cells are detected. Furthermore, diagnostic applications of the invention allow early diagnosis and imaging of neoplastic, MDR neoplastic or damaged (e.g., pathogen-infected) cells using the cell surface HSC70 marker The diagnostic applications of the invention include probes and other detectable agents that are joined to a HSC70 binding agent, such as an anti-HSC70 antibody. As used herein, the term "detectably labeled" means that a binding agent of the invention is operably linked to a moiety that is detectable. "Operably linked" means that the moiety is attached to the binding agent by either a covalent or non-covalent (e.g., ionic) bond. Methods for creating covalent bonds are known (see general protocols in, e.g., Wong, S. S., Chemistry of Protein Conjugation and Cross-Linking, CRC Press 1991; Burkhart et al., The Chemistry and Application of Amino Crosslinking Agents or Aminoplasts, John Wiley & Sons Inc., New York City, N.Y. 1999).

In accordance with the invention, a detectably labeled binding agent of the invention includes a binding agent that is conjugated to a detectable moiety. Another detectably labeled binding agent of the invention is a fusion protein, where one partner is the binding agent and the other partner is a detectable label. Yet a further non-limiting example of a detectably labeled binding agent is a first fusion protein comprising a binding agent and a first moiety with high affinity to a second moiety, and a second fusion protein comprising a second moiety and a detectable label. For example, a binding agent that specifically binds to a HSC70 protein may be operably linked to a streptavidin moiety. A second fusion protein comprising a biotin moiety operably linked to a fluorescein moiety may be added to the binding agent-streptavidin fusion protein, where the combination of the second fusion protein to the binding agent-streptavidin fusion protein results in a detectably labeled binding agent (i.e., a binding agent operably linked to a detectable label).

The detectable label of the invention is a moiety that can be tracked, and includes, without limitation, fluorophores (e.g., fluorescein (FITC), phycoerythrin, rhodamine), chemical dyes, or compounds that are radioactive, chemoluminescent, magnetic, paramagnetic, promagnetic, or enzymes that yield a product that may be colored, chemoluminescent, or magnetic. In particular embodiments, the detectable label is detectable to a medical imaging device or system. For example, where the medical imaging system is an X-ray machine, the detectable label that can be detected by the X-ray machine is a radioactive label (e.g., $^{32}P$). Note that a binding agent need not be directly conjugated to the detectable moiety. For example, a binding agent (e.g., a mouse anti-human HSC70 antibody) that is itself specifically bound by a secondary detectable binding agent (e.g., a FITC labeled goat anti-mouse secondary antibody) is operably linked to a detectable moiety (i.e., the FITC moiety).

In some embodiments, measuring the level of expression of a HSC70 protein on the surface of the test damaged cell includes contacting the intact test damaged cell with a detectable binding agent that specifically binds to a HSC70 protein. For example, where the detectable binding agent is detectably labeled by being operably linked to a fluorophore, cells staining with the fluorophore (i.e., those that are specifically bound by the binding agent) can be identified by fluorescent activated cell sorter analysis (see Examples), or by routine fluorescent microscopy of clinical specimens prepared on slides.

Medical imaging devices and systems are known, as are labels that are detectable by such systems. As discussed above, one non-limiting example of such a system and label is an X-ray machine which can detect radiolabeled binding agents. Other non-limiting examples of medical imaging systems include (a) X-ray based Computer Tomography (CT), positron emission tomography (PET), and new combinations and improvements on these technologies [(PET+CT, spiral CT, single photon emission CT (SPECT), high resolution PET (microPET), and immunoscintigraphy (using radiolabeled antibodies (Czernin, J. and M. E. Phelps (2002) *Annual Reviews of Medicine* 53:89–112; Goldenberg, D. M. (1997) *Cancer* 80 (12):2431–2435; Langer, S. G. et al. (2001) *World Journal of Surgery* 25:1428–1437; Middleton ML and Shell EG (2002) *Postgrad Med* 111(5):89–90, 93–6; (b) magnetic resonance imaging (MRI)(Helbich, T. H, (2002) *Journal of Radiology* 34:208–219; Langer, S. G. et al. (2001) *World Journal of Surgery* 25:1428–1437; Nabi, H. A. and Zubeldia, J. M. (2002) *Oncology Journal of Nuclear Medicine Technology* 30 (1):3–9); ultrasonic imaging (US) (Harvey, C. J, et al. (2002) *Advances in Ultrasound Clinical Radiology* 57:157–177; Langer, S. G. et al. (2001) *World Journal of Surgery* 25:1428–1437); (c) fiber optic endoscope (Shelhase Del. (2002) *Curr Opin Pediatr* 14:327–33); (d) gamma scintillation detectors (detect gamma emitters, e.g. 192-Ir), and beta scintillation detectors (detect beta emitters, e.g. 90-Sr/Y) (Hanefeld C, Amirie, S. et al. (2002) *Circulation* 105:2493–6, 2002).

Labeled antibodies, and derivatives and analogs thereof, which specifically bind to HSC70 polypeptide can be used for diagnostic purposes to detect, diagnose, or monitor diseases and/or disorders associated with the aberrant expression of a cell surface HSC70. The invention provides for the detection of aberrant expression of cell surface HSC70 (a) assaying the expression of the polypeptide of interest in cells or cell surface membrane fractions of an individual using one or more antibodies specific to HSC70 and (b) comparing the level of gene expression with a standard gene expression level, whereby an increase or decrease in the assayed cell surface HSC70 expression level compared to the standard expression level is indicative of aberrant expression. For example, where multidrug resistance in a neoplastic cell is to be detected, the "standard expression level" to which comparison should be made is a nonmultidrug resistant neoplastic cell of the same or similar origin or cell type. Similarly, where neoplasia in a test cell is to be detected, the "standard expression level" to which comparison should be made is a non-neoplastic cell of the same or similar origin or cell type. Furthermore, where "damage" in a test cell (e.g., pathogen infection) is to be detected, the "standard expression level" to which comparison should be made is a non-damage cell (e.g., uninfected cell) of the same or similar origin or cell type.

With respect to cancer, the presence of a relatively high amount of cell surface HSC70 in biopsied tissue or test cell from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M., et al., (1985) *J. Cell. Biol.* 101:976–985); Jalkanen, M., et al. (1987) *J. Cell. Biol.* 105:3087–3096). Other antibody-based methods useful for detecting HSC70 protein expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^3$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of cell surface HSC70 in an animal, such as a mammal, e.g., a human. In one embodiment, diagnosis comprises: a) administering (for example, parenterally, subcutaneously, or intraperitoneally) to a subject an effective amount of a labeled anti-HSC70 antibody, or other HSC70 binding agent, which specifically binds to cell surface HSC70 in the animal; b) waiting for a time interval following administration for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

A HSC70-specific antibody or antibody portion which has been labeled with an appropriate detectable imaging moiety, such as a radioisotope (for example, $^{131}$I, $^{111}$In, $^{99m}$Tc), a radio-opaque substance, or a material detectable by nuclear magnetic resonance, is introduced (for example, parenterally, subcutaneously or intraperitoneally) into the mammal to be examined for a disorder. Generally, suitable radioisotopes for imaging and detection include radioisotopes that emit alpha, beta, or gamma radiation. Gamma radiation may be particularly easy to image using current technology. Examples are radioisotopes derived from Gallium, Indium, Technetium, Yttrium, Ytterbium, Rhenium, Platinum, Thallium, and Astatine, e.g., $^{67}$Ga, $^{111}$In, $^{99m}$TC, $^{90}$Y, $^{86}$Y, $^{169}$Yb, $^{188}$Re, $^{195m}$Pt, $^{201}$Ti, and $^{211}$At. It is understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which express cell surface HSC70 protein. Reagents and methods for tumor imaging in vivo (i.e., in situ) are known in the art and described in, for example, S. W. Burchiel et al. (1982) "Immunopharmacokinetics of Radiolabeled Antibodies and Their Fragments." (Chapter 13 in *Tumor Imaging. The Radiochemical Detection of Cancer*, S. W. Burchiel and B. A. Rhodes, eds., Masson Publishing Inc.). For example, antibody labels or markers for in vivo imaging of endokine alpha protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

Depending on several variables which can be optimized using routine practice, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In certain embodiment, monitoring of the disease or disorder is carried out by repeating the method for diagnosing the disease or disease, for example, one month after initial diagnosis, six months after initial diagnosis, one year after initial diagnosis, etc.

Significantly, the presence of the labeled anti-HSC70 antibody or other HSC70 binding can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

For example, in a specific embodiment, the anti-HSC70 antibody is labeled with a radioisotope and is detected in the patient using a radiation responsive surgical instrument (Thurston et al., U.S. Pat. No. 5,441,050). In another embodiment, the anti-HSC70 antibody is labeled with a fluorescent compound and is detected in the patient using a fluorescence responsive scanning instrument. In another embodiment, the anti-HSC70 antibody is labeled with a positron emitting metal and is detected in the patent using positron emission-tomography. In yet another embodiment, the anti-HSC70 antibody is labeled with a paramagnetic label and is detected in a patient using magnetic resonance imaging (MRI).

4.5 HSC70-Targeted Therapeutics

The invention takes advantage of the fact that HSC70 protein cell surface marker is present only in negligible levels on the surface of normal cells of the body, but occurs on the cell surface of neoplastic and, expecially, in multidrug resistant neoplastic cells. In contrast, other markers, and particularly the MDR markers such as P-glycoprotein and the multidrug resistance protein (MRP), are present at variable levels on the surface of many different normal cell and tissues, including high levels on the surface of liver, kidney, stem cells, and blood-brain barrier epithelial cells. Accordingly, the invention provides a highly specific way of targeting therapeutics to neoplastic and, particularly, multidrug resistant neoplastic, cells using a binding agent that binds to cell surface HSC70.

Therapeutic agents to be targeted to HSC70 by the methods of the invention include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Anti-HSC70 Antibodies

In one approach, anti-HSC70 antibodies specific to cell surface expressed HSC70 expressed on damaged (e.g., pathogen-infected), neoplastic, and MDR neoplastic cells are administered systemically to a patient with cancer. Adhesion of antibody to tumor cells results in tumor cell death by activation of the complement system (complement-mediated cytotoxicity) or by activation of T cells (antibody-dependent cell-mediated cytotoxicity). Other antibody-induced antitumor effects include induction of apoptosis, enhancement of the cytotoxic effects of a second agent (e.g., an anti-cancer chemotherapeutic drug), and induction of anti-idiotype network response. In certain embodiments, humanized anti-HSC70 antibodies may be utilized. Humanized antibodies avoid the potential problem of causing human patients to develop anti-animal (e.g., anti-mouse or anti-rat) antibodies. Humanized antibodies consist of human antibody containt the compelementarity-determining region from a nonhuman source.

Antibody based therapeutics have been used successfully in a number of cases. For example, Rituximab is a genetically engineered monoclonal anti-CD20 antibody used to treat non-Hodgkins lymphoma (NHL), a relatively common malignancy affecting both young and old populations. The CD20 antigen typically present on these B-cell lymphomas serves as an ideal targeting antigen because it is not present on plasma cells, B-cell precursors, stem cells, or dendritic (antigen-presenting) cells. The Rituximab antibody (or Rituxan) is neither shed nor internalized by NHL cells and it does not undergo modification following antigen binding. Rituximab was approved by the FDA in 1997 for the treatment of relapsed or refractory CD20-positive B-cell NHL and for low-grade or follicular type lymphoma (see Abou-Jawde et al. (2003) *Clin. Therap.* 25: 2121–37; and Kim (2003) *Am. J. Surg.* 186: 264–68). It functions by mediating antibody-dependent cytotoxicity, inhibiting cell growth, sensitizing chemoresistant cells to toxins and chemotherapy, and inducing apoptosis in a dose-dependent manner (White et al. (2001) *Annu. Rev. Med.* 52: 125–45; Press (1999) *Semin. Oncol.* 26(Suppl 14): 58–65).

Another example of an anti-tumor antigen antibody therapeutic is Alemtuzumab. Alemtuzumab is a humanized anti-CD52 monoclonal antibody approved by the FDA in 2001 for the treatment of patients with B-cell chronic lymphocytic leukemia (CLL), a prevalent form of adult malignancy (see Abou-Jawde et al. (2003) *Clin. Therap.* 25: 2121–37). Even though the function of CD52 is not well identified, Alemtuzumab has been shown to elicit tumor response even in the presence of bulky disease (Ferrajoli et al. (2001) *Expert Opin. Biol. Ther.* 1: 1059–1065).

Still another example of an anti-tumor antigen antibody therapeutic is Trastuzumab (also Herceptin), a recombinant humanized anti-HER 2 monoclonal antibody approved by the FDA in 1998 for the treatment of metastatic breast cancer (see Abou-Jawde et al. (2003) *Clin. Therap.* 25: 2121–37; and Kim (2003) *Am. J. Surg.* 186: 264–68). HER 2 is an epidermal growth factor receptor (EGFR) family member expressed by many breast cancers tumors and, accordingly, this antibody therapeutic is effective against solid tumors. Several randomized, controlled studies were conducted and showed efficacy and improved quality of life in HER2-positive breast cancer patients treated with Trastuzumab (Vogel et al. (2002) *J. Clin. Oncol.* 20: 719–26).

Finally, Cetuximab is a chimeric anti-HER1 monoclonal antibody that is effective in treating several HER1/erb-B1 expressing solid tumors, including colorectal, pancreatic, non-small cell lung cancer (NSCLC), and head and neck cancers (see, e.g., O'dwyer et al. (2002) *Semin. Oncol.* 29(Suppl. 14): 10–17). Cetuximab competes for the binding of the EGFR and removes receptor from the cell membrane by stimulating internalization and thereby dirsuptin the cellular process responsible for proliferation growth and metastasis (see Abou-Jawde et al. (2003) *Clin. Therap.* 25: 2121–37).

HSC70— Targeted Antibody and Ligand Conjugates

In addition to the 'naked' antibody approach described above, antibodies can be conjugated, or otherwise "operably linked" to biological or chemical toxins or radioisotopes. An anti-HSC70 antibody or antibody fragment thereof may be conjugated or otherwise operably linked to a therapeutic moiety such as a cytotoxin, e.g., a cytostatic or cytocidal agent, a therapeutic agent or a radioactive metal ion. "Operably linked" means that the therapeutic moiety is attached to the binding agent by either a covalent or non-covalent (e.g., hydrophobic or ionic) bond. Methods for creating covalent bonds are known (see general protocols in, e.g., Wong, S. S., Chemistry of Protein Conjugation and Cross-Linking, CRC Press 1991; Burkhart et al., The Chemistry and Application of Amino Crosslinking Agents or Aminoplasts, John Wiley & Sons Inc., New York City, N.Y. 1999). Following systemic administration, the therapy is targeted to the cancer cell (or MDR cancer cell or damaged (e.g., pathogen-infected) cell) by the antibody.

The invention further includes HSC70-targeted agents made up of a HSC70 targeting element and a toxic agent, such as a biological toxin, a chemical toxin or a radioisotope. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Biological toxins have been conjugated, or genetically fused in frame, to antibodies, and other tumor marker-localizing agents. These biological toxins include ricin, diphtheria toxin and Pseudomonas exotoxin. Following binding to cell surface HSC70, the toxins generally cross the cell membrane, and may then be processed, before killing the targeted cell. The toxic effect is typically due to inhibition of protein-synthesis by the active biological toxin.

For example, in one embodiment, anti-HSC70 antibodies are conjugated to cobra venom factor. In accordance with the invention, HSC70 specific antibodies conjugated to cobra venom factor are used to treat cancer, including especially multidrug resistant cancer in a human.

Methods of conjugating antibodies to cobra venom factor are taught in U.S. Pat. No. 5,773,243. In some embodiments, the binding agent is an immunotoxin (e.g., an antibody-toxin conjugate or antibody-drug conjugate). Non-limiting examples of immunotoxins include antibody-anthracycline conjugates (Braslawsky G. R. et al., European Patent No. EP0398305), antibody-cytokine conjugates (Gilles S. D., PCT Publication No. WO9953958), and monoclonal antibody-PE conjugates (Roffler S. R. et al., Cancer Res. 51: 4001–4007, 1991).

Techniques for conjugating other therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", *Immunol. Rev.*, 62:119–58 (1982); each of which is incorporated herein by reference. Alternatively, an antibody can be conjugated to a second antibody to form an antibody heteroconjugate as described by Segal in U.S. Pat. No. 4,676,980, which is incorporated herein by reference.

Drug Attachment

A number of approaches to drug and therapeutics attachment and release have been described in the literature, and the strategies employed in soluble polymer-drug conjugates have been recently reviewed (Soyez, et al., (1966) *Adv. Drug Del. Rev.* 21:81–106). The chemistry of many of these conjugation methods is described in textbooks (e.g., Ref. Wong (1991) *CRC Press*, Boca Raton, Fla.), site of the attachment to the antibody.

The most used site is that of the $\epsilon$-amino groups of the lysine residues, as these are chemically convenient to use, either by amide bond forming reagents such as carbodiimides or by heterobifunctional agents such as N-succinimidy1-3-(2-pyridyldithio) propionate (SPDP) (Carlsson, et al., (1978) *Biochem J.* 173:723–737) which can introduce reactive thiol groups. Antibodies have a variable number of lysine residues, which are spread over the whole of the antibody, and there is no evidence for any subset of more reactive residues. Consequently, lysine residues at the active site are as likely to be modified as any other residues leading to loss of antibody activity, and the greater the number of lysine residues modified, the greater the likelihood of loss of binding. Linking to lysine $\epsilon$-amino groups can also have other effects. Firstly by neutralizing a positive charge on the protein could have structural effects, or affect the solubility of the antibody (Hudecz, et al., (1990) *Bioconjug. Chem.* 1: 197–204) although this can be overcome by using a reagent such as 2-iminothiolane which provides a thiol functionality without altering the charge (Jue, et al., (1978) *Biochemistry* 17:5399–5406). Finally, the number of lysine residues modified is statistical, so a range of modified residues is provided within a population of antibody molecules, leading to a variable amount of drug attached and loss of binding activity within a single preparation (Firestone, et al., (1996) *BR96-Dox, J. Control* 39:251–259).

A second site for modification is the sugar residues attached to the hinge region of the antibody. As this is a site of unique chemical reactivity situated away from the antibody binding site this is a useful area for attachment. This has been exploited by several groups by periodate oxidation of the sugars to provide aldehyde groups (O'Shanessy, et al., (1984) *Immunol. Lett.* 8:273–277; O'Shanessy, et al., (1987) *J. Immunol. Methods* 99:153–161; and Rodwell, et al., (1986) *Proc. Natl. Acad. Sci. USA* 83:2632–2636) which can be used in a number of coupling procedures. Aldehyde groups can also be generated on immunoglobulins by an enzymic reaction involving neuraminidase and glucose oxidase (Rodwell, et al., (1986) *Proc. Natl. Acad. Sci. USA* 83:2632–2636 and Stan, et al., (1999) *Cancer Res.* 59:115–121). Antibodies have also been modified by genetic engineering to produce new oligosaccharides sites which are reported to be more favourably located for attachment of carrier-drug molecules (Qu, et al., (1998) *J. Immunol. Methods* 213:131–144).

The third major possibility for attachment is through internal disulphide bonds within the antibody. Disulphide linkages play an important role in the structure of antibodies, providing both interchain and intrachain linkages. The intrachain linkages which stabilize the antibody domain structure can be selectively cleaved by dithiothreitol without affecting the interchain disulphide holding the antibody chains together. This procedure has been exploited by (Willner et al., (1993) *Bioconjug. Chem.* 4:521–527) to produce more soluble conjugates with better binding activity and with a defined number of drug molecules per antibody molecule. Surprisingly, this procedure had no detectable effect on the stability and immunoreactivity of the antibody. There are a maximum number of intrachain disulphide sites which can be exploited depending on the antibody subclass. A branched chain hydrazone linker has not also been described to exploit this binding site further, by doubling the number of drug molecules which can be chemically attached (King, et al., (1999) *Bioconjug. Chem.* 10:279–288).

Antibody fragments have also been used in a number of drug targeting studies. From a conjugation viewpoint the Fab' fragment is particularly convenient, bearing a single free sulphydryl group which can be readily used for attachment to drugs or other macromolecules (Hashida, et al., (1984) *J. Appl. Biochem.* 6:56–63).

One of the simplest methods of attachment is the use of peptide bond forming reagents such as carbodiimides or active esters which have been used to attach carboxyl-bearing drug such as methotrexate (MTX). Early work with polylysine conjugates, has shown that biodegradable MTX-poly($-_L$-lysine) shows some cytotoxicity, but that MTX-poly ($-_D$-Lysine) is non-toxic, suggesting that free drug is released through cleavage of the polymer (Ryser, et al., (1980) *Cancer* 45:1207–1211). In that case we would also expect biological molecules such as albumin and immunoglobulins to be cleaved to release free drug. Both MTX-immunoglobulin (Kanellos, et al., (1985) *J. Natl. Cancer Inst.* 75:319–332) and MTX-HSA-Immunoglobulin (Garnett, et al., (1983) *Int. J. Cancer* 31:661–670) conjugates have been reported using this principal. These reactions do not cleanly produce a single product, a mixture of labile ester and stable amide bonds being formed (Endo, et al., (1988) *Cancer Res.* 48:3330–3335 and Hudecz, et al., (1992) *Biomed. Chromatogr.* 6:128–132). The ester-linked material can form up to 24% of the conjugated drug, and is gradually released from the conjugate by hydrolysis in storage at 4° C. over 20 days (Hudecz, et al., (1992) *Biomed. Chromatogr.* 6:128–132). The inhibition of conjugate cytotoxicity by ammonium chloride, and the lysosomal protease inhibitors leupeptin and E64 (Garnett, et al., (1985) *Anti-Cancer Drug Design* 1:3–12) suggested that the free drug was being released through degradation in a lysosomal compartment. However, detailed studies on the release of MTX from HSA-MTX conjugates (Fitzpatrick et al., (1995) *Anti-Cancer Drug Design* 10:11–24) have shown that the amount of low-molecular weight drug released by rat liver tritosomes is very low (5.6% in 55 h). Further, only about 10% of the material released was free MTX, the rest being amino acids are not readily cleaved from the drug enzymatically and are significantly less cytotoxic than unmodified methotrexate (Rosowsky, et al., (1984) *J. Med. Chem.* 27:888–893). Conjugates designed to release these amino acid derivatives of MTX were also less cytotoxic than conjugates releasing free MTX. Release of MTX and MTX derivatives from antibody-MTX conjugates was much lower, estimated to be <0.05% over the same period, which was attributed to both the low substitution ratio for methotrexate (Rosowsky, et al., (1984) *J. Med. Chem.* 27:888–893) and the poor degradation of the Fab region of antibodies by tritosomes (Schneider, et al., (1981) *J. Cell. Biol.* 88:380–387). A linker which specifically releases free drug from conjugate is therefore a vital component of targeted drug conjugates. Various types of linkage have been reported.

Aldehyde/Schiff base linkages may also be used to link therapeutic agents to antibodies or other localizing agents. Sugar residues with vicinal hydroxyl groups can be converted into aldehyde groups by oxidation with periodate (O'Shanessy, et al., (1984) *Immunol. Lett.* 8:273–277). This enables sugar residues in polysaccharides such as dextran, or sugar moieties in drugs, e.g., nucleoside sugar groups in fluorouridine, or the amino sugar in daunomycin to have a more useful aldehyde group inserted. Aldehydes will readily react with hydrazides to form a hydrazone, or with amines to form a Schiff base. The Schiff base itself is relatively unstable (Cordes, et al., (1963) *J. Am. Chem. Soc.* 85:2843–2848), and can reform its starting materials so is usually reduced with a reagent such as sodium borohydride or sodium cyanoborohydride to stabilize the linkage. Dialdehydes such as glutaraldehyde can also be used to crosslink between drug and macromolecule, or between macromolecules, but in this case the linkage of the products is usually irreversible (Wong, (1991) *CRC Press* Boca Raton, Fla. 101–102). The use of glutaraldehyde as a cross-linking agent also has the disadvantage that it is a homobifunctional reagent, so unwanted cross-links and aggregates can be readily generated.

Sulphydryl linkages may also be used to link therapeutic agents to antibodies or other localizing agents. Disulphide linkages are found connecting the chains of plant toxins, and are essential for their activity (Masuho, et al., (1982) *J. Biochem.* 91:1583–1591) so that the enzymic A chain can dissociate from the binding chain and enter the cytoplasm. The necessity of this linkage suggests that this is a possible way of releasing drugs from antibody or polymer molecules in intracellular compartments. Conjugates of methotrexate to poly($_D$-lysine) through a disulphide linkage were shown to be cytotoxic (Shen, et al., (1985) *J. Biol. Chem.* 260: 10905–10908). Cleavage of these conjugates was shown to occur initially at the cell surface, but did not take place within the endosomal or lysosomal compartments (Feener, et al., (1990) *J. Biol. Chem.* 265:18780–18785). It was suggested that the Golgi apparatus was the most likely site of cleavage. Although cleavable intracellularly, this linkage was shown to be unstable in the circulation, and hindered disulphide bonds have therefore been developed to reduce this problem (Thorpe, et al., (1987) *Cancer Res.* 47:5924–5931 and Worrell, et al., (1986) *Anti-Cancer Drug Design* 1:179–188). For conjugates where a stable, chemically convenient coupling via a sulphydryl group is required a thioether bond is more stable and can be produced through the use of maleimide (Hashida, et al., (1984) *J. Appl. Biochem.* 6:56–63 and Lau, et al., (1995) *Bioorg. Med. Chem.* 3:1299–1304) or iodacetate (Rector, et al., (1978) *J. Immunol. Methods* 24:321–336) coupling reagents.

Acid-labile linkages may also be used to link therapeutic agents to antibodies or other localizing agents. Chemically labile linkages could be used to release drug in the presence of more acid conditions. These conditions can occur either in the tumour environment which is reported to be 0.5–1 pH unit more acidic than health tissue and blood (Lavie, et al., (1991) *Cancer Immunol. Immunther.* 33:223–230 and Ashby (1966) *Lancet* ii:312–315), or during passage through the endosomal/lysosomal compartment, where pH of 6–6.8 and 4.5–5.5, respectively, can be found. The major drawback to the use of an acid-labile linkage is that this is a rate-dependent phenomenon, where the rate of cleavage is proportional to pH: a 10-fold difference in rate can be expected for each pH unit decreased. This means that the hydrolysis will always be a compromise between a fast rate at low pH in the intracellular compartment, and a slow rate for serum stability.

The first acid sensitive linker described was the cis-aconityl linkage described by Shen and Ryser (Shen, et al., (1981) *Biochem. Biophys. Res. Commun.* 102:1048–1054. Daunomycin was first reacted with cis-aconitic anhydride, which was then subsequently coupled to poly-lysine using a water-soluble carbodiimide. This linkage was reported to have a half-life of less than 3 h at pH 4 and greater then 96 h at pH 6. However, only about 50% of the drug was released from an affi-gel matrix. This may be due to inappropriate binding of the gel matrix to the remaining cis-carboxyl group responsible for the acid-sensitive release from this linker. The optimum conditions for the use of this reagent have been described in detail by (Hudecz, et al., (1990) *Bioconjug. Chem.* 1:197–204). An improved version of this release mechanism has also been described by (Blättler, et al., (1985) *Biochemistry* 24:1517–1524), as a heterobifunctional agent for coupling of toxin molecules. In this method, the conjugation through the third carboxyl of the cis-aconitate has been replaced with a specific male-imido group which will eliminate the possibility of inactivation of the acid release properties of the cis-carbonyl group.

A range of acid-sensitive homo- and heterobifunctional agents originally prepared to give acid-sensitive release for toxin immunoconjugates have been described by Srinivasachar, based on ortho esters, acetals and ketals (Srinivasachur, et al., (1989) *Biochemistry* 28:2501–2509). These could also potentially be of use for constructing chemoimmunoconjugates. These reagents vary in their rate of hydrolysis at the pH found in intracellular compartments. Hydrazone linkages may also be used to link therapeutic agents to antibodies or other localizing agents.

Hydrazide derivatives are also acid labile and have been used to produce both vindesine and adriamycin conjugates (Laguzza, et al., (1989) *J. Med. Chem.* 32:548–555 and Greenfield, et al., (1990) *Cancer Res.* 50:6600–6607). In the former, (Laguzza, et al., (1989) *J. Med. Chem.* 32:548–555) vindesine was first reacted with hydrazine, and the hydrazide derivative then reacted with the oxidised sugar residue of antibody. In the adriamycin conjugate (Greenfield, et al., (1990) *Cancer Res.* 50:6600–6607), an SPDP hydrazine derivative, was prepared which was reacted with a thiolated antibody. In both of these conjugates low-molecular weight drug was released under acid conditions. In the former case, up to about 30% vinca hydrazide was released at pH 5.3 over 7 days at 37° C., in the latter case, unmodified adriamycin was released rapidly from the conjugate at pH 4.0–5.5. A study of different hydrazone derivatives of adriamycin has been reported (Kaneko, et al., (1991) *Bioconjug. Chem.* 2:133–141), which show that the acid instability of the various linkers is acylhydrazide>semicarbazide>carbonic acid dihydrazide>thiosemicarbazide>hydrazine carboxylate=arylhydrazide, all releasing adriamycin as the only product. With the exception of the arylhydrazide, all of these compounds were stable at pH 7.4. The acyl hydrazine released 85% of the theoretical amount of drug at pH 5.0, 37° C. in 3 h, and when conjugated to an anti-transferrin receptor antibody, was nearly as cytotoxic as free adriamycin. A maleimidocaproylhydrazone derivative has also been synthesized to provide a thioether-linked conjugate which is more stable in serum, and which can be readily coupled to reduced intrachain disulphide groups in antibodies (Firestone, et al., (1996) *BR96-Dox, J. Control* 39:251–259). Further long-chain arylhydrazide linkers for conjugation of anthracyclines have been described by (Lau, et al., (1995) *Bioorg. Med. Chem.* 3:1299–1304).

Enzymically degradable linkers may also be used to link therapeutic agents to antibodies or other localizing agents. The gold standard for attaching and releasing drugs from macromolecules is a linker which is stable in serum but can be cleaved intracellularly by specific enzymes. Linkers of this type have been described containing a variety of amino acids. Some of these linkers have been used in targeted drug conjugates with antibodies, but others only in polymer-drug conjugates. Cleavable amino acid pro-drugs of daunomycin (Dau) were first produced by Levin and Sela (Levin, et al., (1979) *FEBS Lett.* 98:119–122), although these were designated as low-molecular weight pro-drugs. The first systematic studies investigating amino acid sequences and lengths for lysosomal digestion were reported by (Masquelier et al. (1980) *J. Med. Chem.* 23:1166–1170). These studies identified an Ala-Leu-Dau derivative which could be converted back to the free drug by lysosomal hydrolases in 2 h. The activity was ascribed to a lysosomal dipeptidyl aminopeptidase. While these dipeptide derivatives were much less potent than Dau in vitro, they showed greater potency in vivo (Baurain, et al., (1980) *J. Med. Chem.* 23:1171–1174). Further work reported by this group (Trouet, et al., (1982) *Proc. Natl. Acad. Sci. USA* 79:626–629) resulted in conjugates in which daunorubicin was linked to succinylated serum albumin by a spacer arm of one to four amino acids. A minimum tri or peptide spacer was found to be essential for good release of drug. A release of 75% of free drug was achieved in 8 h with an albumin conjugate with an Ala-Leu-Ala-Leu-Dau linkage, which was stable in the presence of serum (only 2.5% drug released in 24 h). No drug was released by lysosomal enzymes from Dau conjugated to succinylated serum albumin without a peptide spacer.

Another tetrapeptide spacer was derived from a long collaboration between Duncan and Kopecek, in which the release of p-nitroaniline as a model drug from poly[N-(2-hydroxypropyl)methacrylamide] co-polymers was investigated (described in Duncan [(Duncan, (1986) *CRC Crit. Rev. Biocompat.* 2:127–145)]). These studies resulted in a greater understanding of lysosomal enzyme specificity and the development of a Gly-Phe-Leu-Gly-Dau linker which released 80% of bound p-nitroaniline over a 50-h incubation period. Daunomycin was subsequently coupled to the polymer delivery systems (Duncan, et al., (1987) *Br. J. Cancer* 55:165–174) and as antibody carrier drug conjugates.

A tetrapeptide spacer has been incorporated into monoclonal antibody-methotrexate conjugates by (Umemoto, et al., (1989) *Int. J. Cancer* 43:677–684). This is a MTX-Leu-Ala-Leu-Ala-hydrazide linker based on the tetrapeptide described by Trouet. However, in Trouet's study the Dau was attached to the C-terminal of the peptide, and in this conjugate MTX was attached to the N terminal of the peptide. In addition there is also a hydrazide incorporated into the linkage which may give some acid-sensitive release of the drug-linker part of the conjugate. No studies were reported on the effect of lysosomal enzymes on this linker, and what products were released, nor the rate of release of products. However, these linkers gave a substantial increase in efficiency of the conjugate compared to directly linked MTX, and release was shown by inhibitors such as leupeptin to be lysosomally mediated.

The development of a further tetrapeptide spacer for an HAS carrier molecule has been described by (Fitzpatrick, et al., (1995) *Anti-Cancer Drug Design* 10: 1–9). An appropriate spacer was developed using a lysosomal enzyme degradation system, where attachment of the terminal residue of the peptide chain to an ε-amino lysine residue was used as a model for conjugation to protein. Using this system it was shown that a variety of amino acids coupled to the carboxyl groups of MTX could release free drug, and the rate of release of free drug was dependent on the length of the spacer, a tetrapeptide spacer giving about 90% release of free drug. Conjugation of the MTX-tetrapeptide to HAS further reduced the rate of release of free drug to about 30% over 48 h. These experiments show that the tetrapeptide spacer is not just to overcome steric constraints of a polymer molecules, but also relate to the efficiency of binding of the cleavage site to the enzyme active site.

An efficient and general method for linking anthracyclines to peptides by an oxime linkage has been described by (Ingallinella, et al., (2001) *Bioorg. Med. Chem. Lett.* 11: 1343–1346; however, no immunoconjugates were reported using this linkage.

Generally the simplest way of producing an immunoconjugate is to couple the drug directly to the antibody. This may involve a direct linkage between the functional group of the drug, and one of the functional groups on the antibody, or alternatively may involve the interposition of a linker or spacer group between these two parts of the conjugate. A linker group may be used merely to make the chemistry of the coupling possible, but may have the second function of allowing a specific type of release of the drug. If the release is mediated by an enzyme, located either intra- or extracellularly, the group may be termed a spacer group, its purpose being to allow sufficient space, or reduce steric constraints so that the enzyme can access the relevant bond adequately.

Methotrexate was one of the first cytotoxic drugs to be linked to antibodies. In these early studies using immune sera (Marthé al., (1958) *C.R. Acad. Sci.* 246:1626–1628 and Burstein, et al., (1977) *J. Med. Chem.* 20:950–952) with coupling either through diazotization or mixed anhydride procedures. Both of these procedures resulted in therapeutically active conjugates in mouse models.

The conjugates that have been produced have been documented in many reviews (e.g., Magerstädt (1991) *CRC Press* Boca Raton, Fla. 77–215; Dubowchik, et al., (1999) *Pharmacol. Ther.* 83:67–123; and Pieterscz, et al., (1994) *Adv. Immunol.* 56:301–387). Early work with vinblastine-antibody conjugates used a variety of methods for conjugating drug to antibody, with some reports showing increased cytotoxicity of conjugate compared to free drug (Johnson, et al., (1981) *Br. J. Cancer* 44:372). Clinical studies on vinblastine conjugates have been reported. The first of these studies involved a conjugate with the murine monoclonal antibody KS1/4, using a hemisuccinate derivative of DAVLB rather then the optimized DAVLBHY (Schneck, et al., (1990) *Clin. Pharmacol. Exp.* 47:36–41).

The two main anthracyclines used in antibody conjugates are daunomycin (synonymous with daunorubicin) and adriamycin (synonymous with doxorubicin), differing in only the terminal C14 of the side chain, which is a methyl group in the former and a less hydrophobic methoxy group in the latter. Daunomycin (Dau) is reported to be more cytotoxic than doxorubicin (Dox). Idarubicin and epirubicin are slightly more cytotoxic derivatives, with an improved toxicity profile compared to Dau or Dox (Arcamone, (1985) *Cain Memorial Aware Lecture, Cancer Res.* 45:5995–5999). Morpholinodoxorubicin and cyanomorpholino doxorubicin were reported to be highly cytotoxic derivatives (Newman, et al., (1985) *Science* 228:1544–1546).

Immunoconjugate preparations of anthracyclines (Dau and Dox) to immunoglobulin assessed (Hurwitz, et al., (1975) *Cancer Res.* 35:1175–1181): (1) periodate oxidation of the sugar moiety of the drug, conjugation to the lysyl groups of antibody and subsequent reduction of the Schiff base reduction, (2) glutaraldehyde coupling between the sugar amino group and lysyl groups of antibody. Drug activity was best preserved with glutaraldehyde activity, but both periodate-oxidised and glutaraldehyde-linked conjugates showed good activity against target cells. The periodate-oxidised conjugates were assessed in more detail (Levy, et al., (1975) *Cancer Res.* 35:1182–1186) and shown to retain about 50% of the activity of free drug and have specificity in a cytotoxicity assay involving a brief exposure to immunoconjugate. The antitumour effects of the conjugate on PC5 B-cell leukemia were better than the free drug.

Idarubicin (Ida) immunoconjugates were prepared from 14-bromo-idarubicin with anti-ly2.1 antibodies with an MR of 1–5 (Pietersz, et al., (1988) *Cancer Res.* 48:926–931).

Conjugates showed selective cytotoxicity that was less active than free drug on E3 target cells ($IC_{50}$=430 and 120 nM, respectively). Anti-tumour activity was shown on E3 thymoma xenografts by reduction of tumour growth rate which was greater than that produced by Ida alone. Further studies using IDA immunoconjugates prepared from anti-CD19 antibody gave activities of 240 nM for immunoconjugate compared to 12 nM for free Ida (Rowland, et al., (1993) *Cancer Immunol. Immunother.* 37:195–202).

The anthracyclines have been a popular choice of drug for targeted delivery. The morpholino group makes the sugar amino group commonly used for conjugation unavailable so linkers via the C13 on the side chain were used.

Immunoconjugates with 5-fluoro-2'-deoxyuridine (FUDR) were constructed by reacting an active ester derivative of succinylated FUDR with anti-ly1.2 monoclonal antibody giving a conjugate with drug to antibody MR of 7–9 (Krauer, et al., (1992) *Cancer Res.* 52:132–137). On the antigen-positive E3 cell line succinylated FUDR, and immunoconjugate both gave similar cytotoxicities ($IC_{50}$=5 and 3 nM, respectively) which were about 10-fold lower than free drug (0.4 nM). In vivo a greater inhibition of E3 thymoma tumour growth was seen with the immunoconjugate than with an equivalent amount of free drug.

A taxol immunoconjugate has been reported by Guillemard and Saragovi (Guillemard, et al., (2001) *Cancer Res.* 61:694–699). Taxol was first modified with glutaric anhydride, to give a cleavable ester linkage to the drug, and then conjugated directly to antibody using carbodiimide. Immunoconjugate to anti-mouse and anti-rat IgG were made with an MR of drug to antibody of 1. Cytotoxicity tests appeared to show that conjugates were more cytotoxic than free drug. In vivo, immunoconjugate showed a small but significant reduction of tumour growth on neuroblastoma xenografts.

Antibody concentration is an important determinant of the rate of drug uptake; therefore, if more drug molecules can be conjugated per antibody molecule, cytotoxicity should increase. However, as the loss of antibody binding activity is the rate-limiting factor in the number of drug molecule, the use of carrier molecules for targeted drug conjugates offers a solution to this problem. A number of types of conjugate have been explored, mostly using dextran, human serum albumin or hydroxypropylmethacrylamide (HPMA) as the carrier molecules, and using the drugs doxorubicin or methotrexate. The earliest carrier conjugate was of phenylene diamine mustard to antibody via a polyglutamic acid carrier, showing a 45:1 molar substitution ratio (Rowland, et al., (1975) *Nature* 255:487–488).

Another solution to the difficulties of delivering sufficient drug molecules to kill cancer cells is to use more potent drugs, which require fewer molecules of drug to kill a cell. A number of these molecules have been discovered and investigated as potential anti-tumour agents. These include: CC-1065-like alkylating agents such as Duocarmycin;Enediynes, including the dynemicins, the calicheamicins/esperamicins, and the chromoproteins (Borders, et al., (1994) *Marcel Dekker* New York) (e.g., Neocarzinostatin, and Calicheamicin), and Macrolide antibiotics such as Geldanamycin and maytansine.

Application of tumor-targeted cytotoxic therapeutics has been used successfully with many tumor antigens. For example, Gemtuzumab ozogamicin, used to treat acute myelogenous leukemias (AMLs), is composed of an anti-CD33 antibody attached to calicheamicin, an antitumor chemotherapeutic agent. The CD33 antigen is present on myeloid precursors, but not on hematopoietic stem cells, so the CD33-targeted therapeutic is selective for AML cells while sparing critical normal cell types. Binding of this agent to the CD33 antigen present of AML cells results in the formation of a complex that is internalized into the cell. After internalization, the antitumor moiety of this agent is released into the myeloid cells and causes cell death (Naito et al. (2000) *Leukemia* 14: 14636–43). This drug has been approved by the FDA for treatment of relapsed or refractory AML in patients over 60 years old (Abou-Jawde et al. (2003) *Clin. Therap.* 25: 2121–37). Furthermore, gemtuzumab ozogamicin has shown benefit in treating recurrent AMS and, as such, may help many patients.

Immuntoxins

The therapeutic agent or drug moiety is not to be construed as limited to classical chemical or radiological therapeutic agents. For example, the drug moiety may be a protein or polypeptide possessing a desired biological activity. Such proteins may include, for example, in addition to toxins such as abrin, ricin A, pseudomonas exotoxin, or diphtheria toxin, other proteins with biological activity such as tumor necrosis factor, alpha-interferon, beta-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, IL-1, IL-2, IL-4, IL-5, IL-6, IL-7, IL-8, IL-9, IL-10, IL-12, IL-15, granulocyte macrophase colony stimulating factor ("GM-CSF"), granulocyte colony stimulating factor ("G-CSF"), or other growth factors.

Immunotoxins contain a ligand such as a growth factor, monoclonal antibody, or fragment of an antibody which is connected to a protein toxin. After the ligand subunit binds to the surface of the target cell, the molecule internalizes and the toxin kills the cell. Bacterial toxins which have been targeted to cancer cells include Pseudomonas exotoxin and diphtheria toxin, which are well suited to forming recombinant single-chain or double-chain fusion toxins. Plant toxins include ricin, abrin, pokeweed antiviral protein, saporin and gelonin, and have generally been connected to ligands by disulfide-bond chemistry. Immunotoxins have been produced to target hematologic malignancies and solid tumors via wide variety of growth factor receptors and antigens.

The goal of immunotoxin therapy is to target a cytotoxic agent to cell surface molecules which will internalize the cytotoxic agent and result in cell death. Since immunotoxins differ greatly from chemotherapy in their mode of action and toxicity profile, immunotoxins provide improved systemic treatment of tumors.

Immunotoxins can be simply defined as proteins containing a toxin and an antibody. Toxins reviewed here include catalytic proteins produced by plants or bacteria which kill target cells. While the term 'immunotoxin' generally refers to a toxin targeted by either an intact IgG, an Fab fragment or an Fv fragment, toxins targeted by growth factors or other ligands are also referred to as 'chimeric toxins'. In some immunotoxins or chimeric toxins, the linkage between the ligand and the toxin is made chemically, and the proteins may be referred to as 'chemical conjugates'. Otherwise, when the linkage is a peptide bond produced by genetic engineering, the proteins are referred to as 'recombinant toxins' or 'fusion toxins'. Finally, a select group of immunotoxins contain an Fv sequence fused to the toxin, and these proteins, being both immunotoxins and recombinant toxins, are often referred to as 'recombinant immunotoxins'.

Protein toxins are well suited because of their extreme potency. It has been shown that one or a few molecules of protein toxins can kill a cell when injected into the cytoplasm (see Yamaizumi, et al., (1978) *Cell* 15:245–250 and Eiklid, et al., (1980) *Exp. Cell Res.* 126:321–326).

Plant toxins exist in nature as holotoxins and hemitoxins. Holotoxins (also referred to as class II ribosome in activating proteins) include ricin, abrin, misdetoe lectin and modeccin, which contain a binding domain disulfide-bonded to an enzymatic domain. Hemitoxins, such as pokeweed antiviral protein (PAP), saporin and gelonin contain an enzymatic but no binding domain.

To make immunotoxins, plant toxins are generally conjugated chemically to ligands (see e.g., Kreitman, et al., (1998) *Adv. Drug Del. Rev.*, 31:53–88).

Two bacterial toxins generally used to make immunotoxins include *Pseudomonas* exotoxin (PE), made by *Pseudomonas aeruginosa*, and diphtheria toxin (DT), made by *Corynebacterium diphtherae*. Both PE and DT catalytically ADP ribosylate EF-2 in the cytosol (see Carroll et al., (1987) *J. Biol Chem.* 262:8707–8711; Uchida et al., (1972) *Science* 175:901–903; and Uchida et al., (1973) *J. Biol. Chem.* 248:3838–3844).

Mutated and truncated forms of DT and PE may also be used (see Kreitman, et al., (1998) *Adv. Drug Del. Rev.*, 31:53–88). For example, mutant toxins will be designed in which the binding domain of the toxin was deleted or made non-functional by mutation. In the case of DT this could be done chemically by treating the toxin with trypsin and purifying the A-chain (see Masuho, et al., (1979) *Biochem. Biophys. Res. Commun.* 90:320–326). Recombinant toxins which are full-length and contain mutated binding domains include $PE^{4E}$, containing glutamate replacing basic residues at positions 57, 246, 247 and 249 of PE, and CRM107, containing phenylalanines replacing a leucine at position 390 and serine at position 525 of DT (see Greenfield, et al., (1987) *Science* 238:536–539 and Chaudhary, et al., (1990) *J. Biol. Chem.* 265:16306–16310).

A wide variety of trace immunotoxins and recombinant toxins have been made and tested against malignant target cells (see Kreitman, et al., (1998) *Adv. Drug Del. Rev.*, 31:53–88).

The next generation of immunotoxin include recombinant toxins, immunotoxins containing an antibody or antibody fragment like an Fab' chemically conjugated to a toxin have several disadvantages. Firstly, their large size (100–200 kDa), often results in reduces tumor penetration. Secondly, for conjugation to antibodies, toxins such as PE40 and PE38 must be derivatized with reagents which modify the lysine residues, many of which are near the carboxyl terminus. Similarly, the antibody may require derivatization of lysine residues within the antigen binding domains. The resulting immunotoxins are therefore a heterogeneous mixture with respect to sites of attachment of the antibody and toxin, as well as the number of toxin and antibody components per immunotoxin molecule. Finally, chemical conjugates are difficult to produce, because the toxin and antibody must be purified separately, conjugated, and then the product repurified.

Toxins can be targeted to cells without chemically conjugating the ligand and the toxin if both are connected as one polypeptide unit.

The bacterial toxins PE and DT are optimal for making these fusion toxins because each toxin contains a proteolytic processing site within a disulfide loop which allows the catalytic domain to separate from the rest of the toxin after internalization and translocate efficiently to the cytosol (see Chiron, et al., 1994) *J. Biol. Chem.* 269:18167–18176); Fryling, et al., (1992) *Infect. Immun.* 60:497–502; Ogata, et al., (1992) *J. Biol. Chem.* 267:25396–25401; and Williams, et al., (1990) *J. Biol. Chem.* 265:20673–20677).

In 1981 it is reported that the Mab B3/25 was conjugated to truncated DT or RTA and used to inhibit the growth of human melanoma in nude mice (see Trowbridge, et al:, (1981) *Nature* 294:171–173). These and similar immunotoxins have displayed antitumor activity against a variety of solid tumors, including gastrointestinal adenocarcinomas, mesothelioma, cervical cancer and glioblastoma (see Griffin, et al., (1998) *J. Biol. Response Mod.* 7:559–567; Griffin, et al., (1987) *Cancer Res.* 47:4266–4270; and Martell, et al., (1993) *Cancer Res.* 53:1348–1353). The Mab HB21 was conjugated to full-length PE and delivered intraperitoneally to increase the survival of mice harboring human ovarian carcinoma (see FitzGerald., et al., (1986) *Proc. Natl. Acad. Sci. USA* 83:6627–6630). HB21 as well as its Fab', (Fab')$_2$ and Fv fragments have also been conjugated or fused to truncated PE or DT and shown to cause antitumor activity in a variety of models (see Batra, et al., (1989) *Proc. Natl. Acad. Sci. USA* 86:8545–8549; Debinski, et al., (1991) *Cancer Res.* 52:5379–5385; and Batra, et al., (1991) *Mol. Cell. Biol.* 11:2200–2205).

Many of the cell lines that are targets for immunotoxins targeting a variety of antigens are relatively resistant to chemotherapy. Immunotoxins have also been made to specifically target cells resistant to multiple chemotherapeutic agents by targeting the p-glycoprotein molecule which is responsible for increased export of chemotherapeutic agents from cells. The Mab MRK16 conjugated to PE was very cytotoxic toward those cell lines that were most resistant to chemotherapy due to expression of p-glycoprotein (see FitzGerald, et al., (1987) *Proc. Natl. Acad. Sci. USA* 84:4288–4292). This immunotoxin also killed multidrug-resistant carcinoma cells in MDR-transgenic mice (see Mickisch, et al., (1993) *J. Urol.* 149:174–178). This antibody has also been conjugated to saporin to form an immunotoxin able to purge multidrug resistant cells from bone marrow (see Dinota, et al., (1990) *Cancer Res.* 50:291–4294.

Targeted Radiotherapy

Radioisotopes may also be used as cytotoxic agents for HSC70-targeted therapeutics. Anti-HSC70 antibodies of the present invention may be coupled to one or more therapeutic agents. Suitable agents in this regard include radionuclides. Suitable radionuclides include $^{90}$Y, $^{123}$I, $^{125}$I, $^{131}$I, $^{186}$Re, $^{188}$Re, $^{211}$At, and $^{212}$Bi. Carriers specific for radionuclide agents, to facilitate attachment to the HSC70 targeting agent, include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

An ideal radioligand therapy agent would accumulate selectively in target cells. The effectiveness of radiotherapy is due to the destruction of dividing cells resulting from radiation-induced damage to cellular DNA (see, e.g., W. D. Bloomer et al., (1977) "Therapeutic Application of Iodine-125 Labeled Iododeoxyuridine in an Early Ascites Tumour Model," *Current Topics in Radiation Research Quarterly* 12:513–25). In both therapeutic and imaging applications, any unbound, circulating radioligand is rapidly cleared by excretory systems, which helps protect normal organs and tissues. The radioligand may also be degraded by body processes which will increase the clearance of the free radioisotope (see G. A. Wiseman et al. (1995) "Therapy of Neuroendocrine Tumors with Radiolabelled MIBG and Somatostatin Analogues," *Seminars in Nuclear Medicine*, vol. XXV, No. 3, pp. 272–278).

Radioisotopes most suitable for therapeutic treatment include Auger-electron-emitting radioisotopes, e.g. $^{125}$I, $^{123}$I, $^{124}$I, $^{129}$I, $^{131}$I, $^{111}$In, $^{77}$Br, and other radiolabeled halogens. The choice of a suitable radioisotope can be optimized based on a variety of factors including the type of radiation emitted, the emission energies, the distance over which energy is deposited, and the physical half-life of the radioisotope. In certain instances, the radioisotopes used are those having a radioactive half-life corresponding to, or longer than, the biological half-life of the HSC70-targeted therapeutic. For example, in certain examples the radioisotope has a half-life between about 1 hour and 60 days, preferably between 5 hours and 60 days, more preferably between 12 hours and 60 days. $^{125}$I has an advantage over other emitters that produce high-energy gamma rays (i.e., $^{111}$In and $^{131}$I) which require inpatient hospitalization and isolation $^{125}$I will allow the development of outpatient-based treatments due to the limited amounts of radiation that escapes the body.

Radiolabeled therapeutics have typically been administered by intravenous, bolus injection (see, e.g., H. P. Kalofonos et al., (1989) "Antibody Guided Diagnosis and Therapy of Brain Gliomas using Radiolabeled Monoclonal Antibodies Against Epidermal Growth Factor Receptor and Placental Alkaline Phosphatase" *The Journal of Nuclear Medicine* vol. 30, pp. 163–645; I. Virgolini et al., (1994) "Vasoactive Intestinal Peptide-Receptor Imaging for the Localization of Intestinal Adenocarcinomas and Endocrine Tumors" *The New England Journal of Medicine*, vol. 331, pp., 1116–21; G. A. Wiseman et al., (1995) "Therapy of Neuroendocrine Tumors with Radiolabelled MIBG and Somatostatin Analogues" *Seminars in Nuclear Medicine*, vol. XXV, no. 3, pp. 272–78; S. W. J. Lamberts et al., (1990) "Somatostatin-Receptor Imaging in the Localization of Endocrine Tumors" *The New England Journal of Medicine* vol. 323, pp. 126–49; E. P. Krenning et al. (1992) "Somatostatin Receptor Scintigraphy with Indium-111-DTPA-D-Phe-1-Octreotide in Man: Metabolism, Dosimetry and Comparison with Iodine-123-Tyr-3-Octreotide" *The Journal of Nuclear Medicine* vol. 33, pp. 652–58; E. P. Krenning et al.

(1989) "Localisation of Endocrine-Related Tumours with Radioiodinated Analogue of Somatostatin," *The Lancet* vol. 1989, no. 1, pp. 242–244.

Targeted Gene Therapy

Gene vectors may also be used as cytotoxic agents for HSC70-targeted therapeutics. For example, a gene vector encoding an antibody gene (or fragment thereof) inside the tumor cell. The transgene expression product binds intracellular proteins, e.g., those derived from oncogenes, and thereby down-regulates oncogenic protein expression. Targeted gene therapy may be facilitated by the use of bifunctional crosslinkers to target adenoviral and retroviral vectors, by inserting short targeting peptides and larger polypeptide-binding domains into the coat protein of a number of different viral vectors, and by by the use of replication-competent vectors (see Wand and Liu (2003) *Acta Biochimica et Biophysica Sinica* 35(4): 311–6). Other non-viral therapeutic agents, including DNA complexes and bacterial vehicles, have also been developed. Gene therapy methods for HSC70-targeted compositions and methods of the invention may be adapted from gene therapy methods known in the art or adapted from U.S. Pat. Nos. 5,871,726, 5,885,806, 5,888,767, 5,981,274, 6,207,426, 6,210,708, 6,232,120, 6,498,033, 6,537,805, 6,555,107, and 6,569,426.

In one approach, targeted replicative or non-replicative viral vectors may be used to deliver the gene therapeutic. For example, andoviral gene therapy vectors have been adapted for the targeting of neoplastic cells (see Rots, et al. (2003) *Journal of Controlled Release* 87: 159–165). Selective targeting of adenovirus vectors limits the inflammatory and immune response against the viral vector and decreases the toxicity of the treatment because lower doses of virus can be used. Adenoviral infection is normally initiated by the binding of target cells by the C-terminal part of the adenovirus fiber protein, termed know, and the primary cellular receptor, coxsackie B virus and adenovirus receptor (CAR). After this step, entry of the virus into the cell occurs via interaction of the RGD (arg-gly-asp) sequence of viral penton base protein and cellular integrins. Selective targeting of adenovirus vectors can be achieved. Linking (e.g., conjugation) of a HSC70-specific antibody to the adenoviral vector will target the resulting construct to HSC70-expressing neoplastic, MDR neoplastic and damaged (e.g. pathogen infected) cells. For example, this strategy has been successfully adapted to target adenovirus to the EGP-2 antigen present on tumor cells (Heiderman et al. (2001) *Cancer Gene Ther.* 8: 342–51) by conjugating an a neutralizing anti-fiber protein antibody to an antibody against the Epithelial Cell Adhesion Molecule (EGP-2). The resulting EGP-2 adenovirus was targeted to cancer cells expressing EGP-2, and infection was shown to be independent of CAR. Another strategy is to use bispecific antibodies to bridge cell surface HSC70 to the therapeutic gene delivery vector (e.g., adenoviral vector) (see, e.g., Haisma et al. (2000) *Cancer Gene* 7: 901–4; Grill et al. (2001) *Clin. Cancer Res.* 7: 641–50; Krasnykh et al. (1998) *J. Virol.* 72: 1844–52; and van Beusechem et al. (2000) *Gene Ther.* 7: 1940–46).

In general, the terms "viral vectors" and "viruses" are used interchangeably herein to refer to any of the obligate intracellular parasites having no protein-synthesizing or energy-generating mechanism. The viral genome may be RNA or DNA contained with a coated structure of protein of a lipid membrane. The terms virus(es) and viral vector(s) are used interchangeably herein. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. The viruses may be naturally occurring viruses or their viral genomes may be modified by recombinant DNA techniques to include expression of exogenous transgenes and may be engineered to be replication deficient, conditionally replicating or replication competent. Chimeric viral vectors which exploit advantageous elements of each of the parent vector properties (See e.g., Feng, et al. (1997) *Nature Biotechnology* 15:866–870) may also be useful in the practice of the present invention. Minimal vector systems in which the viral backbone contains only the sequences need for packaging of the viral vector and may optionally include a transgene expression cassette may also be produced according to the practice of the present invention. Although it is generally favored to employ a virus from the species to be treated, in some instances it may be advantageous to use vectors derived from different species that possess favorable pathogenic features. For example, equine herpes virus vectors for human gene therapy are described in WO98/27216 published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO97/06826 published Apr. 10, 1997.

The term "replication deficient" refers to vectors which are incapable of replication in a wild type mammalian cell. In order to produce such vectors in quantity, the producer cell line must be cotransfected with a helper virus or modified to complement the missing functions. For example, 293 cells have been engineered to complement adenoviral E1 deletions allowing propagation of the E1 deleted replication deficient adenoviral vectors in 293 cells. The term "replication competent viral vectors" refers to a viral vector which is capable of infection, DNA replication, packaging and lysis of an infected cell. The term "conditionally replicating viral vectors" is used herein to refer to replication competent vectors which are designed to achieve selective expression in particular cell types while avoiding untoward broad spectrum infection. Such conditional replication may be achieved by operably linking tissue specific, tumor specific or cell type specific or other selectively induced regulatory control sequences to early genes (e.g. the E1 gene of adenoviral vectors).

In addition to targeting, cell type specificity with viral vectors may be improved through the use of a pathway responsive promoters driving a repressor of viral replication. The term "pathway-responsive promoter" refers to DNA sequences that bind a certain protein and cause nearby genes to respond transcriptionally to the binding of the protein in normal cells. Such promoters may be generated by incorporating response elements which are sequences to which transcription factors bind. Such responses are generally inductive, though there are several cases where increasing protein levels decrease transcription. Pathway-responsive promoters may be naturally occurring or synthetic. Pathway-responsive promoters are typically constructed in reference to the pathway or a functional protein that is targeted. For example, a naturally occurring p53 pathway-responsive promoter would include transcriptional control elements activated by the presence of functional p53 such as the p21 or bax promoter. Alternatively, synthetic promoters containing p53 binding sites upstream of a minimal promoter (e.g. the SV40 TATA box region) may be employed to create a synthetic pathway-responsive promoter. Synthetic pathway-responsive promoters are generally constructed from one or more copies of a sequence that matches a consensus binding motif. Such consensus DNA binding motifs can readily be determined. Such consensus sequences are generally arranged as a direct or head-to-tail repeat separated by a few base pairs.

Examples of pathway-responsive promoters useful in the practice of the present invention include synthetic insulin pathway-responsive promoters containing the consensus insulin binding sequence (Jacob, et al. (1995) *J. Biol. Chem.* 270:27773–27779), the cytokine pathway-responsive promoter, the glucocorticoid pathway-responsive promoter (Lange, et al. (1992) *J Biol. Chem.* 267:15673–80), IL1 and IL6 pathway-responsive promoters (Won K.- A and Baumann H. (1990) *Mol. Cell. Biol.* 10: 3965–3978), T3 pathway-responsive promoters, thyroid hormone pathway-responsive promoters containing the consensus motif, the TPA pathway-responsive promoters (TREs), TGF-beta pathway-responsive promoters (as described in Grotendorst, et al. (1996) *Cell Growth and Differentiation* 7: 469–480). Additionally, natural or synthetic E2F pathway responsive promoters may be used. An example of an E2F pathway responsive promoter is described in Parr, et al. (1997) *Nature Medicine* 3:1145–1149) which describes an E2F-1 promoter containing 4 E2F binding sites and is reportedly active in tumor cells with rapid cycling. Examples of other pathway-responsive promoters are well known in the art and can be identified in the Database of Transcription Regulatory Regions on Eukaryotic Genomes accessible through the internet at world wide web eimb.rssi.ru/TRRD.

In the certain applications of the invention, the viral vector is an adenovirus. The term "adenovirus" is synonomous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F sugenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11 P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1,2,3,4,7, and 10. The term canine adenoviruses includes but is not limited to canine types 1 (strains CLL, Glaxo, RI261, Utrect, Toronto 26–61) and 2. The term equine adenoviruses includes but is not limited to equine types 1 and 2. The term porcine adenoviruses includes but is not limited to porcine types 3 and 4. The term viral vector includes replication deficient, replication competent and conditionally replicating viral vectors.

Particularly useful are vectors derived from human adenovirus types 2 and 5. These vectors may incorporate particular modifications to enhance their therapeutic potential. For example they may include deletions of E1a and E1b genes. Certain other regions may be enhanced or deleted to provide specific features. For example upregulation of the E3 region is described to reduce the immunogenicity associated with human adenoviral vectors administered to human subjects. The E4 region has been implicated as important to expression of transgenes from the CMV promoter, however the E4orf 6 protein has been described as leading to the degradation of p53 in target cells in the presence of E1b large protein (Steegenga, et al. (1998) *Oncogene* 16:345–347).

The therapeutic gene to be delivered is generally a cytotoxic gene, a tumor suppressor gene, a toxin gene, a pro-apoptotic gene, a pro-drug activating gene, or a cytokine gene. The term "cytotoxic transgene" refers to a nucleotide sequence the expression of which in the target cell induces lysis or apoptosis of the cell. The term cytotoxic transgene includes but is not limited to tumor suppressor genes, toxin genes, cytostatic genes, pro-drug activating genes, or apoptotic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) *Nature* 329:642), the MMAC-1 gene, the adenomatous polyposis coli protein (U.S. Pat. No. 5,783,666), the deleted in colon carcinoma (DCC) gene, the MMSC-2 gene, the NF-1 gene, nasopharyngeal carcinoma tumor suppressor gene that maps at chromosome 3p21.3. (Cheng, et al. (1998) *Proc. Nat. Acad. Sci.* 95:3042–3047), the MTS1 gene, the CDK4 gene, the NF-1 gene, the NF2 gene, and the VHL gene.

The term "toxin gene" refers to nucleotide sequence, the expression of which in a cell produces a toxic effect. Examples of such toxin genes include nucleotide sequences encoding pseudomonas exotoxin, ricin toxin, diptheria toxin, and the like.

The term "pro-apoptotic gene" refers to a nucleotide sequence, the expression thereof results in the programmed cell death of the cell. Examples of pro-apoptotic genes include p53, adenovirus E3-11.6K, the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5-fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see U.S. Pat. No. 5,631,236 and U.S. Pat. No. 5,601,818) in which the cells expressing the TK gene product are susceptible to selective killing by the administration of gancyclovir may be employed.

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the alpha, beta and gamma subtypes especially interferon alpha-2b and fusions such as interferon alpha-2-alpha-1.

Modifications and/or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the delta13–19 amino acids to eliminate the calpain consensus cleavage site, modifications to the oligomerization domains (as described in Bracco, et al. PCT published application WO97/0492 or U.S. Pat. No. 5,573,925).

The invention further includes use of gene-targeted non-viral vectors. "Non-viral vector" for use in this aspect of the invention include autonomously replicating, extrachromosomal circular DNA molecules, distinct from the normal genome and nonessential for cell survival under non-selective conditions capable of effecting the expression of a DNA sequence in the target cell. Plasmids autonomously replicate in bacteria to facilitate bacterial production. Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

In order to target the therapeutic gene to neoplastic, MDR neoplastic and damaged (e.g., pathogen-infected) cells, it is advantageous, in certain instances, to incorporate additional elements into non-viral gene delivery systems which facilitate cellular targeting. For example, a lipid encapsulated expression plasmid may incorporate HSC70 antibodies or ligands to facilitate targeting. Although a simple liposome formulation may be administered, the liposomes either filled or decorated with a desired composition of the invention of the invention can delivered systemically, or can be directed to a tissue of interest, where the liposomes then deliver the selected therapeutic/immunogenic peptide compositions. HSC70 antibodies and ligand for use in this application include antibodies, monoclonal antibodies, humanized antibodies, single chain antibodies, chimeric antibodies or functional fragments (Fv, Fab, Fab') thereof. Alternatively, non-viral vectors can be linked through a polylysine moiety to a targeting moiety as described in Wu, et al. U.S. Pat. No. 5,166,320 and U.S. Pat. No. 5,635,383.

Liposomal Formulations

Another strategy that may be employed for HSC70-targeted delivery of therapeutic agents is the use of immunoliposomes. Immunoliposomes incorporate antibodies against tumor-associated antigens into liposomes, which carry the therapeutic agent or an enzyme that activates an otherwise inactive prodrug (see, e.g., Lasic et al. (1995) *Science* 267: 1275–76). A number of pre-clinical reports have reported successful targeting and enhanced anti-cancer efficacy with immunoliposomal drugs (Maruyama et al. (1990) *J. Pharm. Sci.* 74: 978–84); Maruyama et al. (1995) *Biochim. Biophys. Acta* 1234: 74–80; Otsubo et al. (1998) *Antimicrob. Agents Chemother.* 42: 40–44; Lopes de Menezes et al. (1998) *Cancer Res.* 58: 3320–30).

Alternatively, non-antibody HSC70 binding agents such as modified LDL may be used as tumor-specific ligands in targeting liposoomal formulations of therapeutics. For example, folate-coupled liposomes can be used to target therapeutics to tumors which overexpress the folate receptor. Folate-coupled liposomes have been successfully delivered to folate receptor-overexpressing cancer cells in vitro as well as in vivo (Lee and Low (1994) *J. Biol. Chem.* 269: 3198–204; Lee and Low (1995) *Biochim. Biophys. Acta* 1233: 134–44; Rui et al. (1998) *J. Am. Chem. Soc.* 120: 11213–18; and Gabizon et al. (1999) *Bioconj. Chem.* 10: 289–98). Indeed, several pre-clinical reports have described the successful targeting of liposomal drugs coupled to such ligands (Ichinose et al. (1998) *Anticancer Res.* 18: 401–4; Yamamoto et al. (2000) *Oncol. Rep.* 7: 107–11; Rui et al. (1998) *J. Am. Chem. Soc.* 120: 11213–18; and Gabizon et al. (1999) *Bioconj. Chem.* 10: 289–98). Transferrin has been employed as a targeting lignad to direct liposomal drugs to various types of cancer cell in vivo (Ishida and Maruyama (1998) *Nippon Rinsho* 56: 657–62; Kirpotin et al. (1997) *Biochem.* 36: 66–75). PEG-immunoliposomes with anti-transferrin antibodies coupled to the distal ends of the PEG preferentially associate with C6 glima cells in vitro and significantly increased gliomal doxorubicin uptake after treatment with the tumor-specific long-circulating liposomes containing doxorubicin (Eavarone et al. (2000) *J. Biomed. Mater. Res.* 51: 10–14).

Methods of forming liposomal micelle/drug formulations are known in the art. For example, therapeutic drug micelles can be formed by combining a therapeutic drug and a phosphatidyl glycerol lipid derivative (PGL derivative). Briefly, the therapeutic drug and PGL derivative are mixed in a range of 1:1 to 1:2.1 to form a therapeutic drug mixture. Alternatively, the range of therapeutic drug to PGL derivative is in the ranges 1:1.2; or 1:1.4; or 1:1.5; or 1:1.6; or 1:1.8 or 1:1.9 or 1:2.0 or 1:2.1. The mixture is then combined with an effective amount of at least a 20% organic solvent such as an ethanol solution to form micelles containing the therapeutic drug. Methods for inclusion of an antibody or tumor targeting ligand into the micelle formulation to produce immunoliposomes are known in the art and described further below. For example, methods for preparation and use of immunoliposomes are described in U.S. Pat. Nos. 4,957,735, 5,248,590, 5,464,630, 5,527,528, 5,620,689, 5,618,916, 5,977,861, 6,004,534, 6,027,726, 6,056,973, 6,060,082, 6,316,024, 6,379,699, 6,387,397, 6,511,676 and 6,593,308.

As used herein, the term "phosphatidyl glycerol lipid derivative (PGL derivative)" is any lipid derivative having the ability to form micelles and have a net negatively charged head group. This includes but is not limited to dipalmitoyl phosphatidyl glycerol (DPPG), dimyristoyl phosphatidyl glycerol, and dicapryl phosphatidyl glycerol. In one aspect, phosphatidyl derivatives with a carbon chain of 10 to 28 carbons and having unsaturated side aliphatic side chain are within the scope of this invention. The complexing of a therapeutic drug with negatively-charged phosphatidyl glycerol lipids having variations in the molar ratio giving the particles a net positive (1:1) neutral (1:2) or slightly negative (1:2.1) charge will allow targeting of different tissues in the body after administration. However, complexing of a therapeutic drug with negatively charged PGL has been shown to enhance the solubility of the therapeutic drug in many instances, thus reducing the volume of the drug required for effective antineoplastic therapy. In addition, the complexing of a therapeutic drug and negatively charged PGL proceeds to very high encapsulation efficiency, thereby minimizing drug loss during the manufacturing process. These complexes are stable, do not form precipitates and retain therapeutic efficacy after storage at 4° C. for at least 4 months. In order to achieve maximum therapeutic efficacy by avoiding rapid clearance from the blood circulation by the reticuloendothelial system (RES), immunoliposomal drug formulations may incorporate components such as polyethylene glycol (PEG) (see Klibanov et al. (1990) *FEBS Lett.* 268: 235–7; Mayuryama et al. (1992) *Biochim. Biophys. Acta* 1128: 44–49; Allen et al. (1991) *Biochim. Biophys. Acta* 1066: 29–36). PEG conjugation to immunoliposomes has been shown to prolong liposome circulation in blood, as well as to enhance the therapeutic efficacy of liposomal drugs (Daemen et al. (1997) *J. Control Rel.* 44: 1–9; Storm et al. (1998) *Clin. Cancer Res.* 4: 111–115; Vaage et al. (1997) *Br. J. Cancer* 75: 482–6; Gabizon et al. (1994) *Cancer Res.* 54: 987–92). Long-circulating immunoliposomes can be classified into two types: those with antibodies coupled to a lipid head growth (Maruyama et al. (1990) *J. Pharm. Sci.* 74: 978–84); and those with antibodies coupled to the distal end of PEG (Maruyama et al. (1997) *Adv. Drug Del. Rev.* 24: 235–42). In certain instances, it way be advantageous to place the tumor-specific antibodies at the distal end of the PEG polymer to obtain efficient target binding by avoiding steric hindrance from the PEG chains. This type of immunoliposome formulation has been used successfully for in vivo targeting to the lungs (Maruyama et al. (1995) *Biochim. Biophys. Acta* 1234: 74–80; brain (Huwyler et al. (1996) *Proc. Natl. Acad. Sci. USA* 93: 14164–69); and tumors (Allen et al. (1995) *Biochem. Soc. Transact.* 23: 1073–79).

Effective delivery of drugs by immunoliposome formulations is generally enhanced by active uptake of the bound immunoliposome through endocytosis. Human scFv antibodies can be selected for optimized internalization into tumor cells from a phage display library to ensure optimal targeting and delivery of the immunoliposomes into which they are incorporated (see Poul et al. (2000) *J. Mol. Biol.* 301: 1149–61; Schier et al. (1996) *J. Mol. Biol.* 263: 551–67).

Another strategy related to antibody-mediated tumor targeting is antibody-directed enzyme pro-drug (ADEPT), which is a two step therapeutic approach designed to generate a high concentration of anticancer drugs in proximity to tumor cell membranes (Springer et al. (1996) *Adv. Drug Deliv. Rev.* 22: 351–64). Using this strategy, an enzyme-antibody conjugate that preferentially binds to a given tumor-associated antigen is administered first, followed by injection of a nontoxic prod-drug, which becomes activated by the action of the targeted enzyme. An improved ADEPT using immunoliposomes as a targeted carrier for the pro-drug-activating enzymes instead of an enzyme-antibody conjugate has been developed and tested (Storm et al. (1997) *Adv. Deliv. Rev.* 24: 225–31; Vingerhoeds et al. (1993) *FEBS Lett.* 336: 485–90).

Therapies

The invention provides for treatment or prevention of cancer, including, but not limited to, neoplasms, tumors, metastases, or any disease or disorder characterized by uncontrolled cell growth, and particularly multidrug resistant forms thereof by the administration of therapeutically or prophylactically effective amounts of anti-HSC70 antibodies or nucleic acid molecules encoding said antibodies. Examples of types of cancer and proliferative disorders to be treated with the HSC70-targeted therapeutics of the invention include, but are not limited to, leukemia (e.g., myeloblastic, promyelocytic, myelomonocytic, monocytic, erythroleukemia, chronic myelocytic (granulocytic) leukemia, and chronic lymphocytic leukemia), lymphoma (e.g., Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. In a particular embodiment, therapeutic compounds of the invention are administered to men with prostate cancer (e.g., prostatitis, benign prostatic hypertrophy, benign prostatic hyperplasia (BPH), prostatic paraganglioma, prostate adenocarcinoma, prostatic intraepithelial neoplasia, prostato-rectal fistulas, and a typical prostatic stromal lesions). The treatment and/or prevention of cancer includes, but is not limited to, alleviating symptoms associated with cancer, the inhibition of the progression of cancer, the promotion of the regression of cancer, and the promotion of the immune response. In one embodiment, commercially available or naturally occurring anti-HSC70 antibodies, functionally active fragments or derivatives thereof are used in the present invention.

The HSC70 therabpeutics may be administered alone or in combination with other types of cancer treatments (e.g., radiation therapy, chemotherapy, hormonal therapy, immunotherapy and anti-tumor agents). Examples of anti-tumor agents include, but are not limited to, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. In one embodiment, one or more anti-HSC70 antibodies are administered to an animal, preferably a mammal and most preferably a human, after surgical resection of cancer. In another embodiment, one or more anti-HSC70 antibodies are administered to an animal, preferably a mammal and most preferably a human, in conjugation with chemotherapy or radiotherapy. In another embodiment, one or more anti-HSC70 antibodies are administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of plasma to the animal.

The anti-HSC70 antibodies, and other HSC70-targeted therapeutics described herein, may be administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, one or more anti-HSC70 antibodies are administered to an animal, preferably a mammal and most preferably a human, prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more cancer cell antigens. In yet another preferred embodiment, one or more anti-HSC70 antibodies are administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies currently used for the treatment of cancer. Examples of such antibodies include, but are not limited to, Herceptin, Retuxan, OvaRex, Panorex, BEC2, IMC-C225, Vitaxin, Campath I/H, Smart M195, Lympho-Cide, Smart I D10, and Oncolym.

The invention further provides methods for the treatment or prevention of viral and other pathogen infections in an animal, preferably a mammal and most preferably a human, said methods comprising the administration of a therapeutically or prophylactically effective amount of anti-HSC70 antibodies or nucleic acid molecules encoding said antibodies or other HSC70-targeted therapeutics described herein. Examples of viral infections which can be treated or prevented in accordance with this invention include, but are limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus). The treatment and/or prevention of a viral infection includes, but is not limited to, alleviating symptoms associated with said infection, the inhibition or suppression of viral replication, and the enhancement of the immune response.

The HSC70-targeted therapeutics described herein may be administered alone or in combination with other types of anti-viral or other anti-pathogen agents. Examples of anti-viral agents include, but are not limited to: cytokines (e.g., IFN-.alpha., IFN-.beta., and IFN-.gamma.); inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides); inhibitors of viral mRNA capping, such as ribavirin; inhibitors of proteases such HIV protease inhibitors (e.g., amprenavir, indinavir, nelfinavir, ritonavir, and saquinavir,); amphotericin B; castanospermine as an inhibitor of glycoprotein processing; inhibitors of neuraminidase such as influenza virus neuraminidase inhibitors (e.g., zanamivir and oseltamivir); topoisomerase I inhibitors (e.g., camptothecins and analogs thereof); amantadine and rimantadine. For example, one or more anti-HSC70 antibodies-drug conjugates are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of plasma to the animal.

In other examples, one or more HSC70-targeted therapeutics are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, anti-HSC70 antibodies are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more viral antigens. Example of antibodies immunospecific for viral antigens include, but are not limited to, Synagis.RTM., PRO542, Ostavir, and Protovir.

The invention further provides methods for the treatment or prevention of microbial infections in an animal, preferably a mammal and most preferably a human, said methods comprising the administration of a therapeutically or prophylactically effective amount of anti-HSC70-targeted therapeutics. Examples of microbial infections which can be treated or prevented in accordance with this invention include, but are not limited to, yeast infections, fungal infections, protozoan infections and bacterial infections. Bacteria which cause microbial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori*. The treatment and/or prevention of a microbial infection includes, but is not limited to, alleviating symptoms associated with said infection, the inhibition or suppression of replication, and the enhancement of the immune response.

HSC70-targeted therapeutics may be administered alone or in combination with other types of anti-microbial agents. Examples of anti-microbial agents include, but are not limited to: antibiotics such as penicillin, amoxicillin, ampicillin, carbenicillin, ticarcillin, piperacillin, cepalospolin, vancomycin, tetracycline, erythromycin, amphotericin B, nystatin, metroidazole, ketoconazole, and pentamidine. In one embodiment, a HSC70-targeted therapeutic is administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after) or concomitantly with the administration of plasma to the animal.

In certain instances, one or more HSC70-targeted therapeutics are administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In other instances, one or more HSC70-targeted therapeutics are administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more microbial antigens. Example of antibodies immunospecific for microbial antigens include, but are not limited to, antibodies immunospecific for LPS and capsular polysaccharide 5/8. In certain embodiments, animals with increased risk of a viral or bacterial infection are administered a composition of the invention. Examples of such animals include, but are not limited to, human burn patients, infants, immunocompromised or immunodeficient humans, and the elderly.

4.6 Kits

The invention further provides kits for use in diagnostics or prognostic, as well as therapeutic, methods for neoplasias and multidrug resistant neoplasias. The diagnostic kits are useful, for example, for detecting cell surface HSC70-expressing neoplasias and for monitoring the occurrence of multidrug resistant cells in a patient sample or in situ in a patient. For example, during the course of patient chemotherapeutic treatment, monitoring of cell surface HSC70, and other MDR-associated markers described herein, provides valuable information regarding the efficacy of the treatment and for avoiding the development of multidrug resistance. For example, the kit can comprise a labeled compound or agent capable of detecting cell surface HSC70 protein in a biological sample; as well as means for determining the amount of cell surface HSC70 in the sample; and means for comparing the amount of HSC70 in the sample with a standard (e.g., normal non-neoplastic cells or non-MDR neoplastic cells). The compound or agent can be packaged in a suitable container. The kit can further comprise instructions for using the kit to detect cell surface HSC70 protein, as well as other MDR-associated markers. Such a kit can comprise, e.g., one or more antibodies capable of binding specifically to at least a portion of a cell surface HSC70 protein.

4.7 HSC70 Vaccines

Immunological compositions, including vaccines, and other pharmaceutical compositions containing the HSC70 protein, or portions thereof, are included within the scope of the present invention. One or more of the HSC70 proteins, or active or antigenic fragments thereof, or fusion proteins thereof can be formulated and packaged, alone or in combination with other antigens, using methods and materials known to those skilled in the art for vaccines. The immunological response may be used therapeutically or prophylactically and may provide antibody immunity or cellular immunity, such as that produced by T lymphocytes.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular mass of at least 1,000 Daltons, preferably greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The HSC70 protein or portions thereof, such as consensus or variable sequence amino acid motifs, or combination of proteins may be administered with an adjuvant in an amount effective to enhance the immunogenic response against the conjugate. One adjuvant widely used in humans has been alum (aluminum phosphate or aluminum hydroxide). Saponin and its purified component Quil A, Freund's complete adjuvant and other adjuvants used in research and veterinary applications are also available. Chemically defined preparations such as muramyl dipeptide, monophosphoryl lipid A, phospholipid conjugates such as those described by Goodman-Snitkoff et al. (1991) *J. Immunol.* 147:410–415 and incorporated by reference herein, encapsulation of the conjugate within a proteoliposome as described by Miller et al. (1992) *J. Exp. Med.* 176:1739–1744 and incorporated by reference herein, and encapsulation of the protein in lipid vesicles such as Novasome™ lipid vesicles (Micro Vascular Systems, Inc., Nashua, N.H.) may also be useful.

The invention includes the HSC70 polypeptide fragments, or subsequences of the intact HSC70 polypeptide shown in FIG. 12A (SEQ ID NO. 1). Such HSC70 polypeptide subsequences, or a corresponding nucleic acid sequence that encodes them in the case of DNA vaccines, are preferably selected so as to be highly immunogenic. The principles of antigenicity for the purpose of producing anti-HSC70 vaccines apply also to the use of HSC70 polypeptide sequences for use as immunogens for generating anti-HSC70 polyclonal and monoclonal antibodies for use in the HSC70-based diagnostics and therapeutics described herein.

Computer assisted algorithms for predicting polypeptide subsequence antigenicity are widely available. For example "Antigenic" looks for potential antigenic regions using the method of Kolaskar (see Kolaskar and Tongaonkar (1990) *FEBS Letters* 276:172–174 "A semi-empirical method for prediction of antigenic determinants on protein antigens"). In their initial study, Kolaskar and Tongaonkar experimentally tested 169 antigenic. The 156 which have less than 20 amino acids per determinant were selected (total 2066 residues). f(Ag) was calculated as the frequency of occurrence of each residue in antigenic determinants [f(Ag)= Epitope_occurrence/2066]. The Hydrophilicity, Accessibility and Flexibility values are from Parker, et al. (see Parker, et al. (1986) *Biochemistry* 25:5425–5432). In a given protein, the average for each 7-mer is calculated, and values are assigned to the central residue of the 7-mer. A residue is considered to be on the surface if any of the 7-mer values was above the average for the protein. These results were used to obtain f(s) as the frequency of occurrence of amino acids at the surface. The prediction algorithm includes the following steps: calculate the average propensity for each overlapping 7-mer and assign the result to the central residue (i+3) of the 7-mer; calculate the average for the whole protein; if the average for the whole protein is above 1.0 then all residues having above 1.0 are potentially antigenic; if the average for the whole protein is below 1.0 then all residues having above the average for the whole protein (note: the original paper has a mangled formula here) are potentially antigenic; find 6-mers where all residues are selected by step 3.

Another method for determining antigenicity of a polypeptide subsequence is the algorithm of Hopp and Woods ((1981) *Proc. Natl. Acad. Sci.* 86: 152–6). There are publicly available web sites for Hopp and Woods algorithm analysis of a user-input polypeptide sequence and convenient graphical output of the resulting analysis (see, e.g., hypertext transfer protocol hometown.aol.com/_ht_a/lucatoldo/myhomepage/JaMBW/3/1/7). Using this algorithm to analyze the full-length human HSC70 sequence shown in FIG. 14A, several suitable sequence having a high Hopp and Woods antigenic index of an adequate length for immunogenicity were revealed. These include HSC70 amino acid residues: 240–260 (i.e. HFIAEFKRKHKKDIS-ENKRAY); and 480–500 (i.e., IDANGILNVSAVDKST-GKENK).

In addition, the present invention provides a composition comprising the HSC70 protein or polypeptide fragment of the invention in combination with a suitable adjuvant. Such a composition can be in a pharmaceutically acceptable carrier, as described herein. As used herein, "adjuvant" or "suitable adjuvant" describes a substance capable of being combined with the HSC70 protein or polypeptide to enhance an immune response in a subject without deleterious effect on the subject. A suitable adjuvant can be, but is not limited to, for example, an immunostimulatory cytokine, SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion. The adjuvant, such as an immunostimulatory cytokine can be administered before the administration of the HSC70 protein or HSC70-encoding nucleic acid, concurrent with the administration of the HSC70 protein or HSC70-encoding nucleic acid or up to five days after the administration of the HSC70 protein or HSC70-encoding nucleic acid to a subject. QS-21, similarly to alum, complete Freund's adjuvant, SAF, etc., can be administered within hours of administration of the fusion protein.

The invention may also utilize combinations of adjuvants, such as immunostimulatory cytokines co-administered to the subject before, after or concurrent with the administration of the HSC70 protein or HSC70-encoding nucleic acid. For example, combinations of adjuvants, such as immunostimulatory cytokines, can consist of two or more of immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants may be determined by measuring the immune response directed against the HSC70 polypeptide with and without the adjuvant or combination of adjuvants, using standard procedures, as described herein.

Furthermore, the present invention provides a composition comprising the HSC70 protein or HSC70-encoding nucleic acid and an adjuvant, such as an immunostimulatory cytokine or a nucleic acid encoding an adjuvant, such as an immunostimulatory cytokine. Such a composition can be in a pharmaceutically acceptable carrier, as described herein. The immunostimulatory cytokine used in this invention can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 con-stimulatory molecules and B7.2 co-stimulatory molecules.

The term "vaccine" as used herein includes DNA vaccines in which the nucleic acid molecule encoding HSC70 or antigenic portions thereof, such as any consensus or variable sequence amino acid motif, in a pharmaceutical composition is administered to a patient. For genetic immunization, suitable delivery methods known to those skilled in the art include direct injection of plasmid DNA into muscles (Wolff et al. (1992) *Hum. Mol. Genet.* 1:363,), delivery of DNA complexed with specific protein carriers (Wu et al. (1989) *J. Biol. Chem.* 264:16985, coprecipitation of DNA with calcium phosphate (Benvenisty and Reshef (1986) *Proc. Natl. Acad. Sci.* 83:9551), encapsulation of DNA in liposomes (Kaneda et al. (1989) *Science* 243:375,), particle bombardment (Tang et al., (1992) *Nature* 356:152, and Eisenbraun et al. (1993) *DNA Cell Biol.* 12:791), and in vivo infection using cloned retroviral vectors (Seeger et al. (1984) *Proc. Natl. Acad. Sci.* 81:5849).

In another embodiment, the invention is a polynucleotide which comprises contiguous nucleic acid sequences capable of being expressed to produce a HSC70 or immunostimulant gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an immunogenic epitope, and optionally a cytokine or a T-cell costimulatory element, such as a member of the B7 family of proteins.

Advantages to immunization with a gene rather than its gene product include the following. First, is the relative simplicity with which native or nearly native antigen can be presented to the immune system. Mammalian proteins expressed recombinantly in bacteria, yeast, or even mammalian cells often require extensive treatment to ensure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a CD8+ response to NP that protected mice against challenge with heterologous strains of flu. (Montgomery, D. L. et al. (1997) *Cell Mol Biol* 43(3):285–92; and Ulmer, J. et al. (1997) *Vaccine* 15(8): 792–794). Cell-mediated immunity is important in controlling infection. Since DNA immunization can evoke both humoral and cell-mediated immune responses, its greatest advantage may be that it provides a relatively simple method to survey a large number of HSC70 genes and gene fragments for their vaccine potential.

The invention also includes known methods of preparing and using tumor antigen vaccines for use in treating or preventing cancers. For example, U.S. Pat. No. 6,562,347 which teaches the use of a fusion polypeptide including a chemokine and a tumor antigen which is administered as either a protein or nucleic acid vaccine to elicit an immune response effective in treating or preventing cancer. Chemokines are a group of usually small secreted proteins (7–15 kDa) induced by inflammatory stimuli and are involved in orchestrating the selective migration, diapedesis and activation of blood-born leukocytes that mediate the inflammatory response (see Wallack (1993) *Annals New York Academy of Sciences* 178). Chemokines mediate their function through interaction with specific cell surface receptor proteins (23). At least four chemokine subfamilies have been identified as defined by a cysteine signature motif, termed CC, CXC, C and $CX_3C$, where C is a cysteine and X is any amino acid residue. Structural studies have revealed that at least both CXC and CC chemokines share very similar tertiary structure (monomer), but different quaternary structure (dimer). For the most part, conformational differences are localized to sections of loop or the N-terminus. In the instant invention, for example, a human HSC70 polypeptide sequence (such as that shown in FIG. 12A), or polypeptide fragment thereof, and a chemokine sequence are fused together and used in an immunizing vaccine. The chemokine portion of the fusion can be a human monocyte chemotactic protein-3, a human macrophage-derived chemokine or a human SDF-1 chemokine. The HSC70 portion of the fusion is, preferably, a portion shown in routine screening to have a strong antigenic potential.

4.8 Pharmaceutical Formulations and Methods of Treatment

The present invention provides for both prophylactic and therapeutic methods of treating a subject having a neoplastic disease. Subjects at risk for such a disease can be identified by a diagnostic or prognostic assay, e.g., as described herein. Administration of a prophylactic agent can occur prior to the manifestation of symptoms characteristic of the neoplasm, such that development of the neoplasm is prevented or, alternatively, delayed in its progression. In general, the prophylactic or therapeutic methods comprise administering to the subject an effective amount of a compound which comprises a HSC70 targeting component that is capable of binding to cell surface HSC70 present on neoplastic, and particularly multidrug resistant neoplastic, cells and which compound is linked to a therapeutic component.

Examples of HSC70 targeting components include monoclonal anti-HSC70 antibodies and fragments thereof. Examples of suitable therapeutic components include traditional chemotherapeutic agents such as Actinomycin, Adriamycin, Altretamine, Asparaginase, Bleomycin, Busulfan, Capecitabine, Carboplatin, Carmustine, Chlorambucil, Cisplatin, Cladribine, Cyclophosphamide, Cytarabine, Dacarbazine, Dactinomycin, Daunorubicin, Docetaxel, Doxorubicin, Epoetin, Etoposide, Fludarabine, Fluorouracil, Gemcitabine, Hydroxyurea, Idarubicin, Ifosfamide, Imatinib, Irinotecan, Lomustine, Mechlorethamine, Melphalan, Mercaptopurine, Methotrexate, Mitomycin, Mitotane, Mitoxantrone, Paclitaxel, Pentostatin, Procarbazine, Taxol, Teniposide, Topotecan, Vinblastine, Vincristine, and Vinorelbine. Other examples of suitable therapeutic components include immunotoxins such as Pseudomonas exotoxin, a diphtheria toxin, a plant ricin toxin, a plant abrin toxin, a plant saporin toxin, a plant gelonin toxin, and pokeweed antiviral protein. Such immunotoxins are targeted to the HSC70 expressing neoplastic, or multidrug resistant neoplastic, cell by the HSC70 targeting component of the therapeutic compound and, upon binding of cell surface HSC70 and uptake into the cell, function to kill or block the growth of the neoplastic cell.

4.8.1 Effective Dose

Toxicity and therapeutic efficacy of such compounds can be determined by standard pharmaceutical procedures in cell cultures or experimental animals, e.g., for determining the $LD_{50}$ (The Dose Lethal To 50% Of The Population) And The $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.8.2 Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insulation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remrnington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a therapeutic and gene delivery system for the HSC70-targeted therapeutic can be introduced into a patient by any of a number of methods, each of which is familiar in the art. For instance, a pharmaceutical preparation of the HSC70-targeted therapeutic can be introduced systemically, e.g., by intravenous injection.

The pharmaceutical preparation of the HSC70-targeted therapeutic compound of the invention can consist essentially of the compound in an acceptable diluent, or can comprise a slow release matrix in which the gene delivery vehicle or compound is imbedded.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5. EXAMPLES

This invention is further illustrated by the following examples, which should not be construed as limiting. The contents of all references, patents and published patent applications cited throughout this application are hereby incorporated by reference. Nucleotide and amino acid sequences deposited in public databases as referred to herein are also hereby incorporated by reference. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

5.1 Overexpression of a 71 kDa Protein in Membranes of Multidrug Resistant Cancer Cells Studies were performed to determine what proteins, if any, were differentially expressed in multidrug resistant tumor cell lines as compared to their drug-sensitive counterparts.

A. Cells

The seven different cell lines used are described in Table I below.

TABLE I

| Cancer cell tissue type | Drug-sensitive "parent" cell line | Multidrug resistant cell line derived from a clone of the "parent" drug-sensitive cell line | Source of cells |
| --- | --- | --- | --- |
| Promyelocytic leukemia | HL60 | HL60/AR | American Tissue Culture Collection (ATCC), Manassas, VA and Aurelium BioPharma |
| Promyelocytic leukemia | NB4 | NB4/VLB NB4/DOX | Deutsche Sammlung von Miroorganismen und Zellkulturen GmbH (DSMZ, Germany) & Aurelium BioPharma |
| T lymphoblastoid | CEM | CEM/VLB CEM/DOX | ATCC and Dr. William Beck, Aurelium |
| T lymphoblastoid | HSB2 | HSB2/VLB HSB2/DOX | ATCC & Aurelium BioPharma |
| T lymphoblastoid | Molt4 | Molt4/DOX Molt4/VLB | ATCC & Aurelium BioPharma |
| Breast epithelial | MCF-7 | MCF-7/AR | ATCC and McGill University |
| Breast epithelial | MDA | MDA/AR MDA/MITO | ATCC and Aurelium BioPharma |
| Ovarian | SKOV-3 2008 | SKOV-3/T320 2008/T320 | ATCC and Aurelium BioPharma |

*MDR cells lines are named systematically using the parent cell line followed by a forward slash and abbreviation for the name of the drug used in selecting resistance in the parent cell line. Drug abbreviations in this table include: AR (adriamycin); VLB (vinblastine); DOX (doxorubicin); MITO (mitomycin); and T320 (taxol).

Cells were grown in RPMI or α-MEM medium, containing 10% to 15% fetal calf serum (commercially available from Hyclone Inc., Logan, Utah). The cells were grown in the absence of antibiotics at 37° C. in humid atmosphere of 5% $CO_2$ and 95% air, and passaged when cultures were $1 \times 10^6$ cells/ml. Multidrug resistant (MDR) cells (HL60/AR, NB4/VLB, NB4/DOX, CEM/VLB, CEM/DOX, Molt4/VLB, Molt4/DOX, HSB2/VLB, HSB2/DOX) (Aurelium Biopharma Inc., Montreal (Quebec), Canada) were grown continuously with appropriate concentrations of cytotoxic drugs. Similarly adherent cells were grown in α-MEM medium (MCF-7) or DMEM (MDA), containing 10% fetal calf serum. Multidrug resistant cells (MCF-7/AR, MDA/AR and MDA/MITO) were grown continuously with appropriate concentrations of cytotoxic drugs. All cell lines were examined for and determined to be free of mycoplasma contamination using a PCR-based mycoplasma detection kit according to manufacturer's instructions commercially available (e.g., from Stratagene Inc., San Diego, Calif.). All multidrug resistant cell lines were routinely tested for multidrug resistance using a panel of different drugs representing different classes of drugs. The MDR cells also expressed other MDR markers on their cell surface in addition to HSC70.

B. Cell Preparations

Different types of extracts were prepared from each cell type. Cells were concentrated and lysed according to standard procedures to obtain total cell extracts from the cells (e.g., Ausubel et al., *Current Protocols in Molecular Biology*, John Wiley & Sons Inc., New York City, N.Y. 1993). Alternatively, cells were first surface biotinylated and then lysed to obtain biotinylated total cell extracts (as shown in Examples below). To do these studies, intact drug sensitive (CEM and HL60) and multidrug resistant cells (CEM/VLB and HL60/AR) were biotinylated with a membrane impermeable biotinylating agent, Sulfo-NHS-LC-LC-Biotin (Pierce Chemicals, Rockford, Ill.). Cells were biotinylated by washing 3× with 50 ml PBS, pH 8. Next, Sulfo-NHS-LC-LC-Biotin (Pierce Chemicals, Rockford, Ill.) was prepared at 0.1–0.5 mg/ml and added to cells. The incubation with Sulfo-NHS-LC-LC-Biotin was allowed to continue for one hour at 4° C. with rotation. The reaction was stopped by washing cells one time with 50 ml PBS, pH 8, containing 10 mM glycine and several times with 50 ml PBS without glycine. Cells were then lysed in 200 µl of buffer A (1% SDS and 0.05 M Tris-HCl, pH 7.4), containing protease inhibitors (1 µg/ml pepstatin, 1 µg/ml Leupeptin; 1 µg/ml benzamidine; 0.2 mM PMSF) and incubated 5 minutes on ice. The cell lysate was then sonicated with a Vibracell sonicator (Sonics, Newtown, Conn.) amplitude 40 setting #25 for 3×10 seconds with one minute on ice between shots. The sonicated lysate was mixed with 800 µl of buffer B (1.25% Triton-X100, 0.05 M Tris/HCl, pH 7.4, 190 mM NaCl) containing protease inhibitors and incubated 5 minutes on ice. The cell lysate was then centrifuged at 14,000 rpm in an Eppendorf microfuge for 5 minutes. The supernatant was removed and its protein concentration was determined using the DC protein assay kit from BIORAD according to manufacturer's instructions (BioRad Laboratories, Hercules, Calif.) (see also Lowry, et al., *J. Biol. Chem.* 193: 265–75, 1951).

The use of this sulfo-LC-LC-biotinylating agent ensured the modification of the ε amino group on the lysine side chain in proteins exposed on the cell surface; conversely, intracellular proteins were not expected to be biotinylated since this sulfo-biotin cannot cross the cell membrane of intact cells.

In addition, plasma membrane preparations were prepared from surface biotinylated or nonbiotinylated cells of each type. To do this, $3 \times 10^9$ cells (of each cell type) were suspended in 12.5 ml of hypotonic buffer 1 (10 mM NaCl, 1.5 mM $MgCl_2$, 10 mM Tris-HCl, pH 7.4) and incubated for 10 minutes on ice. The cells were then homogenized in a Dounce glass homogenizer type B (15 ml). The degree of cell lysis was determined by examining cells under the microscope. Approximately 40 strokes were required to break about 85% of the cells. Immediately after homogenization, half volume (6.25 ml) of 2.5× buffer II (Buffer 1×: 210 mM mannitol, 70 mM sucrose, 5 mM Tris-HCl, pH 7.5, 1 mM EDTA, pH 7.5) was added to the cell homogenate and mixed. The homogenate was spun at 1300×g (3300 RPM) for 5 minutes in a Sorvall centrifuge using SS34 rotor (brake off). The pellet containing the nuclei fraction was separated from the supernatant containing cell membranes and organelles. The post-nuclei supernatant was spun or centrifuged again at 17000×g (11900 RPM) 15 minutes in a Sorvall centrifuge using the SS34 rotor (brake off). The mitochondrial-enriched pellet was separated from the membrane enriched supernatant fraction (post-mitochondrial fraction). The latter supernatant was centrifuged for 2 hours at 100,000×g in the Sorvall Ultracentrifuge using the T-1250 rotor in the capped tubes catalog no. 03989 S/L PA (35 ml) at 4° C. The cytosolic enriched supernatant was carefully removed, and the membrane enriched membrane pellet was resuspended in 300 µl of buffer 1 above and mixed well using a 27 gauge needle. The cell membranes were further enriched by resolving the last membrane pellet on a discontinuous sucrose gradient (16%, 31%, 45%, 60% w/v sucrose/buffer 1). Briefly, equal volume (about 350 µl) of 32% w/v of sucrose in buffer 1 (16% w/v final) was added to the resuspended pellet of enriched membrane material following 100,000×g centrifugation step. The sucrose gradient was prepared with 6.9 ml of 60% sucrose at the bottom of the tube followed by 9.9 ml of 45% sucrose, 13.9 ml 31% sucrose and 6.9 ml of 16% sucrose. Next, a 16% sucrose solution containing crude plasma membranes was slowly poured on the top of the gradient and the sample spun for 18–20 hours at 100,000×g at 4° C. in the Sorvall ultracentrifuge using the AH-629 rotor and PA UltraClear tubes from Beckman catalog no. 344058. The interphase between the 16% and 31% sucrose containing a highly enriched cell membrane was collected and washed once by centrifugation with buffer 1. Following a 100,000×g centrifugation in the ultracentrifuge the highly enriched cell membrane pellet was resuspended in an appropriate volume (about 50 µl) of buffer 1 and stored at −80° C. Plasma membrane extracts were prepared similarly from non-biotinylated and biotinylated cells (shown in Example II, FIG. 1).

Alternatively, total membrane extracts were prepared from surface biotinylated or non-biotinylated cells. For each cell type, cells were washed three times with 50 ml of ice-cold phosphate buffered saline (PBS), and resuspended in 100 µl PBS containing protease inhibitors. Cells were sonicated three times for twenty seconds each, and were spun at 4° C. for thirty minutes at 20,000 rpm. The pellet was resolubilized in PBS containing 4% CHAPS with protease inhibitors and stored at −80° C. until use.

C. Gel Electrophoresis

Equivalent amounts of protein from surface tiotinylated total cell extracts (containing biotinylated and non-biotinylated proteins) and plasma membrane or total membrane preparations from each of the cell types (HL60, HL60/AR, NB4, NB4/DOX, CEM, CEM/VLB, CEM/DOX, Molt4, Molt4/AR, Molt4/VLB, HSB2, HSB2/VLB, HSB2/DOX, MCF7, MCF7/AR, MDA, MDA/AR, MDA/MITO) were analyzed by 2-D gel electrophoresis and visualized by either blue or silver staining or immunoblotting with anti-HSC70 antibody or streptavidin-HPR conjugate (streptavidin binds biotin). This allowed resolution of protein samples according to differences in their isoelectric points in the first dimension and molecular masses in the second dimension.

For the first dimension, isoelectric focusing was achieved using 13 cm immobilized pH gradient strips (Amersham Pharmacia Biotech, Piscataway, N.J.). Briefly, the 13 cm strips were rehydrated in a ceramic strip holder in 250 µl rehydration buffer containing the protein samples (0.5–2 mg proteins) for 15 hours at 30 volts. Electrode pads were then placed over each electrode and the proteins separated on an IPGphor unit using the following program:

13 cm strips (pH 4–7):
 −500V for 500 Vh
 −1000V for 1000 Vh
 −8000V for 16000 Vh The strips were then slightly rinsed with water and equilibrated in 1% DTT in equilibration buffer for 15 minutes, followed by 4% iodoacetamide in equilibration buffer for 15 minutes.

For the second dimension, the above isoelectric strips were patient to sodium dodecyl sulfate-polyacrylamide gel electrophoresis (SDS-PAGE) using an 8% or 10% gel, according to the method of Laemmli (Laemmli U.K., *Nature* 227: 680–685, 1970). Molecular weight markers were loaded onto a 2×3 mm filter paper and placed at one end of the strip. The strip and molecular weight marker filter were then sealed onto the polyacrylamide gel with a 0.5% agarose solution in running buffer. Proteins were slowly transferred from the strip to the gel at 30 V at room temperature for an hour and the separation was carried out at 4–8° C. for 17–18 hours at 70 V or 75 V for 8% or 10% gels respectively.

The gels were next stained with blue or silver stain, and photographed. (Note, that at this point, the gel-resolved proteins can also be transferred onto Hybond C nitrocellulose membrane and then immunoblotted with antibody or streptavidin-HRP, as described below in the Examples).

D. Results

As shown in FIG. 1, two proteins corresponding to two isoforms of an approximately 71 kDa protein were present in plasma membrane cell extracts of CEM and CEM/VLB cells. Isoform 1 was initially named UR4 and isoforms 2 was initially named NC. The pI's of isoforms 1 and 2 are 5.58 and 5.51 respectively. Multidrug resistant T-lymphoblastoid CEM/VLB cells expressed at least 2-fold higher levels of isoform 2 than did drug sensitive CEM cells.

Example 2

5.2 Identification of the 71 kDa Protein of T-lymphoblastoic Cancer Cells as HSC70

To discover the identity of the approximately 71 kDa protein of T-lymphoblastoic CEM and CEM/VLB cells (spots pointed to by the arrow on the gels shown in FIGS. 1A and 1B), 2-D gels were loaded with CEM/VLB plasma membrane extracts (2×750 µg, pI 4–7, 10% gel), the gels were silver-stained, and the 71 kDa spots were excised. The spots were processed using optimized procedures for staining/destaining of gels, trypsin digestion, peptide extraction and peptide purification. Briefly, gels were stained with SilverQuest silver stain (Invitrogen) according to manufacturer's instructions. The protein spots of interest were excised with a clean (acid washed) razor blade, cut into small pieces on a clean glass plate and transferred into a 200 µl PCR tube (MeOH treated), mixed with 50 µl destainer A and 50 µl destainer B (provided with SilverQuest kit) (or 100 µl of the destainers premix prepared fresh), and incubated for 15 minutes at room temperature without agitation. The wash was removed. Water was added to the gel pieces, mixed, and incubated 10 minutes at room temperature. The latter step was repeated three times. The gel pieces were then dehydrated in 100 µl 100% methanol for 5 minutes at room temperature, followed by rehydration in 30% methanol/water for 5 minutes. Gel pieces were then washed twice in water for ten minutes and twice in 25 mM Ambic (ammonium bicarbonate)/30% acetonitrile followed by a gel drying step. Tryptic digestion of the destained and washed gel pieces was performed by adding one volume of trypsin solution (130 ng of enzyme in 25 mM ammonium bicarbonate, 5 mM $CaCl_2$) to one volume of gel pieces and samples left on ice for 45 minutes. The digestion was allowed to proceed for 15–16 hours at 37° C. Digested peptides were extracted with acetonitrile for 15 minutes at room temperature with shaking. The gel pieces/solvent were sonicated 5 minutes and reextracted with 25 mM Ambic/50% acetonitrile without sonication. Digested peptides were further extracted with 5% formic acid/50% acetonitrile/45% water freshly prepared for 15 minutes at room temperature with shaking. The mix was completed with one volume of acetonitrile and the gel pieces/solvent were sonicated 5 minutes and reextracted the same way without sonication. The collected material was combined and dried. The extracted peptides were resuspended in 5% methanol with 0.2% trifluroacetic acid (or 0.5% formic acid) then loaded on an equilibrated C18 bed (Ziptip from Millipore). The loaded Ziptip was washed with 5% acetonitrile containing 0.2% TFA (or 0.5% formic acid) and then eluted with 10 µl of 60% acetonitrile. The eluted peptide solution was dried and analyzed using MALDI mass spectroscopy (Mann, et al., *Ann. Rev. Biochem.*, 70: 437–73, 2001).

The mass spectrogram of the 71 kDa isoform 2 spot (following purification and protease digestion) consisted of over 20 tryptic peptides, of which 12 peptides were from the 71 kDa protein, while the remaining peptides were trypsin autodigestion products. The 71 kDa peptides were further analyzed using a sequence database search shareware software program called ProFound™. ProFound was used to search public databases for protein sequences (e.g., non-redundant collection of sequences at the US National Center for Biotechnology Information (NCBInr)). The NCBInr database contains translated protein sequences form the entire collection of DNA sequences kept at Genbank, and also the protein sequences in the PDB, SWISS-PROT and PIR databases.

As shown in FIG. 2A, using the ProFound™ program, the 71 kDa isoforms 2 protein was identified as HSC70 with a probability Z-score of 2.36, which is in the $99^{th}$ percentile, based on the analysis of the 12 tryptic peptide sequences that covered 25% of the HSC70 complete amino acid sequence (FIGS. 2B and C). Two values are taken into account when evaluating a ProFound™ analysis result: the Z probability score and the % coverage (the percent of the peptides' amino acid sequences relative to the identified protein's complete amino acid sequence). Z=1.65–2.43 is an acceptable range of scores. Z=1.65 means that the result is in the $95^{th}$ percentile and Z=2.43 means that the result is in the $99.9^{th}$ percentile. Thus the Z score of 2.36 indicated that the 71 kDa spot peptide sequences corresponded to those of HSC70 with a high degree of probability.

The amino acid sequence of HSC70 protein is shown in FIG. 3 which also shows the location of sequence of the 12 tryptic peptides in bold font. The sequences of the 12 peptides were spread throughout the HSC70 molecule and together corresponded to 25% of the complete HSC70 protein amino acid sequence, hence the protein identified was the full length protein and not a fragment or fusion protein.

Example 3

5.3 The 71 kDa Protein is Expressed on the Cell Surface of Multidrug Resistant Promyelocytic Leukemia Cancer Cells To determine whether HSC70 was present on the inside or outside of the cell membrane, intact promyelocytic leukemia tumor cells (HL60 and HL60/AR) were treated as described above with a membrane impermeable biotinylating reagent that reacts with lysines, and total cell extracts from both drug sensitive (HL60) and multidrug resistant (HL60/AR) were prepared.

Two equivalent sets of 2-D gels of HL60 and HL60/AR were prepared and GelCode blue (Pierce #24592, Rockford, Ill.) stained. FIG. 4 represents the area corresponding to the presumed location of HSC70 on a 2D gel (MW=71.11 kDa, pI=5.4). There was a 2-fold increase in expression of the approximately 71 kDa protein in total extracts of multidrug resistant HL60/AR cells as compared to the drug-sensitive HL60 cells (compare FIGS. 4(A) and 4(B)).

To discover the identity of this protein, the 71 kDa spot (marked by arrows on FIGS. 4(A) and 4(B)) was excised and processed to prepare a sample for MALDI analysis as described in Example II above. The mass spectrogram of the 71 kDa spot (following tryptic digestion and peptide purification) consisted of 20 tryptic peptides, of which 12 peptides were from the 71 kDa protein while the remaining peptides were trypsin autodigestion products. The 71 kDa peptides were further analyzed using the sequence database search shareware software program called ProFound™.

As shown in FIGS. 5A and 5B, using the ProFound™ program, the 71 kDa protein was identified as HSC70 with a probability Z-score of 2.43, which is in the $99.9^{th}$ percentile, based on the analysis of the 12 tryptic peptide sequences that covered 26% of its complete amino acid sequence (FIG. 5C). The Z score of 2.43 indicated that the 71 kDa spot peptide sequences corresponded to those of HSC70 with the highest degree of probability. As shown in FIG. 5C, 3 out of 12 peptides were biotinylated.

The amino acid sequence of HSC70 protein is shown in FIG. 6 which also shows the location and sequence of the nine tryptic peptides that were not biotinylated (in bold font), as well as the three peptides that were biotinylated (in italic font). The sequences of the 12 peptides were spread throughout the HSC70 molecule and together corresponded to 26% of the complete HSC70 protein amino acid sequence; hence the protein identified was the full-length protein and not a fragment or fusion protein. The biotinylated region that is shown in italic font in FIG. 6 was detected in two ways. First, the bound biotin moiety changed the mass of the peptide containing it relative to the non-biotinylated peptide, and second, biotinylated peptides bound to streptavidin beads (immobilized streptavidin beads commercially available from Pierce #20347), whereas non-biotinylated peptides did not.

To demonstrate that HSC70 is overexpressed on the surface of HL60/AR cells, total membrane and plasma membrane extracts were resolved by 1D-PAGE, transferred onto nitrocellulose, and blotted with anti-HSC70 (SPA-815, Stressgen). FIG. 7 shows that HSC70 was overexpressed in the total membrane extracts as well as plasma membrane extracts of multidrug resistant HL60/AR as compared to HL60.

Example 4

5.4 HSC70 is Expressed on the Cell Surface of Multidrug Resistant Promyelocytic Leukemia Cancer Cells To confirm that HSC70 was present on the outside of the cell membrane, intact promyelocytic leukemia tumor cells (HL60 and HL60/AR) were treated as described above in Example I with a membrane impermeable biotinylating reagent that reacts with the amino acid lysine, and total cell extracts from both drug sensitive (HL60) and multidrug resistant (HL60/AR) were prepared.

To do this, cells were biotinylated by washing 3× with 50 ml PBS, pH 8. Next, Sulfo-NHS-LC-LC-Biotin (Pierce Chemicals) was prepared at 0.1–0.5 mg/ml and added to cells. The incubation with Sulfo-NHS-LC-LC-Biotin was allowed to continue for 1 hour at 4° C. with rotation. The reaction was stopped by washing cells one time with 50 ml PBS pH 8, containing 10 mM glycine and several times with 50 ml PBS, without glycine. Cells were then lysed in 200 µl of buffer A (1% SDS and 0.05 M Tris/HCl, pH 7.4), containing proteases inhibitors 1 µg/ml pepstatin, 1 µg/ml Leupeptin; 1 µg/ml benzamidine; 0.2 mM PMSF) and incubated 5 minutes on ice. The cell lysate was then sonicated with a Vibracell sonicator amplitude 40 setting #25 for 3×10 seconds with 1 minute on ice between shots. The sonicated cell lysate was mixed with 800 µl of buffer B (1.25% Triton-X100, 0.05 M Tris/HCl,pH 7.4, 190 mM NaCl), containing proteases inhibitors and incubated 5 minutes on ice. The cell lysate was next centrifuged at 14,000 rpm in an Eppendorf microfuge for 5 minutes. The supernatant was removed, and its protein concentration was determined using the DC protein assay kit from BIORAD according to manufacturer's instructions (BioRad Laboratories, Hercules, Calif.) (see also Lowry et al., *J. Biol. Chem.* 193: 265–275, 1951).

In addition, streptavidin purified biotinylated proteins were prepared from the surface biotinylated total cell extracts of HL60 and HL60/AR cells using immobilized streptavidin (commercially available from Pierce, catalog no #20347 or Amersham Pharmaca Biotech RPN1231). To do this, 50 µl samples containing 500 µg to 2 mg protein were diluted to 450 µl final with buffer C (1:4 v/v of buffers A and B above), containing proteases inhibitors. Samples were then centrifuged at 14,000 rpm in an eppendorf microfuge for 1 minute. The supernatant was transferred to a new Eppendorf tube and mixed with 100 µl of Streptavidin-linked sepharose beads. The protein lysate together with the linked sepharose beads were incubated with rotation overnight at 4° C. The mix was centrifuged at 14,000 rpm for 30 seconds in an eppendorf microfuge. The supernatant was removed and the protein loaded beads were washed 3 times with buffer C, then with 500 mM NaCl in buffer C and buffer C again. Proteins were eluted from the Streptavidin-linked beads with SDS sample buffer following 10 minutes boiling. Elution was repeated and volumes pooled.

Equivalent amounts of protein from HL60 and HL60/AR (promyelocytic leukemia) cell surface biotinylated total cell extracts (FIG. 8A) and streptavidin purified cell surface biotinylated extracts (FIG. 8B) were resolved by SDS-PAGE according to the method of Laemmli (supra) and subjected to Western blotting analysis and probed with either anti-HSC70 antibody (rat monoclonal SPA-815, Stressgen) (FIGS. 8A and 8B), or with horseradish peroxidase (HRP)-linked streptavidin (which specifically binds to biotinylated proteins, Amersham RPN 1231) (FIG. 8D). To do this, gels containing separated proteins were transferred onto Hybond C nitrocellulose membrane (Amersham, Piscataway, N.J.) according to the method of Towbin (Towbin, H. T., *Proc. Natl. Acad. Sci. U.S.A.* 76:4350–4354, 1979). The nitrocellulose membranes were then probed with antibody or HPR-streptavidin. Binding of the antibody was detected with peroxidase conjugated rabbit anti-rat secondary antibody (Sigma, A5795, St. Louis, Mo.). Both secondary antibody and HRP-linked streptavidin were detected using the ECL chemiluminescent detection kit commercially available from Pierce. Relative protein levels were detected by exposure in the dark to XAR films (Kodak, Rochester, N.Y.).

As shown in FIG. 8A anti-HSC70 antibody bound to HSC70 protein which was expressed at significantly higher levels in surface biotinylated total cell extracts of multidrug resistant HL60/AR cells compared to HL60 cells. HSC70 was also overexpressed in streptavidin purified cell surface biotinylated proteins of HL60/AR cells compared to HL60 cells (FIG. 8B).

To confirm that HSC70 was present on the cell surface was indeed biotinylated, surface biotinylated total cell extracts from HL60 and HL60/AR cells were immunoprecipated with anti-HSC70 antibody (FIGS. 8C and 8D), and the immunoprecipates were resolved on SDS-PAGE and Western blotted. To do this, samples were prepared as described above using Protein A Sepharose beads instead of streptavidin beads. To elute the proteins from the Protein A Sepharose beads, the loaded beads were washed five times with Buffer D (0.03% SDS, 0.05 M Tris-HCl, pH 7.4, 0.1% Triton X-100, 5 mg/ml BSA fraction V, 150 mM NaCl) and one time with Buffer E (150 mM NaCl, 0.05 M Tris-HCl, pH 7.4), containing protease inhibitors as above. Proteins were eluted from the beads with SDS sample buffer following 10 minutes incubation at room temperature with vortex every 1 minute. Protein elution from the beads was repeated one more time and the volumes pooled. Proteins were resolved by SDS-PAGE and Western blotting as before with either anti-HSC70 monoclonal antibody or HRP-labeled streptavidin.

The blots were probed with anti-HSC70 antibody (FIG. 8(C)) and with streptavidin-HRP (FIG. 8D). As expected, HSC70 was detected in the immunoprecipitates from both cell types (FIG. 8C), however, significantly more cell surface biotinylated HSC70 was present in the anti-HSC70 immunoprecipitates from HL60/AR cells compared with those from HL60 cells (FIG. 8(D)).

These results, taken together, suggest that translocation of HSC70 across the plasma membrane to the cell surface, as well as additional de novo synthesis of HSC70, was associated with multidrug resistance in HL60/AR cells.

Example 5

5.5 HSC70 is Expressed on the Cell Surface of Multidrug Resistant of T-lymphoblastoic Cancer Cells To determine whether HSC70 was present on the inside or outside of the cell membrane, intact T-lymphoblastoic cancer cells (CEM and CEM/VLB) were treated with a membrane impermeable biotinylating reagent that reacts with the amino acid lysine, and total cell extracts from both drug sensitive (CEM) and multidrug resistant (CEM/VLB) were prepared. In addition, streptavidin purified biotinylated proteins as well as anti-HSC70 immunoprecipates were prepared from the surface biotinylated total cell extracts of CEM and CEM/VLB cells, resolved on SDS-PAGE and transferred onto nitrocellulose as described above.

As shown in FIG. 9A anti-HSC70 antibody bound to HSC70 protein which was expressed at slightly higher levels in surface biotinylated total cell extracts of multidrug resistant CEM/VLB cells compared to CEM cells. HSC70 was also slightly overexpressed in streptavidin purified cell surface biotinylated proteins of CEM/VLB cells compared to CEM cells (FIG. 9B). In addition, the immunoprecipitates blots were probed with anti-HSC70 antibody (FIG. 9C) and with streptavidin-HRP (FIG. 9D). As expected, significantly more cell surface biotinylated HSC70 was present in the anti-HSC70 immunoprecipitates from CEM/VLB cells compared with those from CEM cells (FIG. 9D).

These results, taken together, suggest that translocation of HSC70 across the plasma membrane to the cell surface, as well as additional de novo synthesis of HSC70, was associated with multidrug resistance in CEM/VLB cells.

Example 6

5.6 Characterization of HSC70 Expression on the Cell Surface of Multidrug Resistant Promyelocytic Leukemia Cancer Cells HL60 and HL60/AR cells were analyzed by cell surface staining and analysis to determine the difference in cell surface expression of heat shock cognate protein on the two cell lines. To do this, indirect immunofluorescence analysis was performed using 10 µ, 20 µ and 40 µg of anti-HSC70 as primary antibody (rat anti-HSC70. Stressgen SPA-815, San Diego, Calif.), followed by rabbit anti-rat IgG FITC-conjugated secondary antibody (Sigma, F1763).

Cells were washed three times in 50 ml PBS, pH 7.4 and 0.1% NaN$_3$ and counted. 1×10$^6$ cells per sample were placed in 100 µl PBS and 0.1% NaN$_3$ in 12×75 mm tubes or deep 96 well plate. The first antibody was added and incubated for 20 minutes at 37° C. 3 ml (or 1.25 ml in plate) PBS pH 7.4 and 0.1% NaN$_3$ was added the mixture was spun for 5 minutes (1000 rpm/200×g). The supernatant was discarded and the pellet was resuspended in 100 µl PBS pH 7.4 and 0.1% NaN$_3$.

The second Ab (FITC conjugated) was added. The mixture was prepared by diluting half in PBS, pH 7.4 and 0.1% NaN$_3$ and spun at maximum speed for 30 minutes at 4° C. Separate from pellet and use a 1/10 for staining. Incubate for 20 minutes at 37° C. 3 ml (or 1.25 ml in plate) PBS pH 7.4 and 0.1% NaN$_3$ was added and the mixture spun 5 minutes (1000 rpm/200×g). The supernatant was discarded and the addition of PBS and NaN$_3$ was repeated. The mixture was spun again for 5 minutes (1000 rpm/200×g).

1 µg–2 µg/µl of EMA was added. The mixture was incubated in white light on ice for 10 minutes. 3 ml (or 1.25 ml in plate) PBS, pH 7.4 and 0.1% NaN$_3$ was added and the mixture spun 5 minutes (1000 rpm/200×g). The supernatant was discarded and the addition of PBS and NaN$_3$ was repeated. The mixture was spun again for 5 minutes (1000 rpm/200×g) and resuspended in 500 µl PBS, pH 7.2/2% paraformaldehyde and store in the dark at 4° C. For each sample, 10,000 cells were analyzed using a fluorescence-activated cell sorter (Beckman Coulter XL MCL). The fluorescence emission corresponding to specifically stained cells was calculated by subtracting the emission measured for cells at 530 nm stained with rat IgG2a isotype (Cymbus, #CBL605).

As shown in FIG. 10A, HSC70 was expressed on the surface of multidrug resistant HL60/AR cells at a level approximately 3 to 10 fold higher than expressed on the surface of drug sensitive HL60 cells, depending on how much primary antibody was used.

The number of molecules of HSC70 expressed on the surface of HL60 and HL60/AR cells was determined by FACS using a Quantum Simply Cellular flow cytometry quantification kit (Sigma #QSC20 (6951-213369 molecules) at saturating amounts of antibody for the beads and for the cells. The QSC system consists of microbeads of approximately the size of lymphocytes that are coupled to goat anti-mouse antibodies. A set of five populations of microbeads bearing different known amounts of goat anti-mouse antibodies are provided in the kit. The microbeads are incubated with saturating amounts of the mouse monoclonal antibody of interest. The fluorescence intensities obtained with the microbeads are plotted to create a standard curve of the fluorescence intensity to the number of antibody molecules bound on the beads. The signal obtained with the cells (at saturating amounts) is then, using the standard curve, correlated to the number of antibody molecules bound to the cells, which corresponds to the number of antigens present on the surface of the cell. 60 µg of mouse anti-HSC70 IgG2a (Santa-Cruz, sc-7298) were used in two independent experiments, and 30 µg of the antibody were tested with QSC beads purchased from Sigma (6951-213369 molecules) in the same conditions as with the cells. The calibration curve obtained with the beads was used to convert the RFI into number of molecules. As shown in FIG. 10B, the averaged number of molecules of HSC70 on the surface of HL60 and HL60/AR was 2541±1184 and 7189±590 molecules for HL60 and HL60/AR, respectively.

Example 7

5.7 Characterization of HSC70 Expression on the Cell Surface of Multidrug Resistant Lymphocytic Leukemia Cancer Cells CEM and CEM/VLB cells were analyzed by cell surface staining and FACS analysis to determine the difference in cell surface expression of HSC70 on the two cell lines. To do this, indirect immunofluorescence analysis was performed using 1 µ, 2.5 µg and 5 µg of anti-HSC70 as primary antibody (rat monoclonal antibody, Stressgen SPA-815) followed by FITC-conjugated secondary antibody. Cells were washed three times in 50 ml PBS, pH 7.4 and 0.1% NaN$_3$ and counted. 1×10$^6$ cells per sample were placed in 100 µl PBS and 0.1% NaN$_3$ in 12×75 mm tubes or deep 96 well plate. The first antibody was added and incubated for 20 minutes at 37° C. 3 ml (or 1.25 ml in plate) PBS, pH 7.4 and 0.1% NaN$_3$ was added the mixture was spun for 5 minutes (1000 rpm/200×g). The supernatant was discarded and the pellet was resuspended in 100 µl PBS, pH 7.4 and 0.1% NaN$_3$.

The second Ab (FITC conjugated) was added. The mixture was diluted by half in PBS, pH 7.4 and 0.1% NaN$_3$ and spun at maximum speed for 30 minutes at 4° C. The supernatant was separated from the pellet and 1/10 was used for staining. The mixture was incubated for 20 minutes at 37° C. 3 ml (or 1.25 ml in plate) PBS, pH 7.4 and 0.1% NaN$_3$ was added and the mixture spun 5 minutes (1000 rpm/200× g). The supernatant was discarded, and the addition of PBS and NaN$_3$ was repeated. The mixture was spun again for 5 minutes (1000 rpm/200×g).

1 μg–2 μg/μl of EMA was added. The mixture was incubated in white light on ice for 10 minutes. 3 ml (or 1.25 ml in plate) PBS, pH 7.4 and 0.1% NaN$_3$ was added and the mixture spun 5 minutes (1000 rpm/200×g). The supernatant was discarded and the addition of PBS and NaN$_3$ was repeated. The mixture was spun again for 5 minutes (1000 rpm/200×g). Resuspended in 500 μl PBS pH 7.2/2% paraformaldehyde and store in the dark at 4° C.

For each sample, 10,000 cells were analyzed using a fluorescence-activated cell sorter (Beckman Coulter, XL MCL). The fluorescence emission corresponding to specifically stained cells was calculated by subtracting the emission measured for cells at 530 nm stained with rat IgG2a isotype (Cymbus, CBL605).

As shown in FIG. 11A, HSC70 was expressed on the surface of multidrug resistant CEM/VLB cells at a level approximately two fold higher than expressed on the surface of drug sensitive CEM cells.

The number of molecules of HSC70 expressed on the surface of CEM and CEM/VLB cells was determined by applying the fold difference obtained when comparing CEM/VLB to HL60/AR (FIG. 11B), to the number of molecules obtained for HL60/AR (see Example VI). As seen in FIG. 11C, the number of molecules of HSC70 present on the surface of CEM/VLB is 10972 molecules.

Example 8

5.8 Characterization of HSC70 Expression on the Cell Surface of Multidrug Resistant Breast Cancer Cells MCF-7, MCF-7/AR, MDA, and MDA/AR breast cancer cells were analyzed by cell surface staining and FACS analysis to determine the difference in cell surface expression of HSC70 on the two multidrug resistant breast cancer cell lines. To do this, indirect immunofluorescence analysis was performed using 10 μg of rat monoclonal anti-HSC70 as primary antibody (SPA-815-Stressgen), followed by rabbit anti-rat IgG FITC-conjugated secondary antibody (Sigma, F1763). In addition, indirect immunofluorescence analysis was performed using 1 μg of mouse monoclonal anti-Pgp (#801-008-C150, clone MRK-16, Alexis Biochemicals), followed by goat anti-mouse IgG FITC-conjugated secondary antibody (AP181F, Chemicon). The multidrug resistance marker Pgp was tested in parallel as a positive control.

The cells were prepared as described above for FACS analysis. For each sample, 10,000 cells were analyzed using a fluorescence-activated cell sorter (Beckman Coulter XL MCL). The fluorescence emission corresponding to specifically stained cells was calculated by subtracting the emission measured for cells at 530 nm stained with 10 μg of rat IgG2a (Cymbus, #CBL605) or 1 μg of mouse IgG2a (Sigma, M9144) isotype control (for HSC70 and Pgp respectively).

The results of FACS analysis are represented in a bar graph in FIGS. 12A and 12B. As can be seen, HSC70 was expressed on the surface of MCF-7/AR cells at a level three fold higher than the level of HSC70 expressed on the surface of MCF-7 cells (FIG. 12A). FIG. 12B represents the FACS results for MDA/AR cells, and shows that HSC70 was expressed on the surface of MDA/AR cells at a level two folds higher than the level of HSC70 expressed on the surface of MDA cells.

Example 9

5.9 HSC70 is Expressed on the Cell Surface of Hematological Cancer Cells and at Higher Levels on MDR Hematological Cancer Cells, but is Absent on Normal Cells Normal white blood cells were next compared to hematological cancer cells and MDR hematological cancer cells to determine the difference in levels of cell surface expressed HSC70. To do this, indirect immunofluorescence analysis was performed using 5 μg of rat monoclonal anti-HSC70 as primary antibody (SPA-815-Stressgen), followed by rabbit anti-rat IgG FITC-conjugated secondary antibody (Sigma, F1763).

Human blood samples (collected in heparin tubes) were obtained from donors and were processed within an hour. Briefly, erythrocytes were separated from leukocytes and plasma on a Ficoll hypaque gradient (Histopaque Sigma 1077-1). Specifically, 15 ml of blood was diluted one-half in pH 7.4 and put over equal volume of Ficoll gradient. Cells were separated by centrifugation 400×g for 30 minutes at room temperature. The upper phase (plasma) was removed until 0.5 cm from the plasma/Ficoll interface. Then, mononuclear cells (at the interface) were collected in a 50 ml Falcon tubes. The Ficoll was removed and then red blood cells (at the bottom of the tube) were collected. All cells types were washed with PBS two times by spinning 10 minutes at 250 g at 4° C. and counted. Leucocytes were then resuspended at 1×10$^7$ cells/ml, and 100 μl (1×10$^6$ cells) aliquots were used for flow cytometry (FACS) analysis.

The cells were prepared as described above for FACS analysis. For each sample, 10,000 cells were analyzed using a fluorescence-activated cell sorter (Beckman Coulter XL MCL). The fluorescence emission corresponding to specifically stained cells was calculated by subtracting the emission measured for cells at 530 nm stained with 5 μg of rat IgG2a (Cymbus, #CBL605).

Each FACS experiment was carried out with several controls, including cells alone to determine autofluorescence; cells plus EMA to identify dead cells during analysis; cells plus secondary antibody (Ab) alone to identify non-specific interactions due to secondary antibody; cells plus isotype matching antibodies (Abs) or appropriate host primary Abs control; cells (mononuclear cells) plus CD45-PC5 mouse monoclonal, phycoerythrin-Cyanine 5 conjugate (Immunotech PN IM2653) to establish and gate the different leukocyte populations.

When the expression levels of HSC70 on normal WBC were compared to the expression levels of HSC70 on various hematological cancer or MDR hematological cancer cells in comparison to the hematological cancer and MDR hematological cancer cells, normal cells do not express HSC70 on their cell surface (see FIG. 13B).

Example 10

5.10 Use of HSC70 as an Antigen for a Vaccine Against MDR Hematological Cancer Cells Example 10 HSC70-Based Vaccine Protection Against MDR Hematological Cancer Cells and MDR Mammary Adenocarcinoma Cells To determine whether or not the full length HSC70 protein expressed on the cell surface of MDR hematological cancer cells is useful as an antigen for a vaccine to immune animals against MDR hematological cancer cells, purified HSC70 protein is combined with an adjuvant (e.g., Freund's), and administered to groups of mice having a hematological cancer caused by the presence of a hematological cancer cell. One such non-limiting hematological cancer is acute lymphocytic leukemia.

To do this, the mice are injected with hematological tumor cells that are compatible with the mice's MHC type (or are injected into SCID mice). Some of the mice receive the injected tumor cells prior to being immunized with purified full length murine HSC70 protein; some receive the hematological tumor cell injection after being immunized with purified full length murine HSC70 protein. Note that the purified HSC70 protein may be administered with an adjuvant. Proper controls are performed for each group of mice (i.e., one control group receives only the purified murine HSC70 protein; another receives only the hematological tumor cell injection).

The tumors that form in the mice are weighed or measured (e.g., tumor cell number counted, tumor excised and weighed, or tumor measured by calipers). The mice that are vaccinated with HSC70 prior to injection of the tumor cells are found to have tumors that are smaller after treatment than those that were not vaccinated with HSC70 prior to injection of the tumor cells.

In further studies, the efficacy of HSC70 as an antigen against MDR mammary adenocarcinoma cells (MCF/AR) is assessed. Briefly, six week-old female mice are injected with 30–250 ug of whole HSC70 or control antigen administered with or without adjuvant S.C. and I.P or into rear footpads on days 1, 7, 14, 21, 28 and 35. After various intervals, blood samples are collected from the retro-orbital venous plexus for anti-HSC70 antibody assay. Mice are challenged on day 59 with 1.5×104 viable MDR mammary adenocarcinoma cells (MCF/AR) administered S.C. into the right flauk. Mice are examined twice a week and tumor incidence is determined from the number of mice bearing tumors. Tumor size was measured with a Vernier caliper. Survival rates are measured up to 80 days post challenge with adenocarcinoma.

Example 11

5.11 HSC70-Targeted Therapy Against MDR Hematological Cancer Cells

In order to determine whether targeting a therapeutic to cell surface HSC70 would be useful in treating a preexisting cancerous condition, hematological tumor cells are administered to MHC-matched mice, and tumors are allowed to form. Next, the mice are administered vincristine (or another chemotherapeutic drug) at a dosage predicted to kill most, but not all of the tumor cells in the mice. Those mice that are identified as having developed multidrug resistant tumor cells are administered a composition comprising vincristine and a binding agent that specifically binds to murine HSC70 protein, where the binding agent is operably linked to ricin toxin.

The mice that receive the composition show a better prognosis (i.e., smaller tumor or fewer tumor cells) as compared to mice that receive only the binding agent or only the vincristine.

In further studies, the efficacy of a HSC70-targeted therapeutic in treating an MDR mammary adenocarcinoma cells (MCF/AR) is assessed. Briefly, Athymic nude mice are used for the MCF-7/ADR xenografts. Male mice 5–7 weeks old, weighing 18–22 g, are used. Mice receive a subcutaneous (s.c.) injection of the cells using 0.5 million cells/inoculation under the shoulder. After s.c. implantation of the cells, when the s.c. tumour is approximately 5.5 mm in size, mice are randomized into treatment groups of four including controls and groups receiving vincristine or doxorubicin alone (4 mg/kg), intraperitoneally (i.p.) every 2 days, anti-HSC70 alone (100 ug–1 mg/kg) or both vincristine or doxorubicin and anti-HSC70 mAb (100 ug–1 mg/Kg), i.p. The animal's weight is measured every 4 days. Each animal is tagged in the ear and followed individually throughout the experiments. Tumor growth starting on the first day of treatment is measured and the volume of the xenograft is monitored every 4 days. The mice are anaesthetized and killed when the mean tumor weights is over 1 g in the control group. Tumor tissue is excised from the mice and its weight is measured.

Example 12

5.12 Characterization of Heat shock cognate protein (HSC70) Expression on the Cell Surface of Multidrug Resistant Breast Cancer Cells MCF-7 and MCF-7/AR cells were analyzed by immunostaining to determine the difference in cell surface expression of heat shock cognate protein 70 on the two cell lines. To do this, immunofluorescence analysis was performed using 0.5 ug of anti-HSC70 as primary antibody (rat anti-HSC70. Stressgen SPA-815) on permeabilized and non-permeabilized cells. Ethidium monoazide (EMA) was used to stain the nucleus of permeabilized or damaged cells.

FIG. 15A&B provides flow charts depicting the steps taken to stain cells. The control cells were MCF-7 and MCF-7/AR stained with 0.5 ug rat IgG2a and no staining was observed in the control cells in either the permeabilized or non-permeabilized cells (data not shown). As shown in FIG. 16, HSC70 was clearly expressed on the surface of intact multidrug resistant MCF-7/AR cells when MCF-7 didn't show any staining. Permeabilized cells showed equivalent total pool of HSC70 which was confirmed by western blot (FIG. 19).

A comparison of total pool of HSC70 for various sensitive and resistant cancer cells as well as normal tissue is shown in FIG. 19. Equivalent amounts of each extract were separated on a 10% SDS gel. Extracts of normal tissues were obtained from BD (brain #635301, lung #635304, ovary #635344, mammary gland #635308, prostate #635366) and extracts of white blood cells were prepared from cells purified from blood obtained from healthy donors (procedure for WBC purification is given in example IX of previous draft). All extracts (except ones purchased from BD) were prepared in 50 mM Tris pH8, 50 mM NaCl, 4% CHAPS supplemented with protease inhibitors and phosphatase inhibitors cocktails. Lysed cells were sonicated on ice, treated with DNAseI and lysates brought to 8M urea. FIG. 19 shows that HSC70 is overexpressed in all sensitive and resistant cancer cell lines tested, whereas normal cells express very little to undetectable HSC70. It is noteworthy that HSC70's increase in surface exposure measured for MCF-7 and MCF-7/AR cells isn't triggered by an increase in the intracellular pool of the protein since the total pool doesn't change significantly between sensitive and resistant cell lines.

Example 13

5.13 Qualitative Analysis of Cell Surface HSC70 Expression in MDR Breast Cancer Cells MCF-7 and MCF-7/AR cells are analyzed by immunostaining to determine the difference in cell surface expression of HSC70 on the two cell lines. To do this, immunofluorescence analysis is performed using 0.5 mg of anti-HSC70 as primary antibody on permeabilized and non-permeabilized cells. Ethidium monoazide (EMA) is used to stain the nucleus of permeabilized or damaged cells.

The control cells are MCF-7 and MCF-7/AR stained with 0.5 mg mouse IgG1 and no staining is observed in either the permeabilized or non-permeabilized cells (data not shown). HSC70 is clearly expressed on the surface of intact multidrug resistant MCF-7/AR cells while MCF-7 didn't show any staining.

Example 14

5.14 Quantitative Analysis of Cell Surface HSC70 Expression in MDR Promyelocytic Leukemia Cancer Cells HL60 and HL60/AR cells are analyzed for surface exposure of HSC70 by direct binding of 125-iodine labeled anti-HSC70 to the surface of the cells. To do this, anti-HSC70, mouse IgG1 (isotype matching negative control, Sigma, M-9035) and anti-CD33 (positive control, Serotec, #MCA1271) are iodinated using IODO-GEN® precoated iodination tubes (Pierce, #28601) following the procedure given by the manufacturer (average activity obtained: 7.5 mCi/mg).

Cells are washed twice with RPMI 1640 and resuspended at 106 cells/100 mL in the same media. Viability is assessed by trypan blue staining and is less than 5%. Cells (1×106) are aliquoted into borosilicate tubes and incubated for 1 hour on ice in the presence of 1 mg of radiolabeled anti-HSC70, IgG1 or anti-CD33. After incubation, cells are washed 3 times with 1 ml RPMI 1640 and the cell pellet is counted in a gamma-counter.

The results of the intact cell radioimmunoassay are represented assessed as the number of counts per minute obtained for the cell pellet, from which the IgG1 background has been subtracted. HSC70 is expressed on the surface of the resistant HL60/AR cells at a higher level than the level of HSC70 expressed on the surface of drug-sensitive HL60 cells.

Example 15

5.15 Cytotoxic effect of radioiodinated anti-HSC70 on HL60 and HL60/AR cells

Cells are washed twice with RPMI 1640 and resuspended at 106 cells/100 ml in the same media. Viability is assessed by trypan blue staining and is less than 5%. Cells (1×106) are aliquoted into borosilicate tubes and incubated for 4 hour at 37° C. (0.5% CO2) in the presence of 5 mg of sterile filtered radiolabeled anti-HSC70, IgG1 or anti-CD33 (iodination procedure is described in example above). After incubation, cells are washed once with 1 ml RPMI 1640, 10% FBS, 1 mM HEPES, resuspended in 1 ml of the same media and seeded at 5000 cells per well into a flat bottom tissue culture 96 well plate. The cytotoxicity of the radiolabeled antibodies is assessed after 72 hours in an MTT based assay. Anti-CD33 is used a positive control for surface binding of the antibody and 120 nM doxorubicin (Doxo) is used as positive control for cytotoxicity.

The results of the cytotoxicity assay are represented as values expressing percent viability. Values for percent survival with anti-HSC70 and anti-CD33 antibody-125I conjugates are normalized against the values obtained for the radiolabeled IgG1 (non-significant background binding, 100% viability). Values obtained with the anticancer drug doxorubicin are normalized against the values obtained for cells non-treated with drug.

The results show that radiolabeled anti-HSC70 has a cytotoxic effect on HL60 and HL60/AR which both express HSC70 on their surface.

Example 16

5.16 Molecular Quantitation of Cell Surface HSC70 in Drug Sensitive and Drug Resistant Breast and Ovarian Cancer Cell Lines Breast MCF-7, MCF-7/AR, MDA, MDA/mito, and ovarian SKOV3, SKOV/T320 (resistant to taxol) 2008 and 2008/T320 (resistant to taxol) cells are analyzed for surface exposure of HSC70 by direct binding of 125-iodine labeled anti-HSC70 to the surface of the cells. To do this, anti-HSC70 and mouse IgG1 (isotype matching negative control Sigma, M-9035) are iodinated using IODO-GEN® precoated iodination tubes (Pierce, #28601) following the procedure given by the manufacturer (average activity obtained: 7.5 mCi/mg).

Cells are seeded at 20,000 cells per well into a 96 Stripwell™ plate (Costar, #9102). After an overnight growth in complete media (37° C., 0.5% CO2), wells are gently washed with 100 ml media containing 1% FBS and incubated for 1 hour at 37° C. (0.5% CO2) in 100 mL media containing 1% FBS and 0.1% sodium azide as well as 100 ng of radioiodinated anti-HSC70 (or IgG1). Mortality is checked prior to incubation by trypan blue staining and is typically less than 1%. After incubation, media is discarded, wells washed twice with 350 mL media containing 1% FBS, and individually counted in a gamma-counter.

Binding studies are performed on MDA/mito cells using increasing amounts of radiolabeled anti-HSC70 in an intact cell radioimmunoassay. Scatchard analysis is used to calculate the apparent dissociation constant (Kd) and the number of molecules of antibody bound per cell. The average number of molecules of anti-HSC70 bound per cell is obtained from the average of 5 independent Scatchard determinations.

The average number of HSC70 epitopes present on the surface of MDA/mito cells is determined from the Scatchard plot.

The number of HSC70 epitopes present on MCF-7, MCF-7/AR, MDA, SKOV3, SKOV/T320, 2008 and 2008/T320 is calculated from the fold difference in surface exposure between these cell lines and MDA/mito. This fold is determined by testing the same number of MDA/mito cells and cells listed above (about 20,000 cells) using the above intact cell radioimmunoassay with 100 ng of radiolabeled anti-HSC70. The results show that MDR cell lines express more cell surface HSC70 epitopes than do non-MDR neoplastic cell lines of the same cell type or origin.

Example 17

5.17 Induction of Cell Surface Exposure of HSC70 in Breast and Ovarian Cancer Cells It is of further interest to determine whether these drugs are capable of inducing surface exposure of HSC70 in MDA and SKOV3 cell lines. To do this, 20,000 cells are seeded into a 96 Stripwell™ plate (Costar, #9102). After 5 h, the culture media is removed and replaced with culture media containing various drugs and incubated for 12 to 16 hours at 37° C. (0.5% CO2). After incubation, wells are gently washed with 100 mL media containing 1% FBS and incubated for 1 hour at 37° C. (0.5% CO2) in 100 mL media containing 1% FBS and 0.1% sodium azide as well as 100 ng of radioiodinated anti-HSC70 (or IgG1) (labeling procedure is given in example above). Mortality is checked prior to incubation by trypan blue staining and is typically less than 1%. After incubation, media is discarded, wells washed twice with 350 mL media containing 1% FBS, and individually counted in a gamma-counter. The surface exposure of HSC70 when MDA cells are incubated with 1 or 10 mM taxol, 1 or 10 mM doxorubicin, or 0.1 or 1 mM mitoxanthrone is thereby determined. Values are corrected for non-specific binding with IgG1.

Example 18

5.18 Internalization of $^{125}$I-labeled Anti-HSC70 by MCF-7/AR. MDA, MDA/AR and MDA/mito cells Internalization of cell surface HSC70 is measured on breast cancer cells kept in suspension or cells adhered in a 96 well plate. 106 cells are subcultured with a dissociation buffer (Gibco, #13150-016), and then transferred to a borosilicate tube, washed in PBS and resuspended in 200 ml alpha-MEM, 3% BSA containing 1 mg of radioiodinated anti-HSC70, or 1 mg of anti-Mucin-1 as positive control for internalization or 1 mg of IgG1 as background control. Mucin-1 (CD227) is a highly glycosylated protein ubiquitously present in many human tissues that, in tumor cells, is often produced at elevated levels and with an abnormal glycosylation pattern. Mouse antibodies have been used in clinical trials for the purpose of treating such cancers and are commercially available (e.g., from Fitzgerald Industries, Inc., Concord, Mass.). After 1 hour incubation at 4° C., cells are washed twice and further incubated additional 4 hours at 4° C. or 37° C. Cell viability is 100% according to trypan blue staining of cells prior to incubation with radiolabeled IgGs. After incubation, cells are washed and the radiolabel determined by counting samples in a gamma-counter. Cells are then stripped for 10 min at RT with 50 mM L-Gly, pH 2.8, 150 mM NaCl, washed and counted for residual activity in a gamma counter. The percent of surface associated radiolabel (stripped with L-Gly) and internalized (remaining after stripping) for MCF-7/AR cells at 4° C. and 37° C. is determined. The % internalization is obtained from the difference in internalization measured at 4 and 37° C. and is significant.

The results show that anti-HSC70 antibodies attached to a radionuclide therapeutic agent (or diagnostic probe) bind to cell surface HSC70 present on the surface of multidrug resistant breast epithelial neoplastic cells, and are actively internalized in a temperature-dependent manner. The temperature dependence suggests that the antibody-125I conjugate is actively taken up by endocytosis. Regardless of the mechanism of uptake, the results indicate that anti-HSC70 antibodies are capable of recognizing and transporting therapeutic agents (or diagnostic agents) into MDR neoplastic cells for the treatment (or diagnostic detection) of such cells. Therefore, these results further support the usefulness of anti-HSC70 antibodies for the targeting and uptake of linked therapeutic and diagnostic agents for both neoplastic, and MDR neoplastic cells.

EQUIVAENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method for detecting multidrug resistance or multidrug resistance potential in a test neoplastic cell, comprising:
   a) measuring a level of cell surface-expressed HSC70 protein in the test neoplastic cell of a given origin or cell type; and
   b) comparing the level of cell surface-expressed HSC70 protein in the test neoplastic cell to the level of cell surface-expressed HSC70 in a nonresistant neoplastic cell of the same origin or cell type,
   wherein the test neoplastic cell is multidrug resistant or has multidrug resistance potential if the level of cell surface-expressed HSC70 in the test neoplastic cell is greater than the level of cell surface-expressed HSC70 in the nonresistant neoplastic cell of the same given origin or cell type.

2. The method of claim 1, wherein measuring the level of cell surface-expressed HSC70 in the test neoplastic cell comprises isolating a cytoplasmic membrane fraction from the cell and measuring the level of HSC70 in the cytoplasmic membrane fraction.

3. The method of claim 1, wherein measuring the level of cell surface-expressed HSC70 in the test neoplastic cell comprises contacting said cell with an anti-HSC70 antibody and measuring the level of antibody bound to cell surface HSC70.

4. The method of claim 3, wherein measuring the level of antibody bound to cell surface HSC70 is by immunofluorescence emission.

5. The method of claim 3, wherein measuring the level of antibody bound to cell surface HSC70 is by radiolabel.

6. The method of claim 1, wherein the test neoplastic cell is selected from the group consisting of a promyleocytic leukemia cell, a T lymphoblastoid cell, a breast epithelial cell, and an ovarian cell.

7. The method of claim 1, wherein the nonresistant neoplastic cell is from a drug-sensitive cell line selected from the group consisting of HL60, NB4, CEM, HSB2 Molt4, MCF-7, MDA, SKOV-3, and 2008.

8. The method of claim 1, wherein the test neoplastic cell is selected from the group consisting of a lymphoma cell, a melanoma cell, a sarcoma cell, a leukemia cell, a retinoblastoma cell, a hepatoma cell, a myeloma cell, a glioma cell, a mesothelioma cell, and a carcinoma cell.

9. The method of claim 1, wherein the test neoplastic cell is from a tissue selected from the group consisting of blood, bone marrow, spleen, lymph node, liver, thymus, kidney, brain, skin, gastrointestinal tract, eye, breast, prostate, and ovary.

* * * * *

(12) EX PARTE REEXAMINATION CERTIFICATE (6254th)
United States Patent
Georges et al.

(10) Number: US 7,226,748 C1
(45) Certificate Issued: Jun. 10, 2008

(54) HSC70 DIRECTED DIAGNOSTICS AND THERAPEUTICS FOR MULTIDRUG RESISTANT NEOPLASTIC DISEASE

(75) Inventors: Elias Georges, Laval (CA); Lucile Serfass, Montreal (CA); Anne-Marie Bonneau, Laval (CA); Frédéric Dallaire, Montreal (CA)

(73) Assignee: Aurelium Biopharma, Inc., Montreal, Quebec (CA)

Reexamination Request:
No. 90/008,916, Nov. 13, 2007

Reexamination Certificate for:
Patent No.: 7,226,748
Issued: Jun. 5, 2007
Appl. No.: 10/737,350
Filed: Dec. 15, 2003

Related U.S. Application Data

(60) Provisional application No. 60/438,012, filed on Jan. 3, 2003.

(51) Int. Cl.
*G01N 33/53* (2006.01)

(52) U.S. Cl. .......... 435/7.1; 436/501; 436/518
(58) Field of Classification Search .......... None
See application file for complete search history.

(56) References Cited

U.S. PATENT DOCUMENTS

2002/0177212 A1 * 11/2002 Patterson et al.

FOREIGN PATENT DOCUMENTS

WO   WO-97/06821   *   2/1997

* cited by examiner

*Primary Examiner*—Bennett Celsa

(57) ABSTRACT

Disclosed are methods for detecting neoplastic or damaged cells and for detecting multidrug resistance in neoplastic or damaged cells by detecting an increase in the cell surface expression of a heat shock cognate (HSC70) protein 70 on the surface of such a multidrug resistant neoplastic or damaged cells as compared to the level of expression of the HSC70 protein on the surface of a normal cell.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *